United States Patent
Hattori et al.

(10) Patent No.: US 10,266,482 B2
(45) Date of Patent: Apr. 23, 2019

(54) LONG-TERM MEMORY INDUCING AGENT

(71) Applicants: NATIONAL UNIVERSITY CORPORATION TOKYO MEDICAL AND DENTAL UNIVERSITY, Tokyo (JP); SOPHIA SCHOOL CORPORATION, Tokyo (JP)

(72) Inventors: Atsuhiko Hattori, Tokyo (JP); Yukihisa Matsumoto, Tokyo (JP); Hiroyuki Kagechika, Tokyo (JP); Hiroyuki Masuno, Tokyo (JP); Atsuhiko Chiba, Tokyo (JP); Hikaru Iwashita, Tokyo (JP); Yusuke Maruyama, Tokyo (JP)

(73) Assignees: National University Corporation Tokyo Medical and Dental University, Tokyo (JP); Sophia School Corporation, Tokyo (JP)

( * ) Notice: Subject to any disclaimer, the term of this patent is extended or adjusted under 35 U.S.C. 154(b) by 0 days.

(21) Appl. No.: 15/593,571

(22) Filed: May 12, 2017

(65) Prior Publication Data
US 2018/0327348 A1 Nov. 15, 2018

(51) Int. Cl.
| | | |
|---|---|---|
| *C07D 403/12* | (2006.01) | |
| *C07C 223/06* | (2006.01) | |
| *C07C 211/48* | (2006.01) | |
| *C07C 49/657* | (2006.01) | |
| *A61K 31/12* | (2006.01) | |
| *A61K 31/136* | (2006.01) | |

(52) U.S. Cl.
CPC ............ *C07C 223/06* (2013.01); *A61K 31/12* (2013.01); *A61K 31/136* (2013.01); *C07C 49/657* (2013.01); *C07C 211/48* (2013.01); *A61K 2300/00* (2013.01)

(58) Field of Classification Search
CPC .................................................. C07C 223/06
See application file for complete search history.

(56) References Cited

U.S. PATENT DOCUMENTS

| | | | | |
|---|---|---|---|---|
| 5,547,991 A | * | 8/1996 | Palfreyman | C07C 229/42 514/564 |
| 5,786,508 A | * | 7/1998 | Schwarcz | C07C 229/36 560/39 |
| 9,708,247 B2 | * | 7/2017 | Walter | C07C 235/14 |
| 2005/0137247 A1 | * | 6/2005 | Czeisler | A61K 31/343 514/419 |
| 2012/0288485 A1 | * | 11/2012 | Broady | A61K 45/06 424/94.1 |
| 2016/0368860 A1 | * | 12/2016 | Kikuchi | A61K 31/165 |
| 2017/0172180 A1 | * | 6/2017 | Zanghi | A23K 20/147 |

FOREIGN PATENT DOCUMENTS

| | | | | |
|---|---|---|---|---|
| CN | 1314151 A | * | 9/2001 | |
| EP | 1903028 A1 | * | 3/2008 | ........... A61K 31/198 |
| JP | 4993900 B2 | | 8/2012 | |
| JP | 2016-166197 A | | 9/2016 | |
| JP | 2016166197 A | * | 9/2016 | |
| WO | WO-0067803 A1 | * | 11/2000 | ......... A01K 67/0275 |
| WO | WO-2007054348 A1 | * | 5/2007 | ............. A61K 31/00 |
| WO | WO-2017044516 A1 | * | 3/2017 | ........... C07C 271/22 |

OTHER PUBLICATIONS

A. Ressnneyer et al., 8 Redox Report, 205-213 (2003).*
J.C. Mayo et al., 165 Journal of Neuroimmunology,139-149 (2005).*
N. Lopatina et al., 41 Neuroscience and Behavioral Physiology, 626-631 (2011).*
D. Zadori et al., 116 Journal of Neural Transmission, 1403-1409 (2009).*
R.S. Phillips et al., 27 Bioorganic & Medicinal Chemistry Letters, 1705-1708 (2017).*
R. Kelly et al., 121 Biochemical and Biophysical Research Communications, 372-379 (1984).*
E. Camacho et al., 45 Journal of Medicinal Chemistry, 263-274 (2002).*
Schutt, English Language Machine Translation of WO 2007/054348 (2007).*
P. Carrillo-Mora et al., 210 Behavioural Brain Research, 240-250 (2010).*
R. Hardeland, Melatonin: From Molecules to Therapy, 23-32 (2007).*
P.J. Marangos et al., 29 Life Sciences, 259-267 (1981).*
IUPAC. Compendium of Chemical Terminology, 2nd ed. (the "Gold Book") (1997).*

* cited by examiner

*Primary Examiner* — Alexander R Pagano
(74) *Attorney, Agent, or Firm* — McDermott Will & Emery LLP

(57) ABSTRACT

[Problem] To provide a method for inducing a long-term memory in a subject in need thereof.
[Solution to problem] A method for inducing a long-term memory, comprising a step of administering a compound represented by Formula I below, a pharmaceutically acceptable salt thereof or a solvate thereof to the subject.

(I)

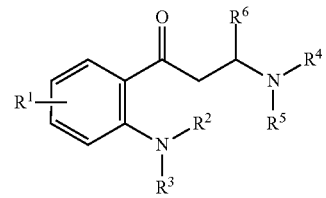

6 Claims, 12 Drawing Sheets

Aged cricket (3-week-old)

LONG-TERM MEMORY INDUCING AGENT

TECHNICAL FIELD

The present invention relates to a long-term memory inducing agent, in particular to a long-term memory inducing agent comprising a metabolite of melatonin or a derivative thereof, to use of the same for inducing a long-term memory, to a method for treating a memory disorder by using the same, and the like.

BACKGROUND ART

Learning and memory are basic functions of the brain that are necessary for an animal to adapt to the environment. Elucidation of the neural mechanisms of learning/memory is one of the important issues in the field of neurobehavioral study/neurophysiology, and researches have been conducted to date in various animal species. Among them, insects have a high level of learning ability considering a relatively small number of nerve cells and a simple structure of the nervous system, and therefore they are a very useful material for studying learning/memory.

The present inventors have conducted studies of molecular mechanism of learning/memory by employing an olfactory associative learning system using Gryllus bimaculatus (hereinafter, referred to as a "cricket") as a material and water as a reward stimulus. When adult crickets receive olfactory reward associative conditioning once by being given water in a thirsty state while smelling a certain smell (for example, peppermint), associative learning between the reward and the smell is established and they tend to favor that smell. This memory, however, is a short-term memory that is lost in a few hours. When the associative conditioning is conducted for three or more times at intervals, a long-term memory that persists for life can be formed. Similar to long-term memories in other animal species, long-term memories of crickets are dependent on protein synthesis. Moreover, a number of biological molecules that play an important role in formation of long-term memories in crickets have been identified, including nitrogen monoxide (NO), cGMP, cAMP, PKA and else, where many of them are also found to be important for the process of long-term memory formation in mice and rats. These substances, however, are not recognized to be effective in enhancing a memory when administered after the training. Searching for a substance that is capable of enhancing a memory not only before the training but even after the training appears to be beneficial in treating learning disorders and the like.

Recently, the present inventors found that formation of short-term memories is normal but formation of long-term memories is significantly deteriorated in aged crickets older than the average lifetime (age-related memory disorders). Age-related memory disorders have been recognized not only in rodents such as rats and mice, but also in invertebrates such as drosophila and nematodes. While there are various theories regarding the causes of age-related memory disorders, "active oxygen theory" is gaining broad acceptance, which suggests that active oxygen increasing with age gives damage to protein, DNA and else constituting the cells. Melatonin known as an antioxidant substance is believed to be effective for age-related memory disorders. For example, in the previous study by the present inventors, melatonin was mixed into a feed or water and given to mice, drosophila and crickets as experimental animals over a long period of time, by which age-related memory disorders were prevented (Name of Document: Japanese Patent No. 4993900). However, the mechanism of the age-related memory disorder has not yet been understood.

PRIOR ART DOCUMENTS

Patent Document

Patent document 1: Japanese Patent No. 4993900

SUMMARY OF INVENTION

Problem to be Solved by Invention

The present invention has an objective of providing a long-term memory inducing agent.

Means for Solving Problem

Searching of a substance that has an effect of improving an age-related memory disorder even with a single-dose administration is considered to contribute to the treatment of dementia. Accordingly, the present inventors have gone through intensive research to solve the above-described problem, and as a result of which found that a metabolite of melatonin and a derivative thereof are primarily effective in inducing a long-term memory, thereby accomplishing the present invention.

Thus, the present invention is as follows.

(1) A method for inducing a long-term memory in a subject in need thereof, comprising a step of administering a compound represented by Formula I below, a pharmaceutically acceptable salt thereof or a solvate thereof to the subject:

[Chemical formula 1]

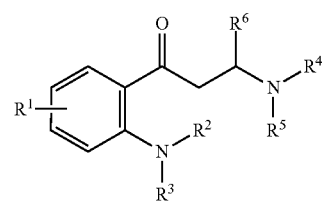

(I)

(wherein, $R^1$, $R^2$, $R^3$, $R^4$, $R^5$ and $R^6$ each independently represent a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-21}$ acyl group, an optionally substituted heteroaryl carbonyl group, an optionally substituted $C_{2-7}$ alkoxycarbonyl group, a formyl group, a carboxyl group, a hydroxyl group or a halogen atom).

(2) The method according to (1), wherein $R^1$ is selected from the group consisting of a hydrogen atom, an optionally substituted $C_{1-6}$ alkoxy group and a halogen atom.

(3) The method according to either one of (1) and (2), wherein at least one of $R^4$ and $R^5$ is an optionally substituted $C_{2-21}$ acyl group or an optionally substituted heteroaryl carbonyl group.

(4) The method according to any one of (1) to (3), wherein $R^2$ and $R^3$ are both hydrogen atoms or at least one of them is a formyl group.

(5) The method according (1), wherein the compound represented by Formula I is any one of Compounds 1-16 below:
[Chemical formula 2]
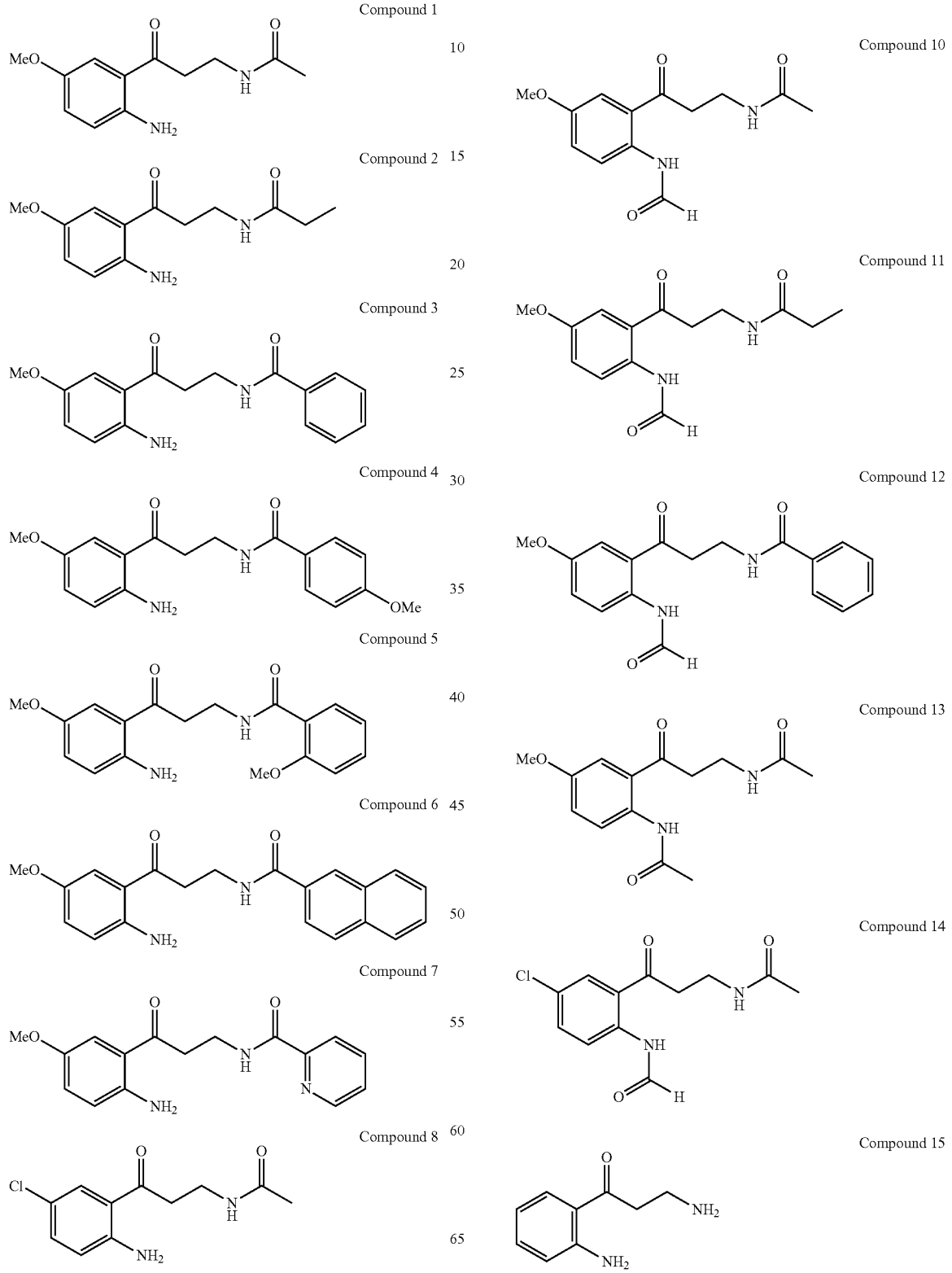

Compound 16

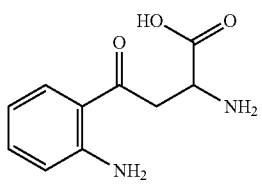

(6) A method for treating a memory disorder in a subject in need thereof, comprising a step of administering a compound represented by Formula I below, a pharmaceutically acceptable salt thereof or a solvate thereof to the subject:

[Chemical formula 3]

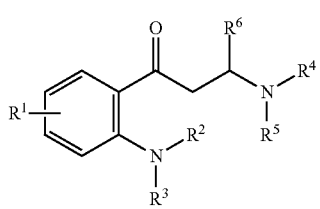

(I)

(wherein, $R^1$, $R^2$, $R^3$, $R^4$, $R^5$ and $R^6$ each independently represent a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-21}$ acyl group, an optionally substituted heteroaryl carbonyl group, an optionally substituted $C_{2-7}$ alkoxycarbonyl group, a formyl group, a carboxyl group, a hydroxyl group or a halogen atom).

(7) The method according to (6), wherein $R^1$ is selected from the group consisting of a hydrogen atom, an optionally substituted $C_{1-6}$ alkoxy group and a halogen atom.

(8) The method according to either one of (6) and (7), wherein at least one of $R^4$ and $R^5$ is an optionally substituted $C_{2-21}$ acyl group or an optionally substituted heteroaryl carbonyl group.

(9) The method according to any one of (6) to (8), wherein $R^2$ and $R^3$ are both hydrogen atoms, or at least one of them is a formyl group.

(10) The method according to (6), wherein the compound represented by Formula I is any one of Compounds 1-16 below:

[Chemical formula 4]

Compound 1

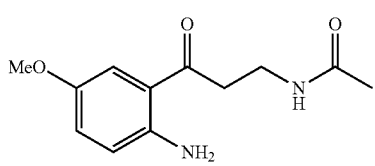

Compound 2

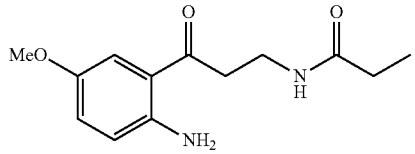

Compound 3

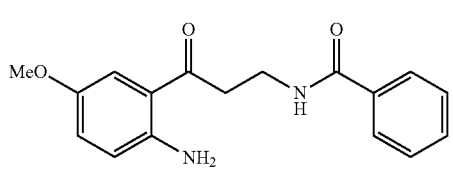

Compound 4

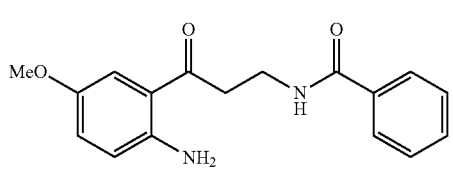

Compound 5

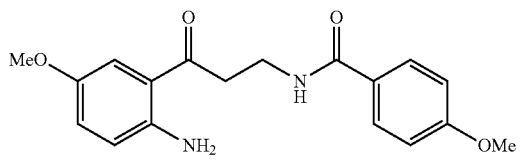

Compound 6

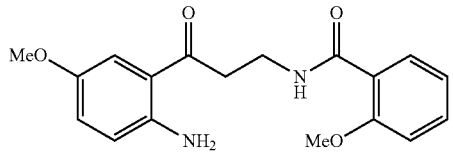

Compound 7

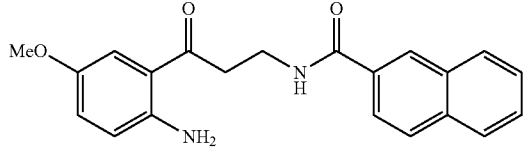

Compound 8

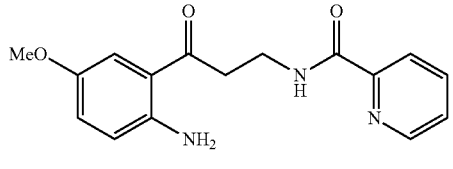

Compound 9

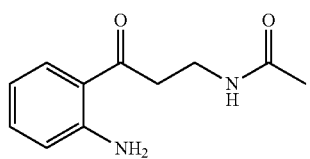

-continued

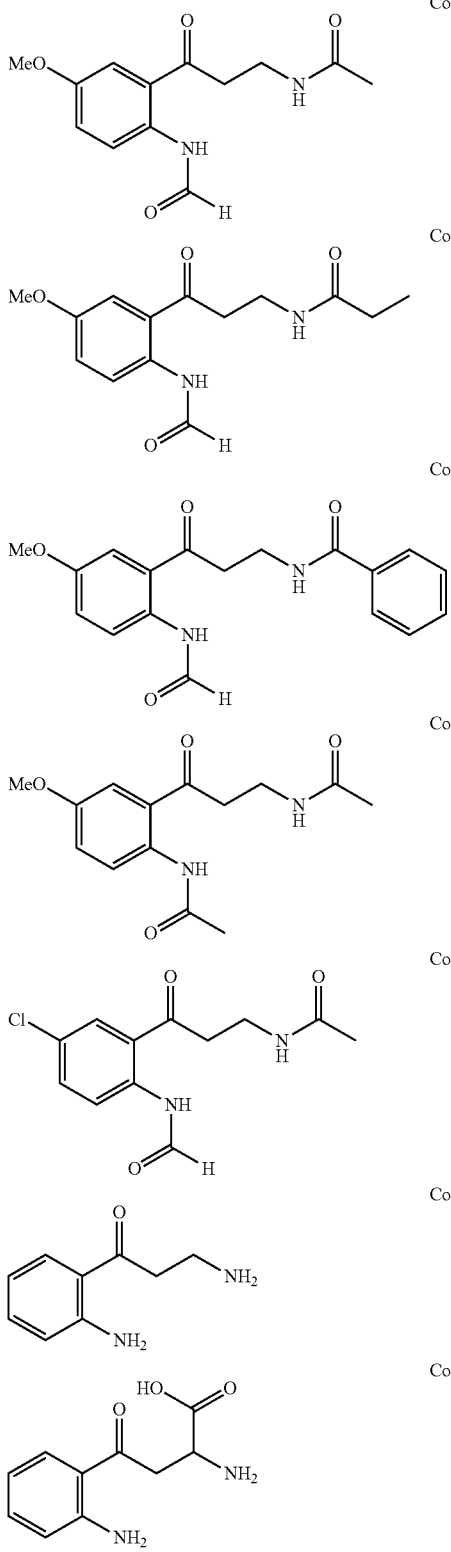

Compound 10

Compound 11

Compound 12

Compound 13

Compound 14

Compound 15

Compound 16

(11) A method for inducing a long-term memory in a subject in need thereof, comprising a step of ingesting functional food containing a compound represented by Formula I below, a pharmaceutically acceptable salt thereof or a solvate thereof:

[Chemical formula 5]

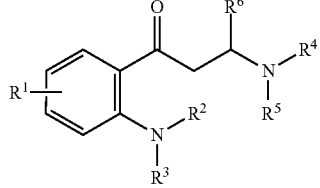

(I)

(wherein, $R^1$, $R^2$, $R^3$, $R^4$, $R^5$ and $R^6$ each independently represent a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-21}$ acyl group, an optionally substituted heteroaryl carbonyl group, an optionally substituted $C_{2-7}$ alkoxycarbonyl group, a formyl group, a carboxyl group, a hydroxyl group or a halogen atom).

(12) The method according to (11), wherein $R^1$ is selected from the group consisting of a hydrogen atom, an optionally substituted $C_{1-6}$ alkoxy group and a halogen atom.

(13) The method according to either one of (11) and (12), wherein at least one of $R^4$ and $R^5$ is an optionally substituted $C_{2-21}$ acyl group or an optionally substituted heteroaryl carbonyl group.

(14) The method according to any one of (11) to (14), wherein $R^2$ and $R^3$ are both hydrogen atoms, or at least one of them is a formyl group.

(15) The method according to (11), wherein the compound represented by Formula I is any one of Compounds 1-16 below:

[Chemical formula 6]

Compound 1

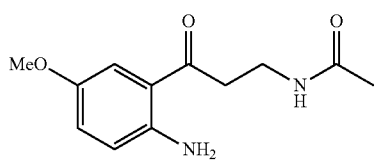

Compound 2

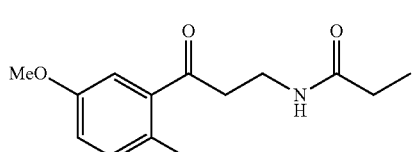

Compound 3

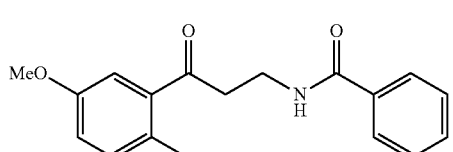

Compound 4
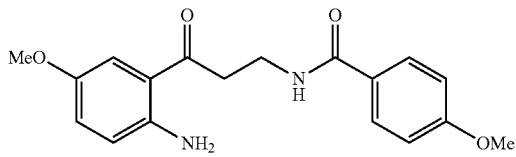

Compound 5
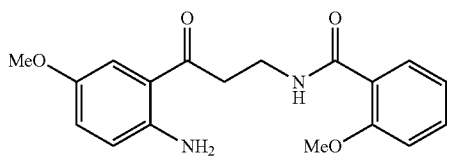

Compound 6
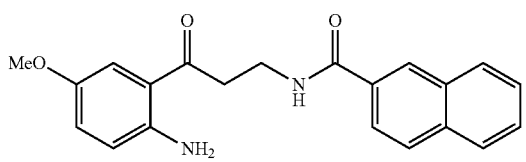

Compound 7
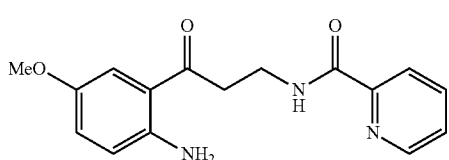

Compound 8
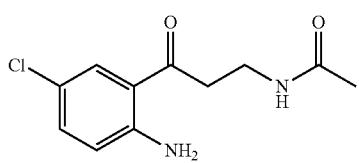

Compound 9
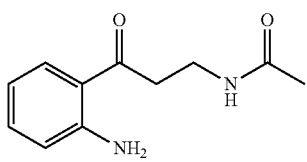

Compound 10
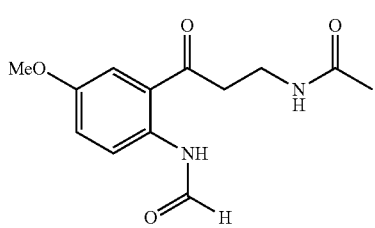

Compound 11
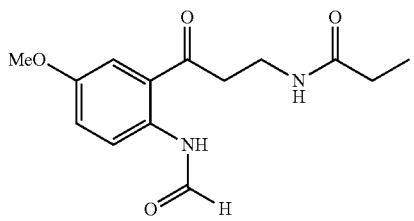

Compound 12
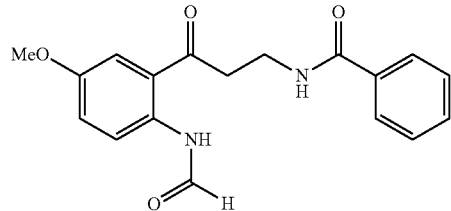

Compound 13
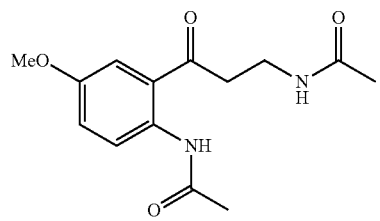

Compound 14
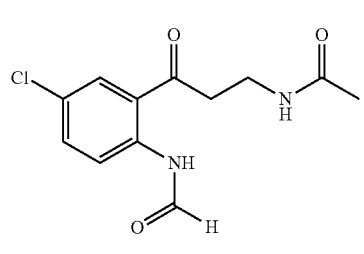

Compound 15
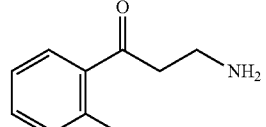

Compound 16
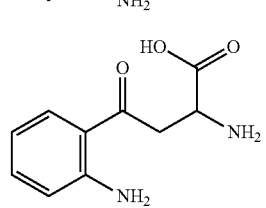

(16) A compound represented by Formula I below, a pharmaceutically acceptable salt thereof or a solvate thereof:

[Chemical formula 7]

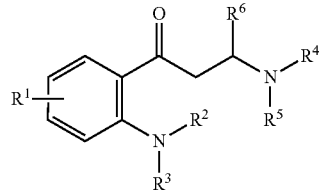

(wherein, $R^1$, $R^2$, $R^3$, $R^4$, $R^5$ and $R^6$ each independently represent a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-21}$ acyl group, an optionally substituted heteroaryl carbonyl group, an optionally substituted $C_{2-7}$ alkoxycarbonyl group, a formyl group, a carboxyl group or a hydroxyl group),
wherein the following compounds are excluded:
N-[3-(2-amino-5-methoxyphenyl)-3-oxopropyl]-acetamide;
N-[3-(2-formylamino-5-methoxyphenyl)-3-oxopropyl]acetamide;
3-[(2-aminophenyl)carbonyl]-2-aminopropionic acid; and
3-amino-1-(2-aminophenyl)-1-propanone.

Furthermore, another aspects of the present invention are as follows.

(1) A long-term memory inducing agent comprising a compound represented by Formula I below, a pharmaceutically acceptable salt thereof or a solvate thereof:

[Chemical formula 8]

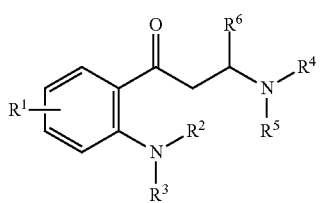

(I)

(wherein, $R^1$, $R^2$, $R^3$, $R^4$, $R^5$ and $R^6$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-7}$ acyl group, an optionally substituted $C_{2-7}$ alkoxycarbonyl group, a formyl group, a carboxyl group or a hydroxyl group).

(2) The long-term memory inducing agent according to (1), wherein $R^1$ is an optionally substituted $C_{1-6}$ alkoxy group.

(3) The long-term memory inducing agent according to either one of (1) and (2), wherein at least one of $R^4$ and $R^5$ is a $C_{2-7}$ acyl group.

(4) The long-term memory inducing agent according to (1), wherein the compound represented by Formula I is one represented by Formula II, III, IV or V below:

[Chemical formula 9]

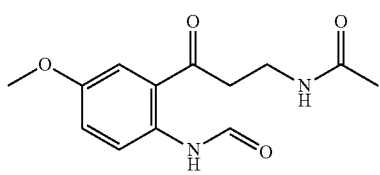

(II)

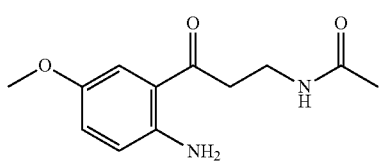

(III)

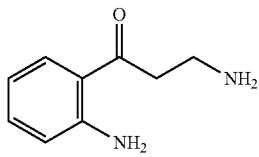

(IV)

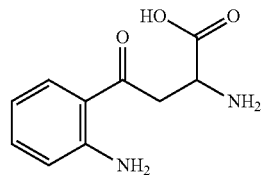

(V)

(5) A pharmaceutical composition for treating a memory disorder comprising a compound represented by Formula I below, a pharmaceutically acceptable salt thereof or a solvate thereof:

[Chemical formula 10]

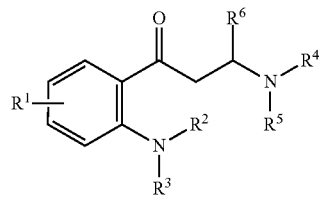

(I)

(wherein, $R^1$, $R^2$, $R^3$, $R^4$, $R^5$ and $R^6$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-7}$ acyl group, an optionally substituted $C_{2-7}$ alkoxycarbonyl group, a formyl group, a carboxyl group or a hydroxyl group).

(6) The pharmaceutical composition according to (5), wherein $R^1$ is an optionally substituted $C_{1-6}$ alkoxy group.

(7) The pharmaceutical composition according to either one of (5) and (6), wherein at least one of $R^4$ and $R^5$ is a $C_{2-7}$ acyl group.

(8) The pharmaceutical composition according to (5), wherein the compound represented by Formula I is one represented by Formula II, III, IV or V below:

[Chemical formula 11]

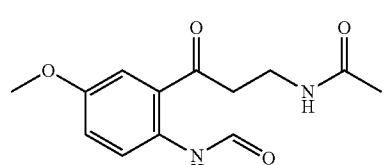

(II)

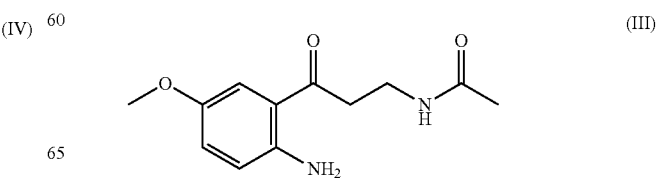

(III)

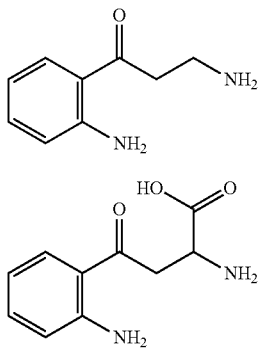

(IV)

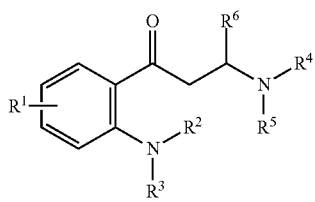

(V)

(9) Functional food comprising a compound represented by Formula I below, a pharmaceutically acceptable salt thereof or a solvate thereof:

[Chemical formula 12]

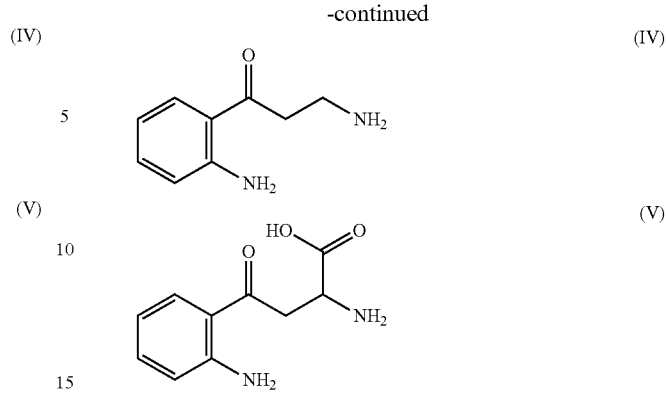

(I)

(wherein, $R^1$, $R^2$, $R^3$, $R^4$, $R^5$ and $R^6$ each independently represent a hydrogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-7}$ acyl group, an optionally substituted $C_{2-7}$alkoxycarbonyl group, a formyl group, a carboxyl group or a hydroxyl group).

(10) The functional food according to (9), wherein $R^1$ is an optionally substituted $C_{1-6}$ alkoxy group.

(11) The functional food according to either one of (9) and (10), wherein at least one of $R^4$ and $R^5$ is a $C_{2-7}$ acyl group.

(12) The functional food according to (9), wherein the compound represented by Formula I is one represented by Formula II, III, IV or V below:

[Chemical formula 13]

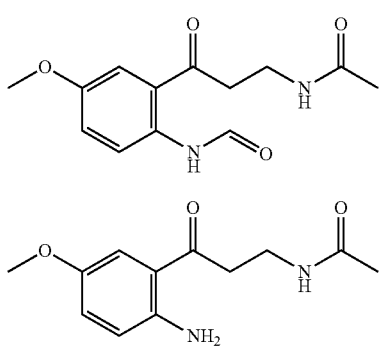

(IV)

(V)

Effects of Invention

The present invention can provide a long-term memory inducing agent. The long-term memory inducing agent of the present invention can induce a memory by being administrated either before or after training. Accordingly, the long-term memory inducing agent of the present invention is useful as a therapeutic agent for a memory disorder.

MODES FOR CARRYING OUT INVENTION

Figure 1:
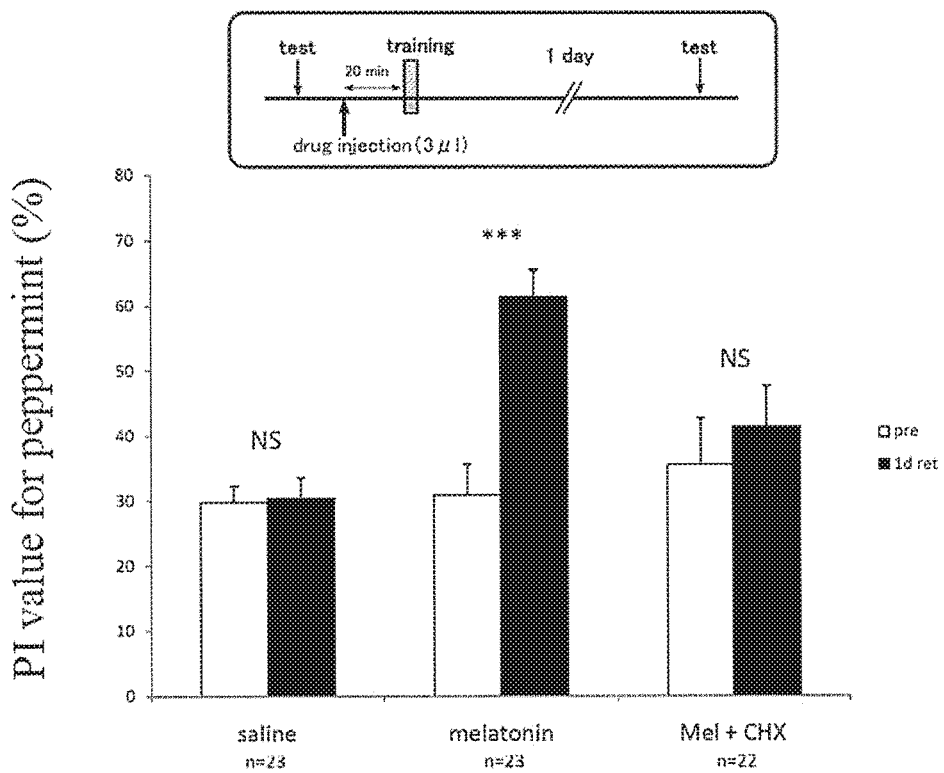
FIG. 1 A diagram showing an effect of melatonin in inducing a long-term memory. Physiological saline, melatonin (5 µM), and melatonin and cycloheximide (10 mM) were administered to the brain 20 minutes before the single-time olfactory reward conditioning/training. Preference was tested before the training (white bars) and a day after the training (black bars) to determine the PI value for mint (the same applies hereinafter). The figures under the graph represent the number of crickets used (the same applies hereinafter). The test results are expressed as *: $p<0.001$, : $p<0.01$, $p<0.05$, and NS: $p>0.05$ (no significant difference) (the same applies hereinafter). The panel above the graph shows the time schedule of the experiment (the same applies hereinafter).

Hereinafter, the present invention will be described in detail. The present invention should not be limited to the following embodiments, illustrated products and the like, and can be modified and carried out without departing from the spirit of the present invention. All of the documents and publications cited herein are incorporated herein by reference in their entirety for any and all purposes. In addition, the contents disclosed in the claims, the specification, the drawings and the abstract of Japanese Unexamined Patent Application Publication No. 2016-166197 are incorporated herein by reference in their entirety.

1. Compounds

A compound used in the present invention is represented by General formula I, which includes a pharmaceutically acceptable salt thereof and a solvate thereof. These compounds may have an effect of inducing a long-term memory.

[Chemical formula 14]

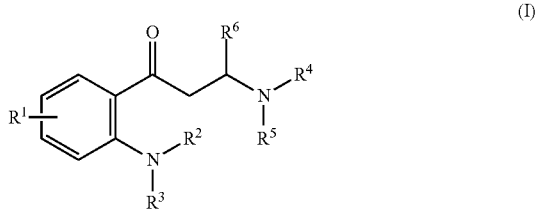

(I)

In Formula I above, $R^1$, $R^2$, $R^3$, $R^4$, $R^5$ and $R^6$ each independently represent a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-21}$ acyl group, an optionally substituted heteroaryl carbonyl group, an optionally substituted $C_{2-7}$ alkoxycarbonyl group, a formyl group, a carboxyl group or a hydroxyl group.

Herein, a "halogen atom" refers to a fluorine atom (F), a chlorine atom (Cl), a bromine atom (Br) or an iodine atom (I). A preferable halogen atom is a chlorine atom.

Herein, a "$C_{1-6}$ alkyl group" refers to a linear or branched alkyl group with a carbon number of 1-6, for example, a methyl group, an ethyl group, a 1-propyl group (n-propyl group), a 2-propyl group (i-propyl group), a 2-methyl-1-propyl group (i-butyl group), a 2-methyl-2-propyl group (t-butyl group), a 1-butyl group (n-butyl group), a 2-butyl group (s-butyl group), a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group and a 2,3-dimethyl-2-butyl group.

Preferable examples of the $C_{1-6}$ alkyl group include a methyl group, an ethyl group, a 1-propyl group, a 2-propyl group, a 1-butyl group and a 2-butyl group.

Herein, a "$C_{2-6}$ alkenyl group" refers to a linear or branched alkenyl group having a double bond and a carbon number of 2-6, for example, an ethenyl group (vinyl group), 1-propenyl group, a 2-propenyl group (allyl group), a 1-butenyl group, a 2-butenyl group, a 3-butenyl group, a pentenyl group and a hexenyl group.

Herein, a "$C_{2-6}$ alkynyl group" refers to a linear or branched alkynyl group having a triple bond and a carbon number of 2-6, for example, an ethynyl group, a 1-propynyl group, a 2-propynyl group, a 1-butynyl group, a 2-butynyl group, a 3-butynyl group, a pentynyl group and a hexynyl group.

Herein, a "$C_{1-6}$ alkoxy group" refers to a group that has an oxygen atom bound to the terminal of the above-described $C_{1-6}$ alkyl group, for example, a methoxy group, an ethoxy group, a 1-propoxy group (n-propoxy group), a 2-propoxy group (i-propoxy group), a 2-methyl-1-propoxy group (i-butoxy group), a 2-methyl-2-propoxy group (t-butoxy group), a 1-butoxy group (n-butoxy group), a 2-butoxy group (s-butoxy group), a 1-pentyloxy group, a 2-pentyloxy group, a 3-pentyloxy group, a 2-methyl-1-butoxy group, a 3-methyl-1-butoxy group, a 2-methyl-2-butoxy group, a 3-methyl-2-butoxy group, a 2,2-dimethyl-1-propoxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butoxy group, a 3,3-dimethyl-1-butoxy group, a 2,2-dimethyl-1-butoxy group and a 2-ethyl-1-butoxy group.

Preferable examples of the $C_{1-6}$ alkoxy group include a methoxy group, an ethoxy group, a 1-propoxy group, a 2-propoxy group, a 1-butoxy group and a 2-butoxy group.

Herein, a "$C_{3-8}$ cycloalkyl group" refers to a monocyclic or bicyclic saturated aliphatic hydrocarbon group with a carbon number of 3-8, for example, a cyclopropyl group, a cyclobutyl group, a cyclopentyl group, a cyclohexyl group, a cycloheptyl group and a cyclooctyl group.

Herein, a "$C_{6-20}$ aryl group" refers to an aromatic hydrocarbon cyclic group with a carbon number of 6-20, for example, a phenyl group, a 1-naphthyl group, a 2-naphthyl group, an indenyl group and an azulenyl group.

The aryl group is preferably a "$C_{6-10}$ aryl group", where preferable examples include a phenyl group, a 1-naphthyl group and a 2-naphthyl group.

Herein, a "$C_{2-21}$ acyl group" refers to a carbonyl group bound with the "$C_{1-6}$ alkyl group" or the "$C_{6-20}$ aryl group" defined above, for example, an acetyl group, a propionyl group, an isopropionyl group, a butyryl group, an isobutyryl group, a valeryl group, an isovaleryl group, a pivaloyl group, a benzoyl group, a 1-naphthoyl group and a 2-naphthoyl group. Preferable examples of the $C_{2-21}$ acyl group include an acetyl group, a propionyl group, a benzoyl group and a 2-naphthoyl group. The "$C_{2-21}$ acyl group" is preferably a "$C_{2-7}$ acyl group", specifically a carbonyl group bound with the above-described "$C_{1-6}$ alkyl group" or a phenyl group, and particularly preferably an acetyl group, a propionyl group or a benzoyl group.

Herein, a "heteroaryl carbonyl group" refers to a carbonyl group bound with a heteroaryl group. A "heteroaryl group" refers to a 5- or 6-membered aromatic ring group containing 1, 2 or 3 heteroatoms (N, O or S) and 2-5 carbon atoms, where specific examples include a furyl group, a thienyl group, a pyrrolyl group, an oxazolyl group, a thiazolyl group, an imidazolyl group, a pyrazolyl group, an isoxazolyl group, an isothiazolyl group, an oxadiazolyl group, a triazolyl group, a thiadiazolyl group, a pyridinyl group, a pyridazinyl group, a pyrimidinyl group and a pyrazinyl group, among which a heteroaryl group containing a nitrogen atom is preferable. Specifically, preferable examples of the heteroaryl carbonyl group include a picolinoyl group (pyridine-2-carbonyl group), a nicotinoyl group (pyridine-3-carbonyl group), an isonicotinoyl group (pyridine-4-carbonyl group) and a pyrazine-2-carbonyl group, among which a picolinoyl group is particularly preferable.

Herein, a "$C_{2-7}$ alkoxycarbonyl group" refers to a carbonyl group bound with the "$C_{1-6}$ alkoxy group" defined above, where specific examples include a methoxycarbonyl group, an ethoxycarbonyl group, a 1-propyloxycarbonyl group, a 2-propyloxycarbonyl group, a 2-methyl-2-propoxy group and a 2-methyl-2-propoxycarbonyl group.

Herein, the term "optionally substituted" means that the group may have one or more substituents in any combination at a replaceable site.

Specific examples of the substituent include a halogen atom, a hydroxyl group, a thiol group, a nitro group, a cyano group, a formyl group, a carboxyl group, an amino group, a silyl group, a methane sulfonyl group, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a $C_{1-6}$ alkoxy group, a $C_{2-7}$ acyl group and a $C_{2-7}$ alkoxycarbonyl group.

According to the present invention, $R^1$ is preferably selected from the group consisting of a hydrogen atom, an optionally substituted $C_{1-6}$ alkoxy group and a halogen atom, and more preferably is an unsubstituted $C_{1-3}$ alkoxy group (more preferably a methoxy group) or a halogen atom (more preferably a chlorine atom).

Furthermore, at least one of $R^4$ and $R^5$ is, for example, preferably an optionally substituted $C_{2-21}$ acyl group or an optionally substituted heteroaryl carbonyl group, more preferably a $C_{1-6}$ alkylcarbonyl group, a $C_{6-20}$ aryl (preferably $C_{6-10}$ aryl) carbonyl group optionally substituted with a $C_{1-6}$ alkoxy group or an unsubstituted heteroaryl carbonyl group, and still more preferably an acetyl group; a propionyl group; a benzoyl group, a 1-naphthoyl group or a 2-naphthoyl group optionally substituted with a methoxy group; or a picolinoyl group.

Moreover, $R^2$ and $R^3$ are preferably both hydrogen atoms, or at least one of them is a formyl group (aldehyde).

A compound represented by Formula I of the present invention is preferably a compound represented by Formula Ia below.

[Chemical formula 15]

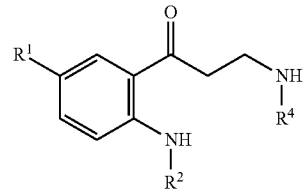

(Ia)

In Formula Ia, $R^1$, $R^2$ and $R^4$ are the same as defined in Formula I above. Moreover, preferable groups thereof are also the same as described above.

Specific compounds that are preferably used in the present invention are shown below.

[Chemical formula 16]

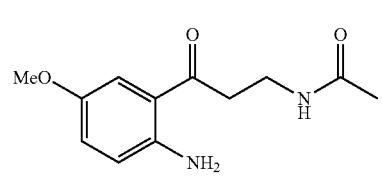

Compound 1

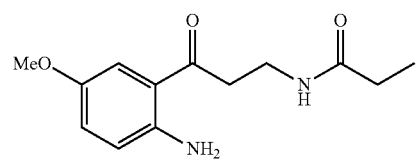

Compound 2

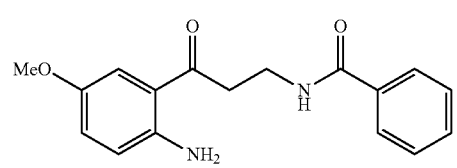

Compound 3

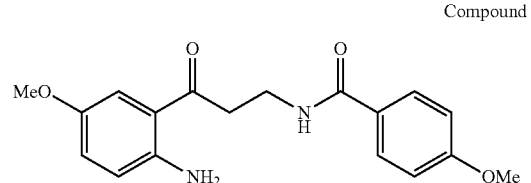

Compound 4

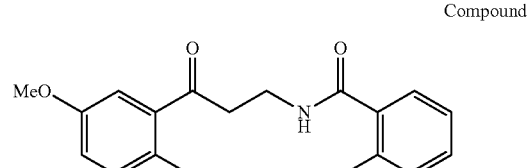

Compound 5

-continued

Compound 6
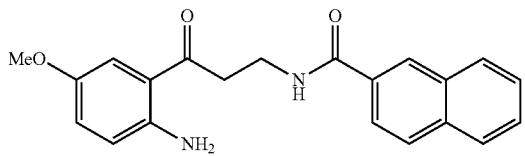

Compound 7
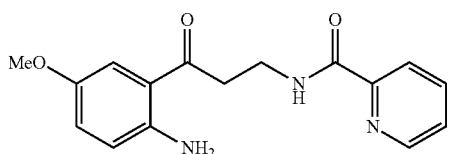

Compound 8
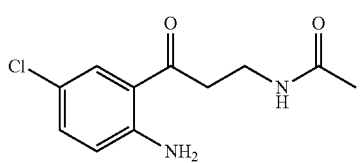

Compound 9
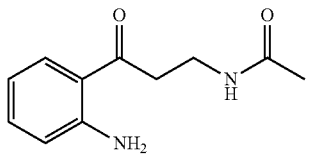

Compound 10
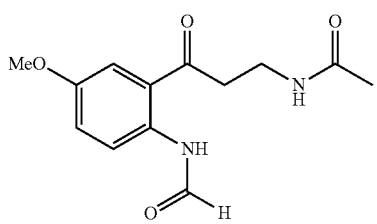

Compound 11
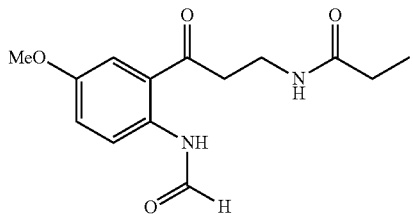

Compound 12
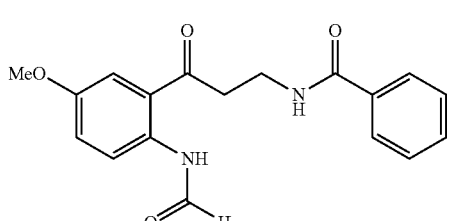

Compound 13
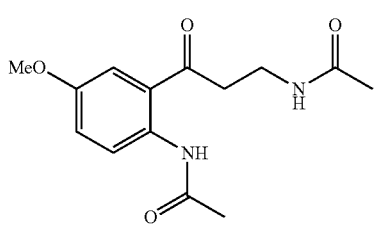

-continued

Compound 14
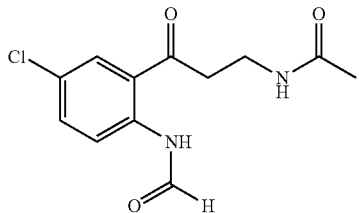

Compound 15
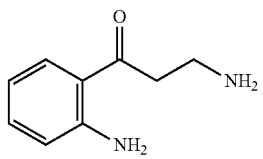

Compound 16
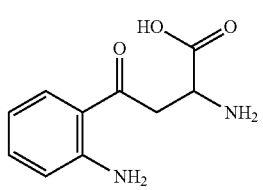

A compound represented by Formula II is called AFMK (N(1)-acetyl-N(2)-formyl-5-methoxykynuramine), which is a metabolic melatonin:

[Chemical formula 17]

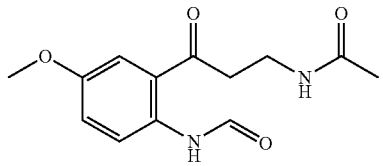

(II)

This compound is (N-[3-(2-formylamino-5-methoxyphenyl)-3-oxopropyl]acetamide), i.e., Compound 10 shown above.

A compound represented by Formula III below is called AMK (N(1)-acetyl-5-methoxykynuramine), which is a metabolite of melatonin:

[Chemical formula 18]

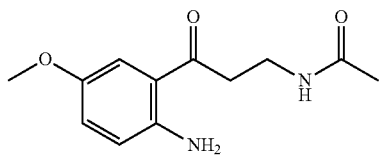

(III)

This compound is (N-[3-(2 amino-5-methoxyphenyl)-3-oxopropyl]-acetamide), i.e., Compound 1 shown above.

AFMK is a metabolite (decomposed product) of melatonin in the brain, and AMK is a metabolite (decomposed product) of AFMK in the brain. Both of AFMK and AMK are commercially available (Cayman Chemical and Toronto Research Chemicals, respectively).
The metabolic pathway of melatonin is shown below.
[Chemical formula 19]
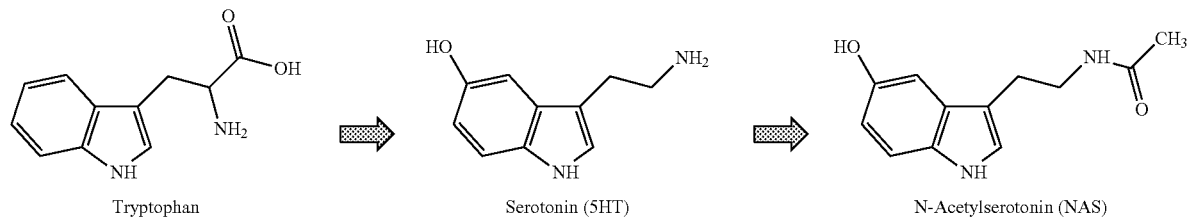
Tryptophan → Serotonin (5HT) → N-Acetylserotonin (NAS)
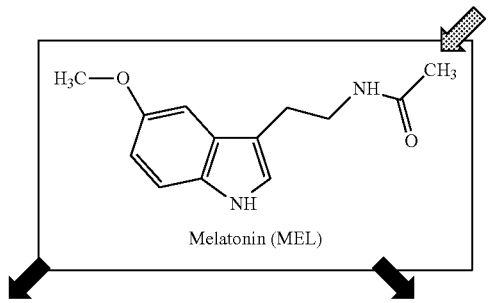
Melatonin (MEL)
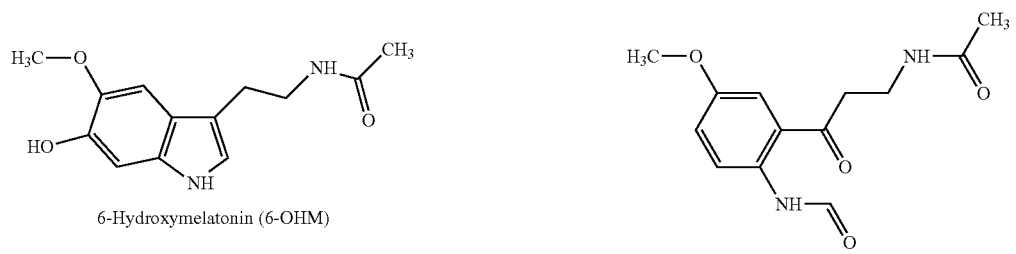
6-Hydroxymelatonin (6-OHM)   N-Acetyl-N-formil-5-methoxykynuramine (AFMK)
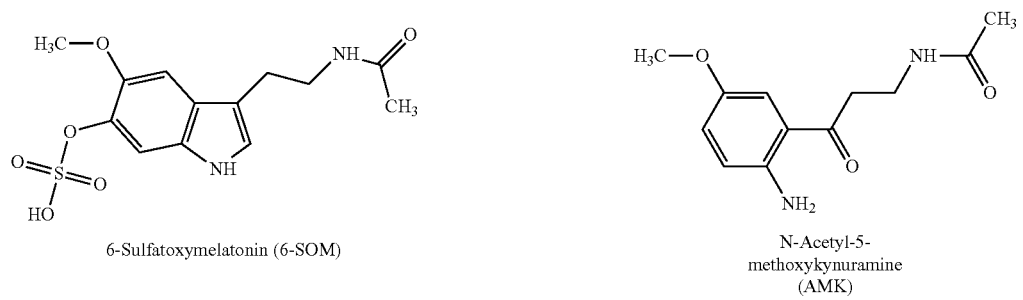
6-Sulfatoxymelatonin (6-SOM)   N-Acetyl-5-methoxykynuramine (AMK)

A compound represented by Formula IV below is called kynuramine:

[Chemical formula 20]

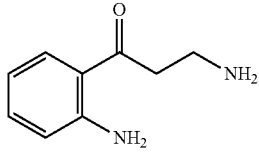

(IV)

This compound is (3-amino-1-(2-aminophenyl)-1-propanone), i.e., Compound 15 shown above.

A compound represented by Formula V below is called kynurenine:

[Chemical formula 21]

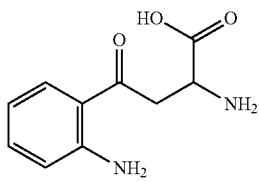

(V)

This compound is (3-[(2-aminophenyl)carbonyl]-2-aminopropionic acid), i.e., Compound 16 shown above.

Among them, a compound selected from the group consisting of Compound 1, Compound 2, Compound 3, Compound 8, Compound 9, Compound 10, Compound 11, Compound 12, Compound 13, Compound 14, Compound 15 and Compound 16 is preferable, a compound selected from the group consisting of Compounds 1-5, 7, 9, 15 and 16 is more preferable for having an excellent effect of inducing long-term memory, and a compound selected from the group consisting of Compounds 2, 3, 7 and 9 is particularly preferable.

According to the present invention, the compound represented by Formula I may be a commercially available product or may be obtained by synthesis. The compound represented by Formula I may be synthesized by a method described in the examples below or by a modified method thereof.

According to the present invention, any pharmaceutically acceptable salt of the compound represented by Formula I can be used. Examples of the "pharmaceutically acceptable salt" include, but not particularly limited to, salts formed with an acid and salts formed with a base.

Examples of the salts formed with an acid include inorganic acid salts such as hydrochloride, hydrobromide, sulfate and phosphate, and organic acid salts such as formic acid, acetic acid, lactic acid, succinic acid, fumaric acid, maleic acid, citric acid, tartaric acid, stearic acid, benzoic acid, methanesulfonic acid, benzenesulfonic acid, p-toluenesulfonic acid and trifluoroacetic acid.

In addition, examples of salts formed with a base include alkali metal salts such as sodium salt and potassium salt, alkaline earth metal salts such as calcium salt and magnesium salt, organic base salts such as trimethylamine, triethylamine, pyridine, picoline, dicyclohexylamine, N,N'-dibenzylethylenediamine, arginine and lysine, and ammonium salt.

According to the present invention, the compound represented by Formula I or a pharmaceutically acceptable salt thereof may be an anhydride or may form a solvate such as a hydrate. The solvate may be either aqueous or nonaqueous. For a nonaqueous solvate, an alcohol (for example, methanol, ethanol, n-propanol), dimethylformamide or the like may be used. Furthermore, according to the present invention, the compound represented by Formula I may be either crystalline or amorphous, and may be a single crystal polymorph or a mixture of crystal polymorphs, if any.

The compound represented by Formula I can also be obtained by a known chemical synthesis or as a commercially available product.

2. Long-Term Memory Inducing Agent, and Pharmaceutical Composition and Functional Food for Treating Memory Disorder The present invention relates to a compound described herein, a pharmaceutically acceptable salt thereof and a solvate thereof, a pharmaceutical composition and use thereof. The long-term memory inducing agent, and the pharmaceutical composition and the functional food for treating a memory disorder of the present invention comprise the above-described compound represented by Formula I, a pharmaceutically acceptable salt thereof or a solvate thereof.

In one embodiment, the compound of the present invention is useful in inducing a long-term memory. Specifically, in one embodiment, the present invention provides a method for inducing a long-term memory in a subject in need thereof, the method comprising a step of administering an effective amount of the compound represented by Formula I, a pharmaceutically acceptable salt thereof or a solvate thereof to the subject in need thereof.

In another embodiment, the present invention provides a method for treating a memory disorder in a subject in need thereof, the method comprising a step of administering a therapeutically effective amount of the compound represented by Formula I, a pharmaceutically acceptable salt thereof or a solvate thereof to the subject.

In another embodiment, the present invention relates to a pharmaceutical composition comprising the compound represented by Formula I, a pharmaceutically acceptable salt thereof or a solvate thereof, and one or more types of pharmaceutically acceptable additives.

The compound of the present invention may be administered alone or may be administered as a composition (for example, a pharmaceutical composition). The amount of the active element (compound) combined with additives is generally an amount of the compound that results a therapeutic effect. A "pharmaceutical composition" contains a preparation that is appropriate to be administered to an animal or an insect, for example, a mammal animal, and a pharmaceutical composition of the embodiment contains the compound and a pharmaceutically acceptable additive. The compound of the present invention may be administered simultaneously with or before or after the administration of one or more types of other therapeutic agents.

According to the present invention, a "long-term memory" usually refers to a memory that is formed by repeated learning/training. Moreover, synthesis of a new protein is considered to imply induction of long-term memory. A "long-term memory" usually refers to a memory that persists for a day or longer, in some cases, for the lifetime. Accordingly, induction of a long-term memory may be recognized when the memory remains for 24 hours or longer.

On the other hand, a "short-term memory" usually refers to a memory that can be formed by single-time training but that is forgotten with time. A memory that is unaffected by administration of a protein synthesis inhibitor is judged to be a short-term memory.

A "memory disorder" refers to memory-related disorders in general that hinder recollection of own experience or things learned in the past, or that hinder learning new things. Exemplary forms of memory disorders include age-related memory disorders, Alzheimer-type dementia, cerebrovascular dementia, dementia with Lewy bodies and degeneration in the frontal or temporal lobe. These memory disorders are caused by emergence of at least one change selected from loss of neurons, reduction of nerve cells and dendrites, neurofibrillary degeneration, change in senile plaques and the like, and develop due to dementia and aging. Meanwhile, a learning/memory disorder is known to be caused due to various chronic diseases such as fatigue syndrome.

Herein, the term "treatment" refers to either recovery from memory disorder to a normal state or improvement in memory.

The phrase "effective amount" or "therapeutically effective amount" of the compound of the present invention refers to an amount of the compound of the present invention that can derive a biological response or a medical response of the subject, for example, that can induce, form or retain a long-term memory, that can synthesize protein, that can produce remission of the symptom, that can alleviate the condition, that can slow or delay progress of the disease or that can prevent the disease.

The term "subject" as used herein refers to an animal or an insect. For example, the long-term memory inducing agent, and the pharmaceutical composition and the functional food for treating memory disorder of the present invention may be administered or given to a mammal animal or an insect. For example, they may be used upon training a police dog/guide dog or upon training a dolphin or a companion animal. Besides human, examples of mammal animals (subjects) targeted for administration or feeding include, but not limited to, livestock such as a cow, a horse, a sheep and a goat, and companion animals such as a dog and a cat, and experimental animals such as a mouse, a rat, a guinea pig and a rabbit.

The dosage form of the long-term memory inducing agent, and the pharmaceutical composition and the functional food for treating a memory disorder of the present invention may be either oral or parenteral. For example, the above-described compound represented by Formula I, a pharmaceutically acceptable salt thereof or a solvate thereof, or a long-term memory inducing agent or a pharmaceutical composition containing the same may be administered or inhaled by the subject by oral administration, local administration, rectal administration, transdermal administration or parenteral injection.

In a specific embodiment, the above-described compound represented by Formula I, a pharmaceutically acceptable salt thereof or a solvate thereof, or a long-term memory inducing agent or a pharmaceutical composition comprising the same is orally administered. In the case of oral administration, it can be administered, for example, as a tablet, a capsule, granules, powder, a syrup or the like.

Examples in the case of parenteral administration include an injectable agent, a suppository, eye-drops, a transpulmonary dosage form (for example, using a nebulizer or the like), a transnasally administered dosage form, and a transdermally administered dosage form (for example, ointment, a cream agent, an aqueous solution, a suspension, a gel agent). In a case of an injectable dosage form, for example, it can be systemically or locally administered by intravenous injection such as drip infusion, intramuscular injection, intraperitoneal injection, subcutaneous injection or the like. In a specific embodiment, the above-described compound represented by Formula I, a pharmaceutically acceptable salt thereof or a solvate thereof, or a long-term memory inducing agent or a pharmaceutical composition comprising the same is transdermally administered. Examples of the transdermally administered dosage form include ointment, a cream agent, a gel agent, powder, a spray agent, a paste agent, a lotion agent, a solution agent, an adhesive patch and an inhaling agent. The transdermally administered dosage form may be applied to the skin, for example, as a solution agent, or applied to the skin, for example, as a skin adhesive patch.

These formulations can be produced by a well known method by using a pharmaceutically acceptable additive such as an excipient, a lubricant, a binder, a disintegrator, a stabilizer, a flavoring agent and a diluent.

Examples of the excipient include starch such as potato starch and corn starch, lactose, crystalline cellulose and calcium hydrogen phosphate.

Examples of the lubricant (coating agent) include ethyl cellulose, hydroxypropyl cellulose, hydroxypropyl methyl cellulose, shellac, talc, carnauba wax and paraffin.

Examples of the binder include polyvinyl pyrrolidone, macrogol and compounds similar to the above-mentioned excipients.

Examples of the disintegrator include compounds similar to the above-mentioned excipients, and chemically modified starch/cellulose such as croscarmellose sodium, sodium carboxymethyl starch and cross-linked polyvinyl pyrrolidone.

Examples of the stabilizer include para-oxybenzoates (for example, methylparaben, propylparaben, etc.), alcohols (chlorobutanol, benzyl alcohol, phenylethyl alcohol, etc.), benzalkonium chloride and phenols (phenol, cresol, etc.).

Examples of the flavoring agent include commonly used sweetener, acidulant and fragrance.

Furthermore, as a solvent used for producing a liquid agent, ethanol, phenol, chlorocresol, purified water, distilled water or the like can be used.

Examples of the surfactant and the emulsifier include Polysorbate 80, Polyoxyl 40 stearate and Lauromacrogol.

One or a combination of the above-mentioned additives and else are selected from those mentioned above according to the form of the agent. For example, in a case of an injectable formulation, a purified compound, a pharmaceutically acceptable salt thereof or a solvate thereof can be dissolved in a solvent (for example, a physiological saline, a buffer, a glucose solution, etc.), to which Tween 80, Tween 20, gelatin, human serum albumin or the like may be added. Alternatively, it may be freeze-dried so as to obtain a formulation that can be dissolved upon use. As an excipient for freeze dry, for example, a sugar alcohol or a sugar such as mannitol or glucose can be used.

A dosage of the compound of the present invention, when used as a long-term memory inducing agent or a pharmaceutical composition for treating a memory disorder, may vary depending on the age, the sex, the symptom, the administration route, the number of doses and the dosage form. An administration method can appropriately be selected according to the age and the symptom of the patient. For example, an effective dosage of melatonin is estimated to be about 4.1 µg-20.5 µg per kg of the body weight a day since about 3 µl of a solution containing 1.16 ng/µl compound was administered to a cricket with a body weight of about 850 mg a day (based on the results from administering 3 µl of 5 µM-25 µM). Meanwhile, an effective dosage of AMK is 0.03 µg/kg-4.16 µg/kg (based on the results from administering 3 µl of 40 nM-5 µM). The effective dosage, however, should not be limited to these dosages.

The functional food of the present invention can be ingested in any form. In one embodiment, the present invention is related to a method for inducing a long-term memory in a subject in need thereof, the method comprising a step of ingesting functional food containing the above-described compound represented by Formula I, a pharmaceutically acceptable salt thereof or a solvate thereof. In another embodiment, the present invention is related to a method for preventing or treating memory disorder in a subject in need thereof, the method comprising a step of ingesting functional food containing the above-described compound represented by Formula I, a pharmaceutically acceptable salt thereof or a solvate thereof.

For example, if the compound of the present invention is used as functional food, examples of the form thereof include a beverage, a dairy product, seasoning, noodles, processed livestock meat/fish meat food, margarine, bread and confectionery. While food of the present invention includes wide variety of forms and is not limited to the above-mentioned examples, it is preferably in a form of dietary supplement or health food in terms of prevention or treatment of memory disorder and retention of memory. The amount of the compound of the present invention added to the food is not particularly limited and may appropriately be determined. For example, the amount in 1 g of the food per kg of body weight is about 11.6 µg or more in the case of melatonin (based on the result from ingesting 5 µM for 10 µl) and about 2.32 µg or more in the case of AMK (based on the results from ingesting 1 µM for 10 µl).

Hereinafter, the present invention will be described in more detail by way of examples. The present invention, however, should not be limited to these examples.

In the following examples, young and aged crickets as well as young and aged mice were used to carry out olfactory associative learning tests and object recognition tests (ORT).

Example 1

Olfactory Associative Learning Test in Young or Aged Crickets

<Materials and Methods>
1.1. Experimental Animals
Male crickets about one week old (young) or three week old (aged) following molting into adult forms were used. Each of the crickets was placed into a 100 ml beaker three days before the experiment, and deprived of water for 2-3 days to enhance the desire of taking water. As the feed, about 10 pieces of insect feed were placed into the beaker.
1.2. Olfactory Associative Conditioning
A 1-ml syringe was used for smell and reward associative conditioning upon learning/training. The syringe contained water as the reward while a piece of paper (3 mm×3 mm) perfumed with peppermint essence was pierced into the needle to about 1 cm from the tip thereof. In this learning/training, the filter paper on the needle was brought near the antennae of the cricket to allow it to smell for 3 seconds and then a drop of water was put out from the tip of the needle and applied to the mouth of the cricket. When the associative conditioning was conducted for four times, the conditionings were conducted at intervals of 5 minutes.

1.3. Smell Preference Test
Smell preference was examined by placing each cricket into a test arena. The arena consisted of a "standby chamber" and a "test chamber". The floor of the "test chamber" had two holes each with a diameter of 4 cm which were communicated with two smell sources. The smell source was a plastic pot containing filter paper perfumed with essence of a smell (peppermint or vanilla) and covered with a gauze lid. In the preference test, each cricket was placed into the test chamber and allowed to walk freely for 4 minutes to search for the two smell sources. Two minutes after the start of the test, a rotary board having the smell sources was rotated to reverse the positions of the vanilla and the peppermint smells. During the test, the time the cricket spent placing its mouth to the gauze of the smell source was measured as a visiting time to the smell source, and the ratio of the visiting times of the two types of smells (PI value: preference index) was calculated according to the following formula to assess the relative preference to the mint smell.

$$PI\ value = Tp/(Tp+Tv) \times 100$$

Tp: Searching time for smell associated with the reward (peppermint)
Tv: Searching time for smell not associated with the reward (vanilla)

If the preferences for the two smells are equivalent, PI will be 50. Since crickets inherently prefer vanilla smell over peppermint smell, an average PI value prior to the learning/training is usually 25-35, The preference test was conducted before and after the learning/training to examine whether preference for the smell changes due to the learning/training.
1.4. Drug
As drugs, melatonin, N(1)-acetyl-N(2)-formyl-5-methoxykynuramine (AFMK), N(1)-acetyl-5-methoxykynuramine (AMK), 6-Hydroxymelatonin (6-HM), L-kynurenine, kynuramine, 8-Bromoguanoine 3',5'-cyclic monophosphate sodium salt (8 br-cGMP) and cycloheximide (CHX) were used. Melatonin, 6-HM, kynurenine, kynuramine and 8br-cGMP were purchased from SIGMA Aldrich, AFMK was purchased from Cayman Chemical, AMK was purchased from Toronto Research Chemicals and CHX was purchased from Wako Pure Chemical Industries. The drugs other than 8br-cGMP and CHX were first dissolved in ethanol and then diluted with physiological saline for crickets to the respective concentrations. In the administration experiment, 3 µl was administered using a 10-µl syringe to the brain via an aperture opened through a simple eye of the head.
1.5. Statistical Processing
PI values were tested before the training and a day after the training in the same group by a Wilcoxon's-test.
<Results>
1.1. Effect of Melatonin in Inducing Long-Term Memory
In order to examine the effect of melatonin in memory formation, crickets administered with melatonin in the brains received single-time training to examine the long-term memory after a day (FIG. 1). In the crickets administered with physiological saline in the brains as the control group, the PI value for mint a day after the training did not have significant difference from the PI value before the training whereas in the crickets administered with melatonin, the PI value a day after the training was significantly higher than the PI value before the training. Specifically, melatonin was found to form a memory a day later even with single-time training. In addition, since there was no significant difference between the PI value before the training and the PI value a day after the training in the crickets simultaneously administered with melatonin and cycloheximide, a memory induced with melatonin seemed to be a long-term memory that depend on protein synthesis.

1.2. Effects of Melatonin Metabolites

Figure 2A:
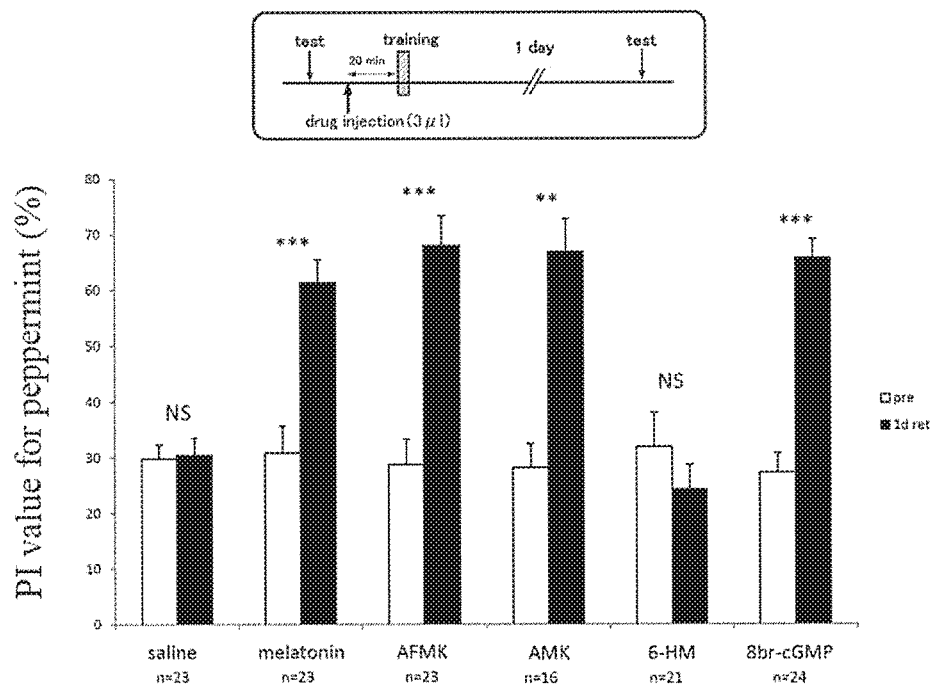
FIG. 2A A diagram showing effects of melatonin metabolites. In order to observe the effects of administering the melatonin metabolites, drugs were administered 20 minutes before the single-time training, followed by examination of a long-term memory. The administered drugs were physiological saline, melatonin (5 µM), AFMK (5 µM), AMK (5 µM), 6-HM (5 µM) and 8br-cGMP (200 µM), which were administered 3 µl each to the cricket brains, respectively.
Figure 2B:
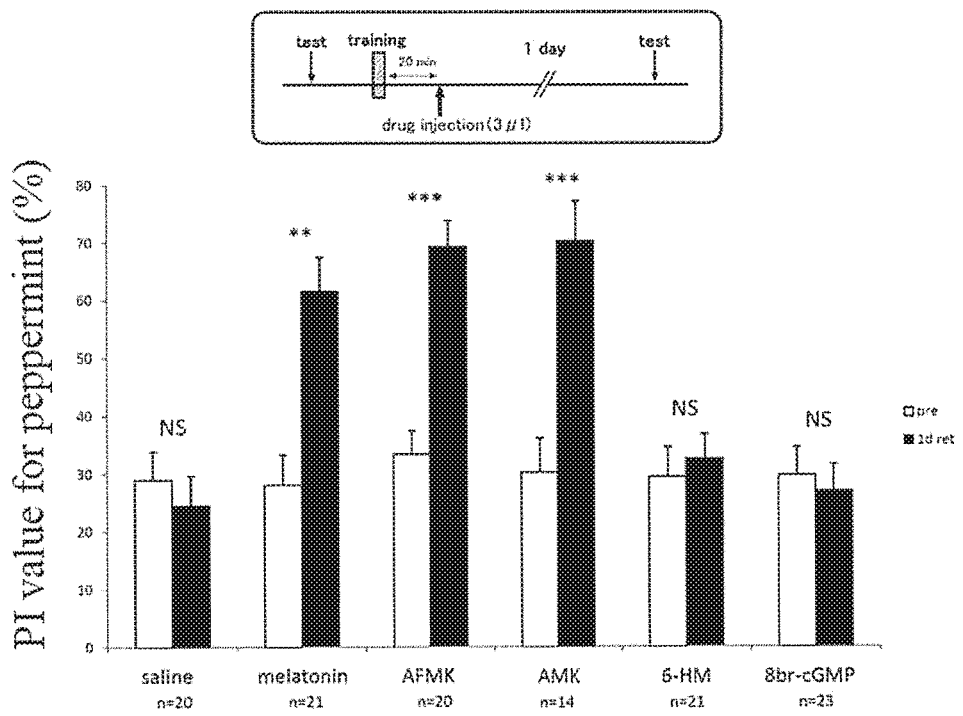
FIG. 2B A diagram showing effects of melatonin metabolites. In order to observe the effects of administering the melatonin metabolites, drugs were administered 20 minutes after the single-time training, followed by examination of a long-term memory. The administered drugs were physiological saline, melatonin (5 µM), AFMK (5 µM), AMK (5 µM), 6-HM (5 µM) and 8br-cGMP (200 µM), which were administered 3 µl each to the cricket brains, respectively.

Effects of melatonin metabolites on long-term memories were examined. Brain metabolites AFMK and AMK and a liver metabolite 6-HM of melatonin were administered to the brain and single-time training was conducted 20 minutes after the administration. While long-term memories were formed a day after the training in the AFMK administration group and the AMK administration group, a long-term memory was not formed in the 6-HM administration group (FIG. 2A). Specifically, AFMK and AMK had an effect of inducing a long-term memory like melatonin whereas 6-HM did not show an induction effect. Meanwhile, an effect of 8br-cGMP in inducing a long-term memory was confirmed as reported in the previous study. Next, effects of administering melatonin and melatonin metabolites after the training were examined (FIG. 2B).

Twenty minutes after the single-time training, melatonin, AFMK, AMK and 6-HM were administered to the brain. While long-term memories were formed a day after the training in the melatonin administration group, the AFMK administration group and the AMK administration group, a long-term memory was not formed in the 6-HM administration group. Specifically, melatonin, AFMK and AMK were found to have an effect of inducing a long-term memory even when administered after the training. On the other hand, 8br-cGMP did not have the effect of inducing long-term memory when administered after the training.

1.3. Effects of Kynuramine and Kynurenine

Figure 3:
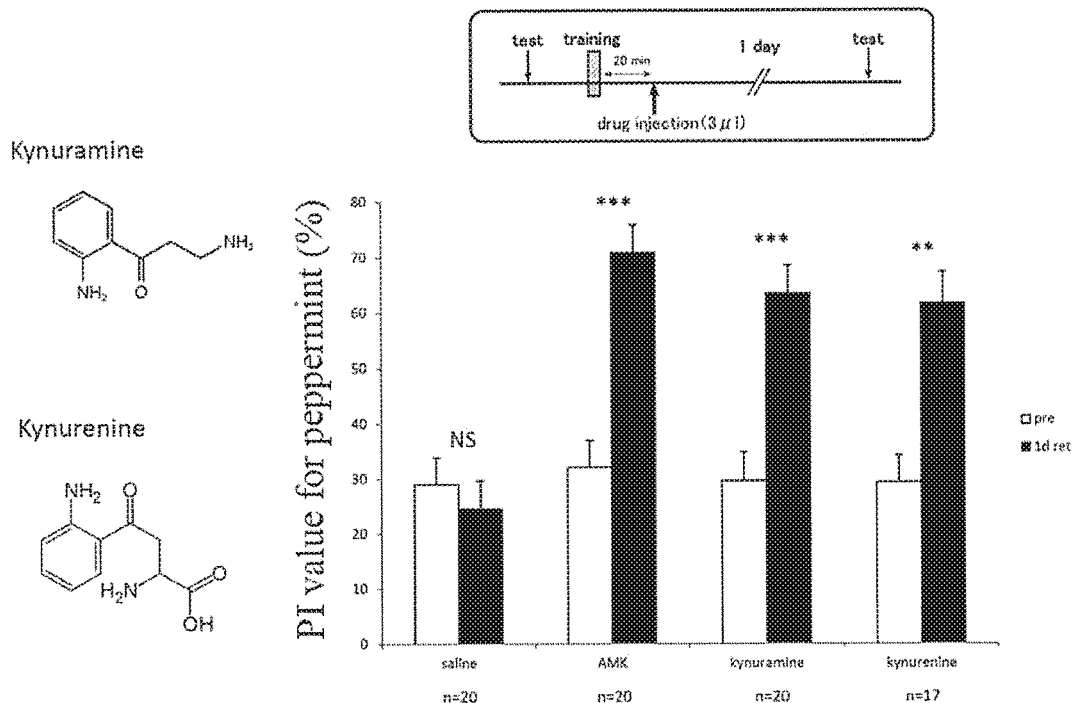
FIG. 3 A diagram showing effects of kynuramine and kynurenine, Kynuramine (5 µM) and kynurenine (5 µM) were administered to the brains 20 minutes after the single-time training, respectively. For comparison, the results of crickets administered with physiological saline and AMK (5 µM) are also shown. The structural formulae of kynuramine and kynurenine are shown on the left side of the graph.

Kynuramine and kynurenine have similar structures as AFMK, and AMK. When kynuramine or kynurenine was administered to the brain 20 minutes after single-time training to examine the effect of kynuramine and kynurenine on long-term memories, the long-term memories were formed a day after the training in both groups (FIG. 3). Specifically, kynuramine and kynurenine showed an effect of inducing a long-term memory when administered after the training like melatonin, AFMK and AMK.

1.4. Effects of Administration Concentrations

Figure 4A:
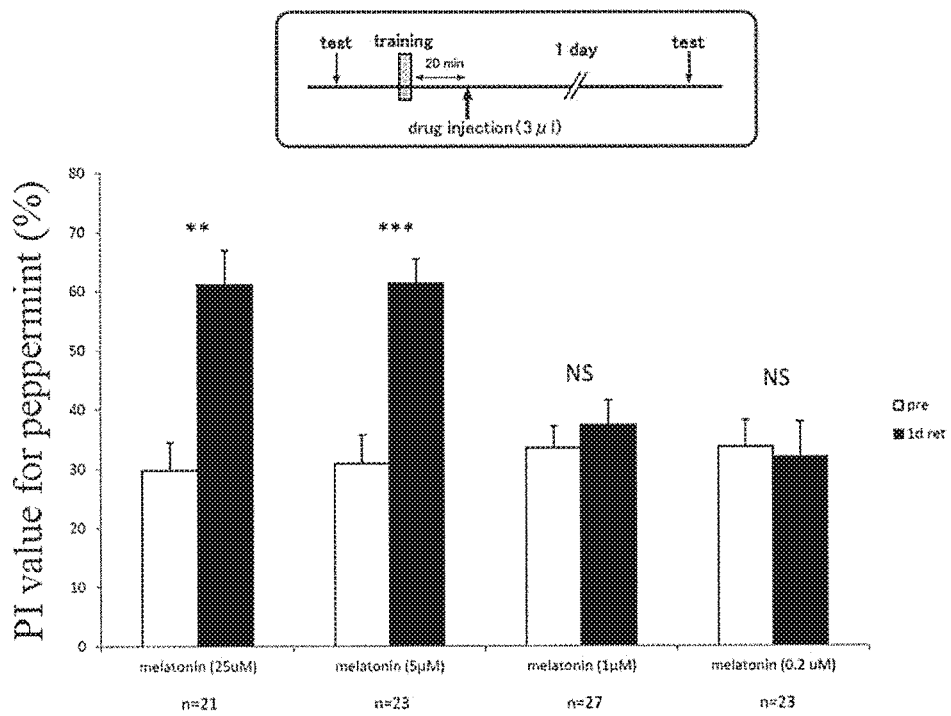
FIG. 4A A diagram showing effects of melatonin and melatonin metabolites according to administration concentrations. Concentration-dependent effects of melatonin were examined. Drugs were administered 20 minutes after the single-time training. 3 μl each of melatonins at concentrations of 25 μM, 5 μM, 1 μM and 0.2 μM were administered, respectively.
Figure 4B:
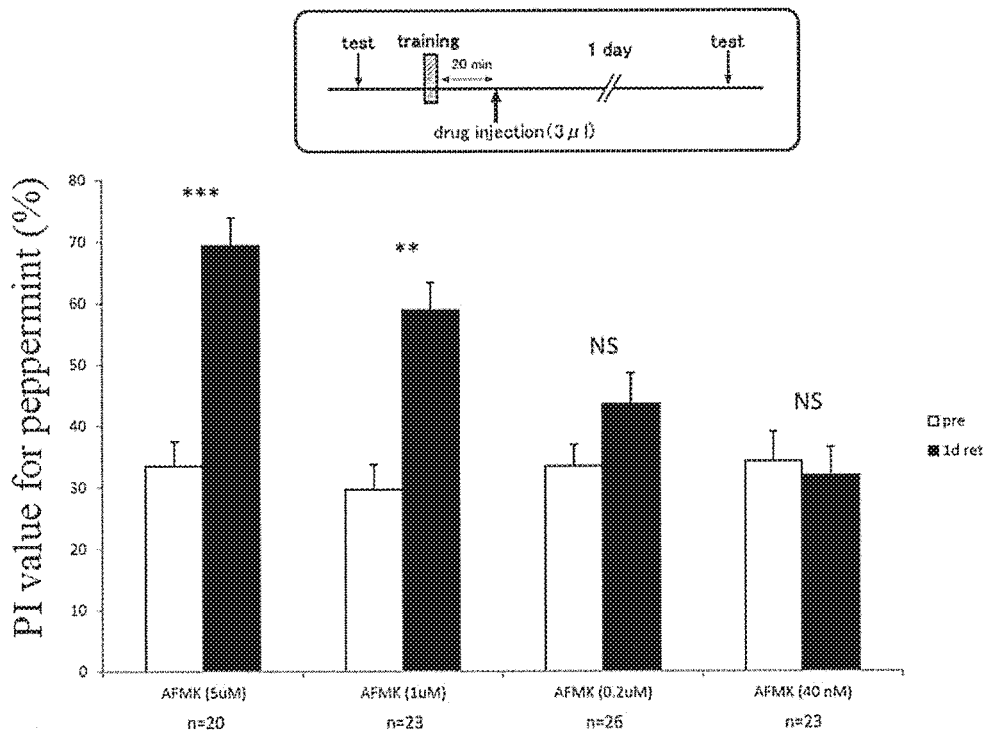
FIG. 4B A diagram showing effects of melatonin and melatonin metabolites according to administration concentrations. The concentration-dependent effects of AFMK were examined. The drugs were administered 20 minutes after the single-time training. 3 μl each of AFMK at concentrations of 5 μM, 1 μM, 0.2 μM and 40 nM were administered, respectively.
Figure 4C:
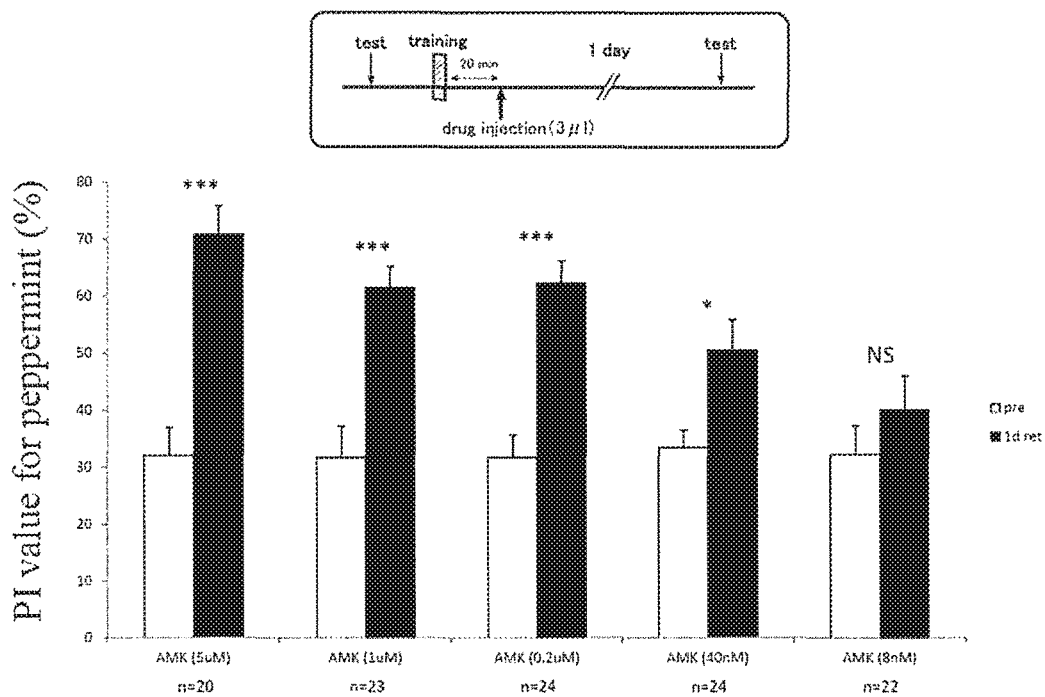
FIG. 4C A diagram showing effects of melatonin and melatonin metabolites according to administration concentrations. The concentration-dependent effects of AMK were examined. The drugs were administered 20 minutes after the single-time training. 3 μl each of AMK at concentrations of 5 μM, 1 μM, 0.2 μM, 40 nM and 8 nM were administered, respectively.

In order to observe concentration-dependent effects of melatonin and melatonin metabolites on formation of a long-term memory, 3 µl each of drugs at various concentrations was administered 20 minutes after single-time training to examine the memory a day after the training (FIG. 4). In the melatonin administration group, long-term memory was formed at concentrations of 25 µM and 5 µM but not at concentrations of 1 µM and 0.2 µM (FIG. 4A). In the AFMK administration group, long-term memories were formed at concentrations of 5 µM and 1 µM but not at concentrations of 0.2 µM and 40 nM (FIG. 4B). In the AMK administration group, long-term memory was formed at concentrations of 5 µM, 1 µM, 0.2 µM and 40 nM but not at a concentration of 8 nM (FIG. 4C). Specifically, among melatonin, AFMK and AMK, AMK was capable of inducing a long-term memory at the lowest concentration.

1.5. Effects of Administration Timings

Figure 5A:
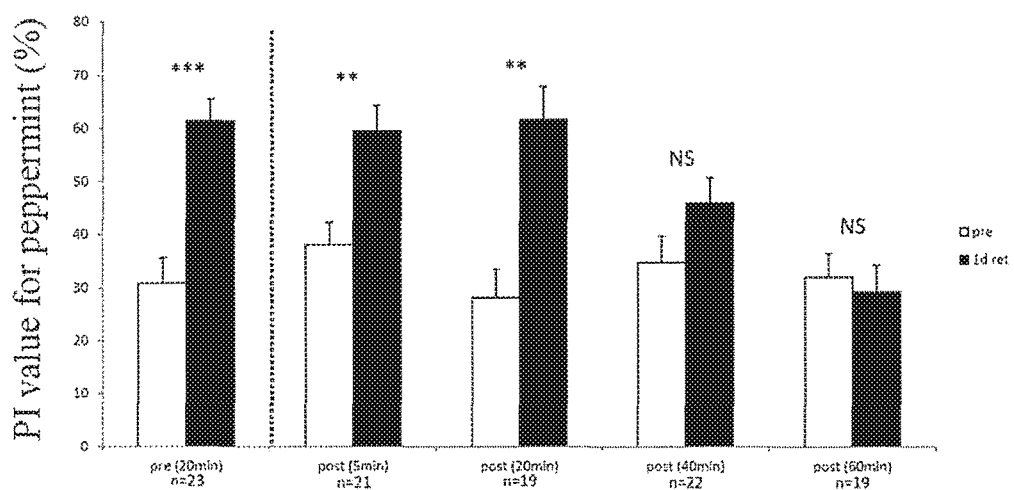
FIG. 5A A diagram showing effects of melatonin according to the timing of administration. The effects of melatonin and melatonin metabolites in inducing memory were examined according to difference in the timing of administration. 3 μl of melatonin at a concentration of 5 μM was administered at various timings before and after the single-time training, followed by examination of the memory a day after the training. The bars on the left side of the dotted line in the graph show the results of administration before the training while the bars on the right side show the results of administration after the training.
Figure 5B:
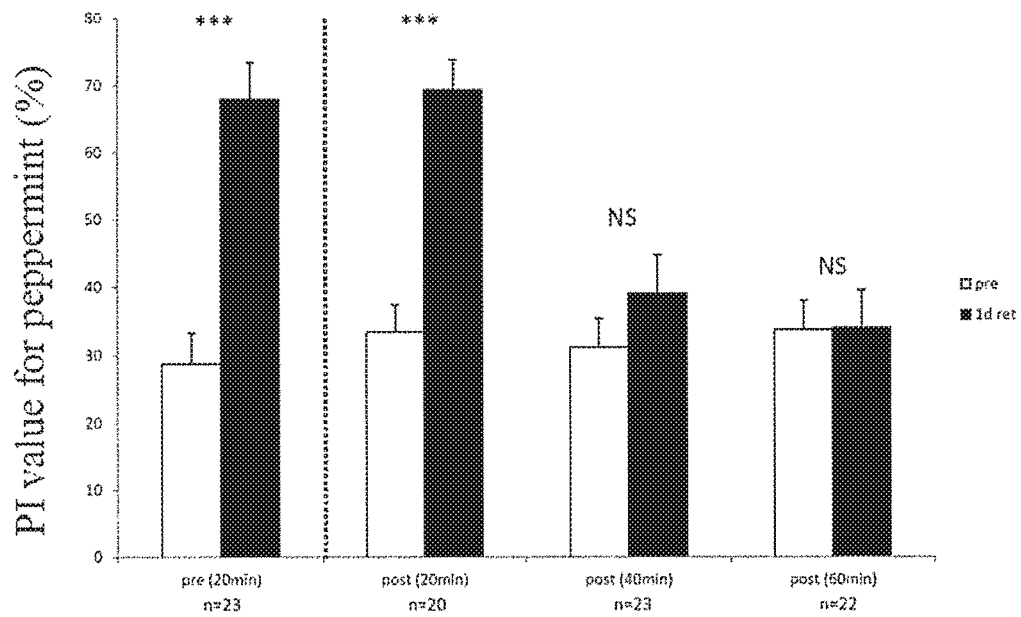
FIG. 5B A diagram showing effects of melatonin and melatonin metabolites according to the timing of administration. The effects of AFMK in inducing a memory were examined according to difference in the timing of administration. 3 μl of AFMK at a concentration of 5 μM was administered at various timings before and after the single-time training followed by examination of the memory a day after the training. The bars on the left side of the dotted line in the graph show the results of administration before the training while the bars on the right side show the results of administration after the training.
Figure 5C:
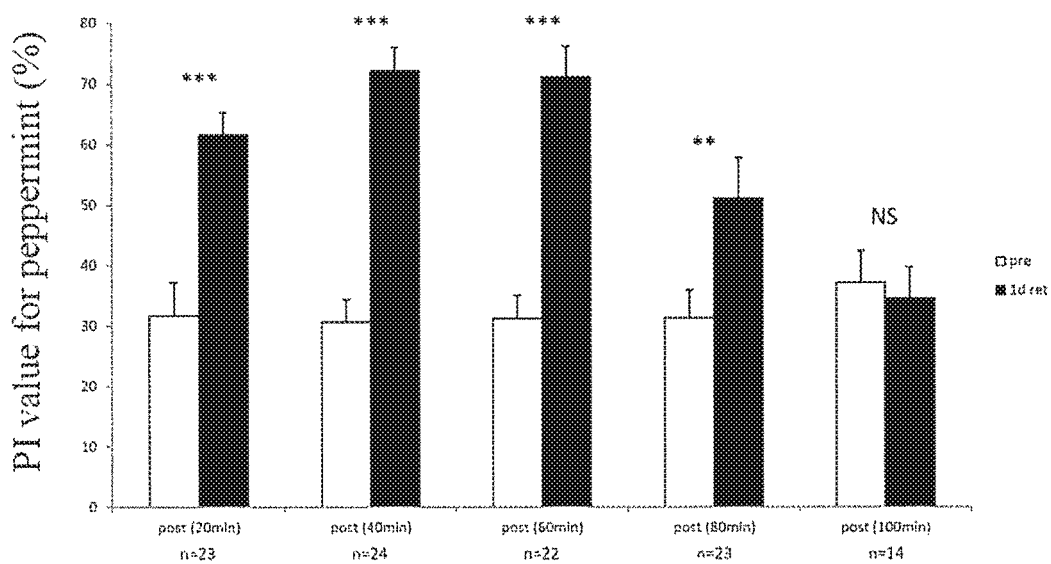
FIG. 5C A diagram showing effects of melatonin and melatonin metabolites according to the timing of administration. The effects of AMK in inducing a memory were examined according to difference in the timing of administration. 3 μl of AMK at a concentration of 1 μM was administered at various timings after the single-time training, followed by examination of the memory a day after the training.

In order to examine the effects of inducing a memory according to the difference in the timings of administering melatonin and melatonin metabolites, drugs were administered at various timings before and after single-time training to examine the memory a day after the training (FIG. 5). In the melatonin administration group (FIG. 5A) and the AFMK administration group (FIG. 5B), long-term memory was formed when administered between 20 minutes before the training and 20 minutes after the training but was not formed when administered 40 and 60 minutes after the training. Meanwhile, in the AMK administration group, a long-term memory was formed when administered between 20 minutes after the training and 80 minutes after the training but was not formed when administered 100 minutes after the training (FIG. 5C). Specifically, among melatonin, AFMK and AMK, AMK was found to induce long-term memory by administration at the furthest time point from the training.

6. Effect of Inducing Long-Term Memory by Oral Administration

Figure 6:
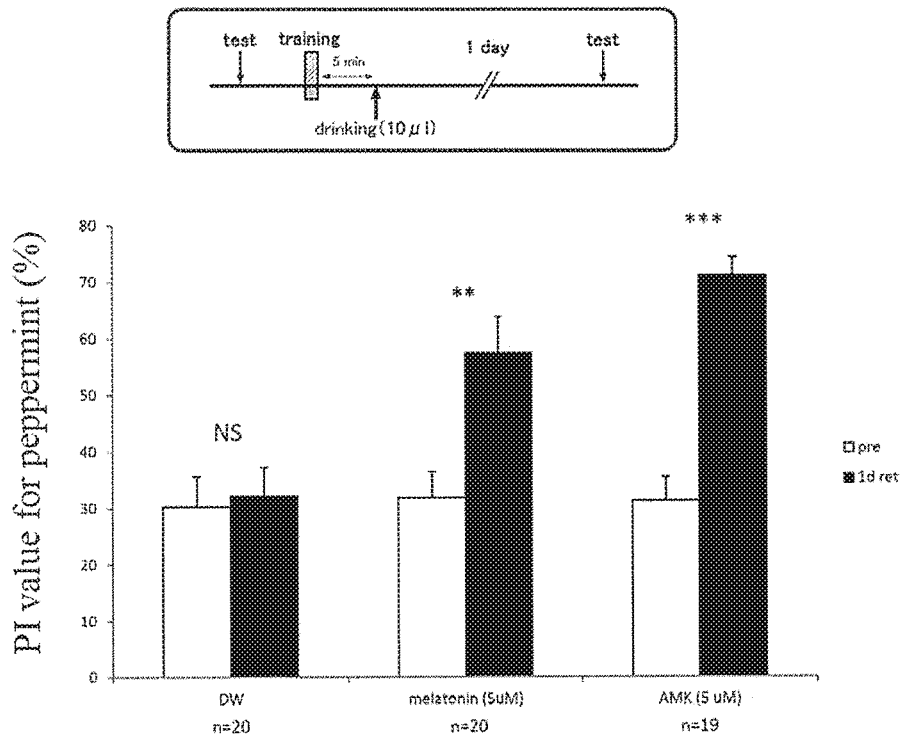
FIG. 6 A diagram showing effects of an aqueous solution of melatonin or AMK in inducing a long-term memory by oral administration. The aqueous melatonin solution (5 μM) or the aqueous AMK solution (5 μM) was applied to the mouth of the cricket 5 minutes after the single-time training to let them drink for 10 μl, followed by examination of the memory a day after the training. The control group (DW) was made to drink the same amount of distilled water.

In order to confirm whether or not AMK acts to induce a long-term memory by oral administration after single-time training, crickets were made to drink 10 µl of an aqueous melatonin solution (5 µM) or an aqueous AMK solution (5 µM) 5 minutes after the single-time training to examine the memory a day after the training (FIG. 6). In the control group that was made to drink distilled water, long-term memory was not formed whereas long-term memory was formed in the crickets that were made to drink melatonin water or AMK water. Specifically, melatonin and AMK were found to have the effect of inducing long-term memory even by oral administration.

1.7. Effects of Melatonin and AMK in Improving Age-Related Memory Disorder

Figure 7:
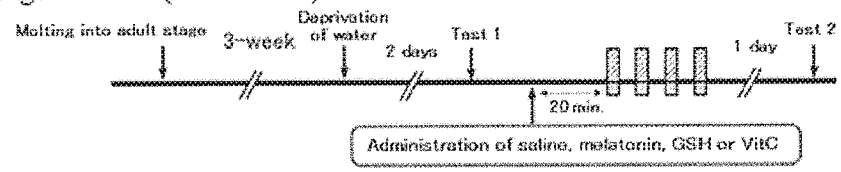
FIG. 7 A diagram showing effects of a melatonin-related substance in improving an age-related memory disorder by administration before the training. 3 μl of physiological saline, melatonin (5 μM), AMK (1 μM), glutathione (GSH: 500 μM) or vitamin C (Vit C: 500 μM) was administered to aged crickets three week old following molting into their adult stage, and 20 minutes later, training was conducted for four times. Tests took place before and a day after the training.
Figure 7:
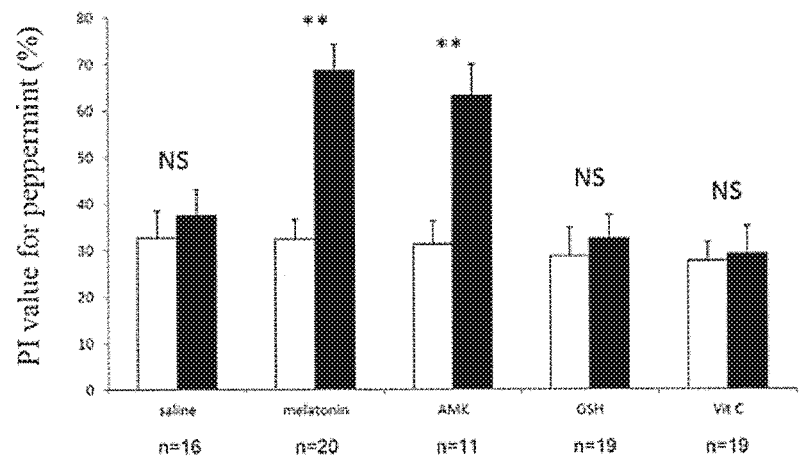

In order to examine whether or not melatonin and AMK could improve an age-related memory disorder, aged crickets three week old following molting into their adult stage were administered with melatonin or AMK and received training for four times before testing their memory a day later (FIG. 7). Crickets administered with physiological saline as a control group did not show memory a day after the 4-time training. Specifically, it was found that a long-term memory was not formed in aged crickets (age-related memory disorder). On the other hand, a long-term memory was formed in crickets administered with melatonin or AMK. These results show that melatonin and AMK improved an age-related memory disorder. Furthermore, no improvement in an age-related memory disorder was seen with glutathione and vitamin C that are known as antioxidants. From these results, the effects of melatonin and AMK in improving an age-related memory disorder seemed to be ascribed to a function apart from the antioxidant action of melatonin and AMK.

Figure 8:
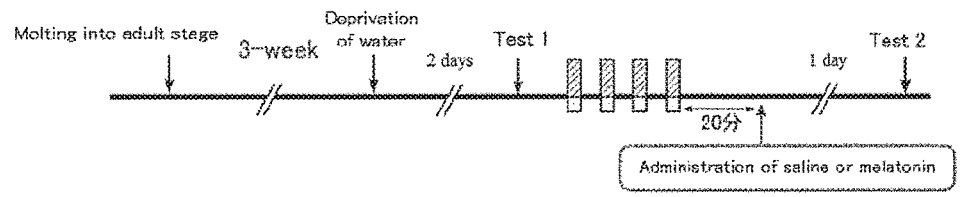
FIG. 8 A diagram showing effects of melatonin-related substances in improving an age-related memory disorder by administration after the training. Aged crickets were trained for four times, and 20 minutes later, 3 μl of physiological saline, melatonin (5 μM) or AMK (1 μM) was administered. Tests took place before and a day after the training.
Figure 8:
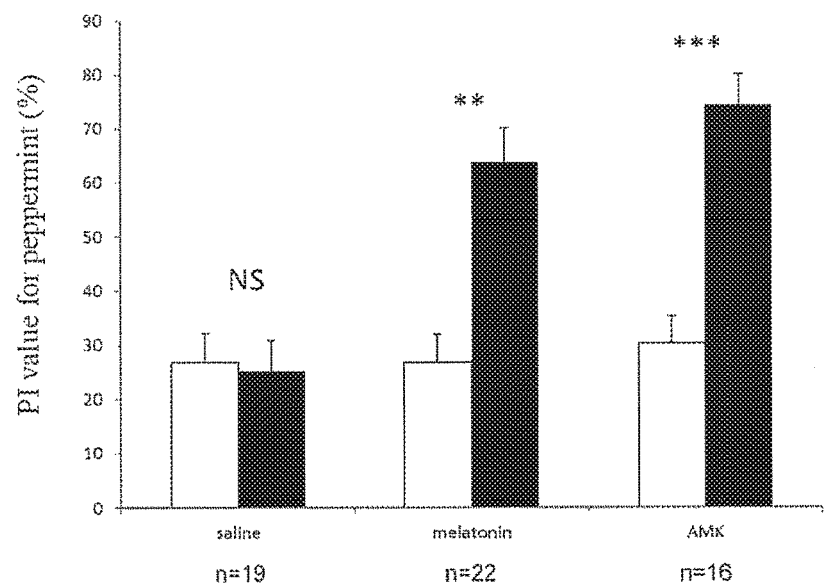

In addition, other crickets were administered with melatonin or AMK 20 minutes after the training in order to confirm the difference in the effects according to variation in the timings of administering the drugs. Similar to the group administered before the training, improvement in an age-related memory disorder was observed (FIG. 8).

<Discussion>

This example showed that melatonin and metabolites thereof, i.e., AFMK and AMK, especially AMK were important for the formation of a long-term memory. The facts that AMK was involved in memory formation and that extrinsically administered AMK could enhance a memory were results obtained for the first time in a learning/memory experiment system in animal species.

In this example, when crickets one week old following molting into their adult stage were administered with melatonin before the training, a long-term memory dependent on protein synthesis was formed even by single-time learning/training. In addition, similar long-term memory inducing effects were also observed with melatonin metabolites AFMK and AMK. Furthermore, the effects of melatonin, AFMK and AMK in inducing long-term memory were also observed by administration after single-time training.

In the previous study, the present inventors have reported a number of drugs that had the effect of inducing a long-term memory when administered before learning/training (Name of document: Learning and Memory, 2006). They were drugs that stimulated the nitrogen monoxide (NO)-cGMP signal transduction system or the cAMP signal transduction system. Specifically, in addition to 8br-cGMP used this time, they were NO donors (SNAP and NOR-3), a cAMP analog (8br-cAMP), a calcium ionophore, an adenylyl cyclase activator, a phosphodiesterase inhibitor and the like.

It is, however, for the first time to find that melatonin, AFMK and AMK have the effect of promoting the formation of a long-term memory even when the drug was administered after the learning/training. The effect of enhancing a memory by administration after the learning/training means that they could be prospective drugs.

In a living body, a part of melatonin is metabolized into AFMK and AMK in the brain, and a large part of melatonin is known to be metabolized into 6-hydroxymelatonin (6-HM) in the liver. In this experiment, 6-HM did not have the effect of inducing a long-term memory. On the other hand, kynurenine and kynuramine that are not metabolites of melatonin but that have similar structures as AFMK and AMK showed the effect of inducing a long-term memory when administered after the training. In the process of forming a long-term memory, melatonin does not act directly but rather it is important that melatonin is metabolized into metabolites, especially AMK, in the brain which act directly.

The results from the experiment of examining concentrations of drugs that induce a long-term memory also indicated that AMK was important than melatonin or AFMK. In this example, the administration concentration sufficient to form long-term memory was 5 µM for melatonin and 1 µM for AFMK whereas it was 40 nM for AMK (1/125 the concentration of melatonin). Moreover, from the experiment of administration timing, the timing of administration sufficient to form long-term memory was up to 20 minutes following the training for melatonin and AFMK whereas it was up to 80 minutes following the training for AMK. Accordingly, AMK can act even after a long period of time after the training.

Surprisingly, the results obtained in this example showed that a long-term memory was induced by administration even 80 minutes after the training. Since the average lifetime of crickets is about 2 weeks following molting into their adult stage, 80 minutes for crickets means several hours to several days for human.

In this example, both melatonin and AMK showed the effects of inducing a long-term memory by oral administration. Accordingly, melatonin and AMK are both effective as supplements.

Long-term memory was also formed in aged crickets when melatonin or AMK was administered before the training and when AMK was administered once after the training. From the previous study by the present inventors, it was found that although the levels of formation of a short-term memory and recall of a long-term memory in the aged crickets were the same as those of the young crickets, a long-term memory was not formed in the aged crickets at all.

So far, there has been no report of the effect of improving an age-related memory disorder by single-dose administration of melatonin to an aged individual like this time. In addition, there has been no report so far saying that AMK has an effect of recovering an age-related memory disorder. The effect of melatonin on age-related memory disorder seems to result not from the protective effect of the living body at a cellular/molecular level by antioxidant action as conventionally considered but from the effect of normalizing the memory formation mechanism that deteriorates with aged. The results obtained this time may be interpreted that administration of melatonin or AMK can temporary supply AMK to the aged brain, by which the long-term memory forming ability can be recovered.

Example 2

Synthesis of Derivatives of Melatonin Metabolites

The following Compounds 1-14 were synthesized as derivatives of melatonin metabolites according to the following schemes.

(Compounds 1-14)

[Chemical Formula 22]

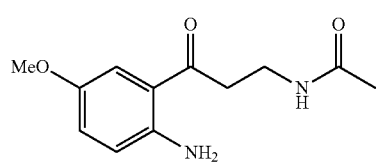

Compound 1

Chemical Formula: $C_{12}H_{16}N_2O_3$
Exact Mass: 236.12
Molecular Weight: 236.27

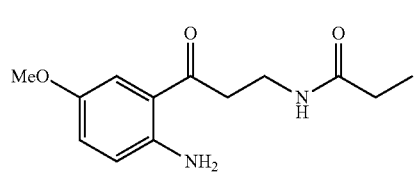

Compound 2

Chemical Formula: $C_{13}H_{18}N_2O_3$
Exact Mass: 250.13
Molecular Weight: 250.30

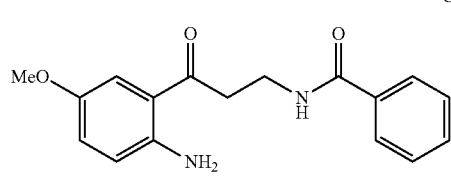

Compound 3

Chemical Formula: $C_{17}H_{18}N_2O_3$
Exact Mass: 298.13
Molecular Weight: 298.34

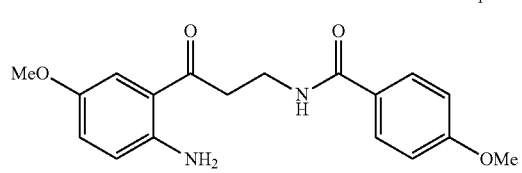

Compound 4

Chemical Formula: $C_{18}H_{20}N_2O_4$
Exact Mass: 328.14231
Molecular Weight: 328.36800

Compound 5

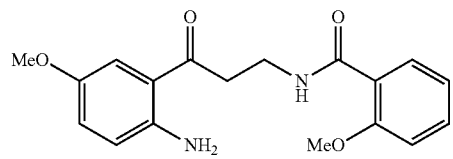

Chemical Formula: $C_{18}H_{20}N_2O_4$
Exact Mass: 328.14231
Molecular Weight: 328.36800

Compound 6

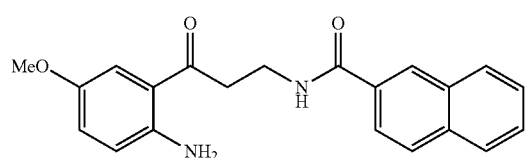

Chemical Formula: $C_{21}H_{20}N_2O_3$
Exact Mass: 348.14739
Molecular Weight: 348.40200

Compound 7

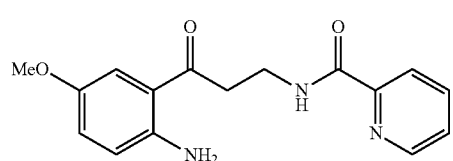

Chemical Formula: $C_{16}H_{17}N_3O_3$
Exact Mass: 299.12699
Molecular Weight: 299.33000

Compound 8

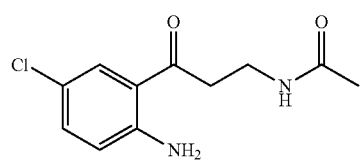

Chemical Formula: $C_{11}H_{13}ClN_2O_2$
Exact Mass: 240.07
Molecular Weight: 240.69

Compound 9

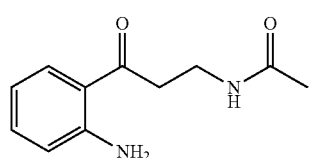

Chemical Formula: $C_{11}H_{14}N_2O_2$
Exact Mass: 206.11
Molecular Weight: 206.24

Compound 10

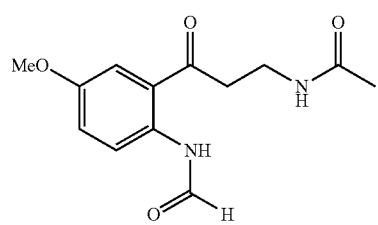

Chemical Formula: $C_{13}H_{16}N_2O_4$
Exact Mass: 264.11
Molecular Weight: 264.28

Compound 11

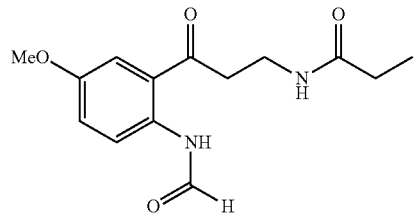

Chemical Formula: $C_{14}H_{18}N_2O_4$
Exact Mass: 278.13
Molecular Weight: 278.31

Compound 12

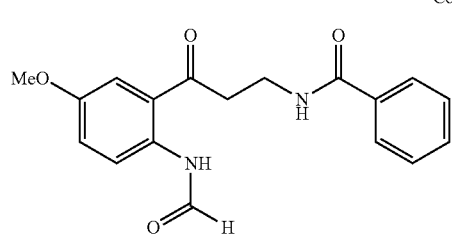

Chemical Formula: $C_{18}H_{18}N_2O_4$
Exact Mass: 326.13
Molecular Weight: 326.35

Compound 13

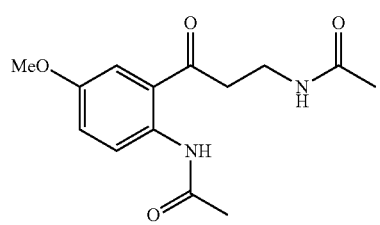

Chemical Formula: $C_{14}H_{18}N_2O_4$
Exact Mass: 278.13
Molecular Weight: 278.31

Compound 14

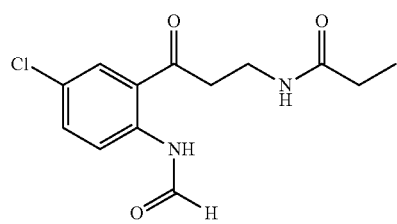

Chemical Formula: $C_{12}H_{13}ClN_2O_3$
Exact Mass: 268.06
Molecular Weight: 268.70

(Schemes for Synthesizing Compounds)

[Chemical formula 23]

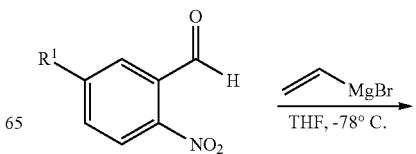

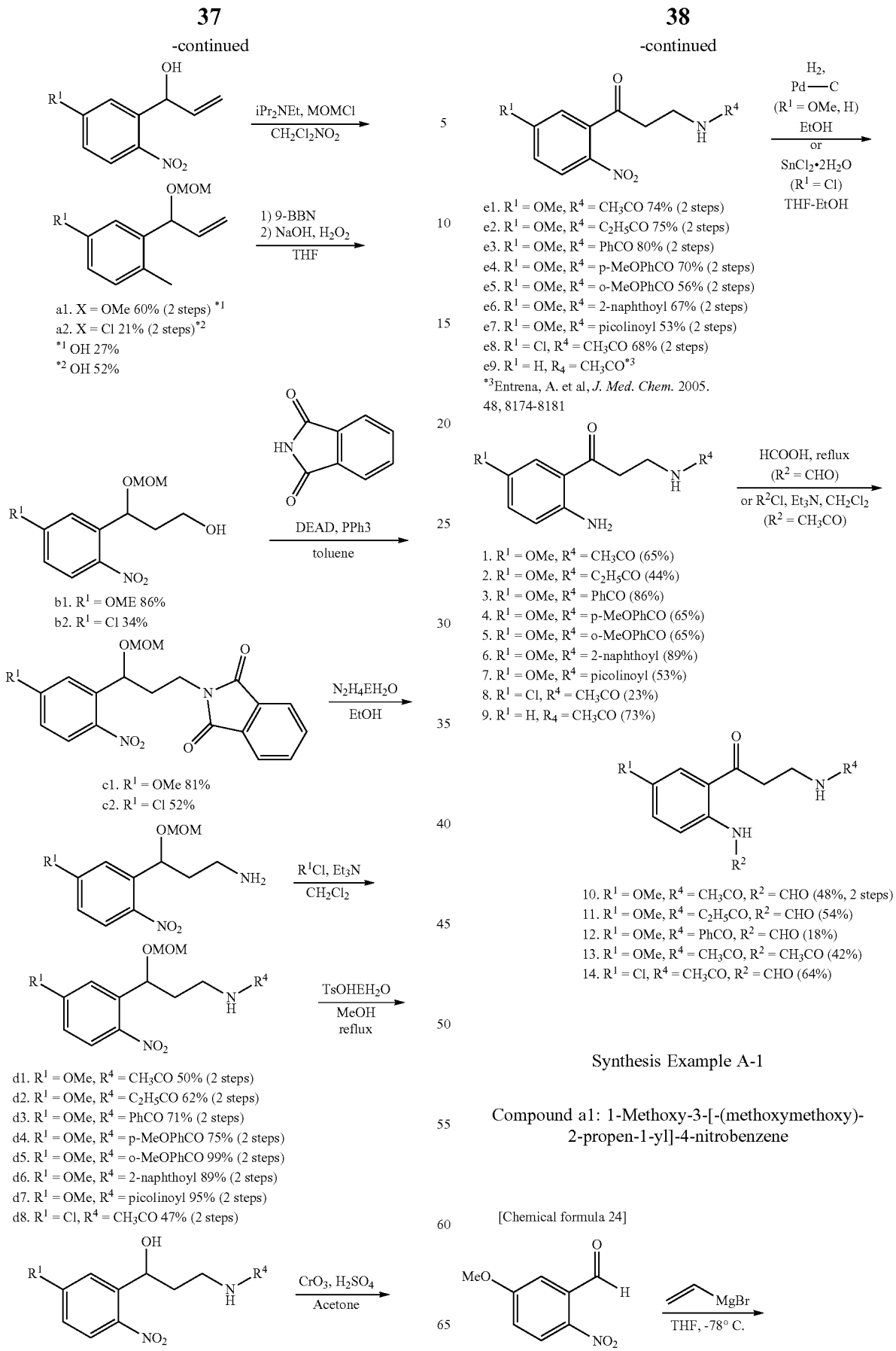
Synthesis Example A-1
Compound a1: 1-Methoxy-3-[-(methoxymethoxy)-2-propen-1-yl]-4-nitrobenzene
[Chemical formula 24]

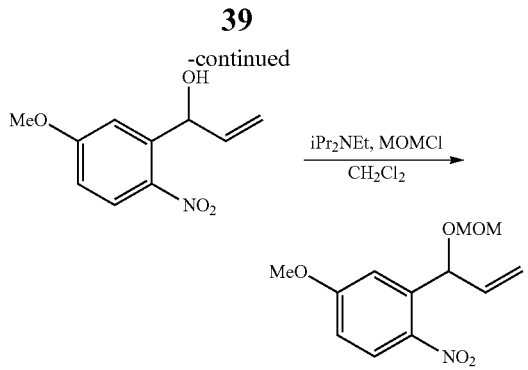

A vinylmagnesium chloride solution (1 M in THF, 5.9 mL) was added dropwise to a solution of 2-nitro-5-methoxybenzaldehyde (890 mg, 4.91 mmol) in THF (9 at −78° C. The resulting solution was stirred at that temperature for 2.5 hours. The reaction mixture was quenched with a 0.02 M aqueous HCl solution. The mixture was acidified with a 2M aqueous HCl solution, and subjected to extraction with ether. The organic layer was washed with brine and dried with $Na_2SO_4$. The desiccant was removed before the solvent was evaporated. The resulting crude alcohol was dissolved in 10 mL of $CH_2Cl_2$. Diisopropyl ethyl amine (2.5 mL, 14.7 mmol) and chloromethyl methyl ether (740 μL, 9.8 mmol) were added to that solution and stirred at room temperature for 13 hours. A saturated aqueous sodium bicarbonate solution was added to the reaction mixture, and the resultant was subjected to extraction with $CH_2Cl_2$. The organic layer was washed with water and dried with $Na_2SO_4$. The desiccant was removed before the solvent was evaporated. The residue was chromatographed on silica gel (10% to 40% AcOEt/hexane) to give 740 mg (60%) of methoxymethyl ether and 277 mg (27%) of secondary alcohol (title compound).

Light yellow oil. $^1$H-NMR (400 MHz, $CDCl_3$, δ) 3.35 (3H, s), 3.90 (3H, s), 4.62 (1H, d, J=6.7 Hz), 4.75 (1H, d, 1=6.6 Hz), 5.21-5.23 (1H, m), 5.34-5.38 (1H, m), 5.92-5.99 (2H, m), 6.87 (1H, dd, J=2.7 Hz, 9.1 Hz), 7.27 (1H, d, 1=2.9 Hz), 8.05 (1H, d, J=9.1 Hz). $^{13}$C-NMR (125 MHz, $CDCl_3$, δ) 55.8, 55.9, 73.3, 94.6, 113.0, 113.2, 117.0, 127.4, 136.5, 140.0, 141.1, 163.6. HRMS (ESI) calcd for $C_{12}H_{15}NNaO_5^+$ ([M+Na]$^+$): 276.0842, found: 276.0836.

Synthesis Example A-2

Compound a2: 5-chloro-1-[(methoxymethoxy)-2propen-1-yl]-2-nitrobenzene

[Chemical formula 25]

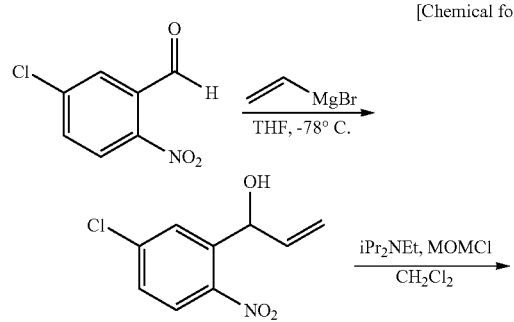

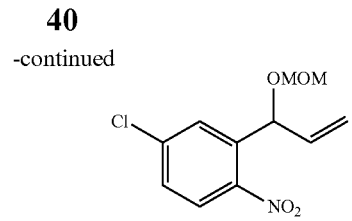

A THF solution (10 mL) of 5-chloro-2-nitrobenzaldehyde (1.04 g, 5.6 mmol) and a vinylmagnesium bromide solution (1 M in THF, 6.7 ml), then diisopropyl ethyl amine (2.9 mL, 16.8 mmol) and chloromethyl methyl ether (845 μL, 11.2 mmol) in $CH_2Cl_2$ (10 mL) were applied in the same manner as the methoxy product. The resulting crude product was chromatographed on silica gel (5% to 40% AcOEt/hexane) to give 329 mg (21%) of methoxymethyl ether and 628 mg (52%) of secondary alcohol (title compound).

Brown oil. $^1$H-NMR (400 MHz, $CDCl_3$, δ) 4.61 (1H, d, J=6.7 Hz), 4.76 (1H, d, J=6.7 Hz), 5.26 (1H, td, J=1.2 Hz, 10.3 Hz), 5.39 (1H, td, J=1.2 Hz, 17.1 Hz), 5.80 (1H, d, J=6.2 Hz), 5.91 (1H, ddd, J=6.1 Hz, 10.4 Hz, 17.0 Hz), 7.39 (1H, dd, J=2.4 Hz, 8.7 Hz), 7.78 (1H, d, J=2.3 Hz), 7.90 (1H, d, J=8.7 Hz). $^{13}$C-NMR (125 MHz, $CDCl_3$, δ) 55.9, 73.0, 94.6, 117.9, 126.0, 128.4, 128.8, 135.8, 138.7, 140.0, 146.3. HRMS (ESI) calcd for $C_{11}H_{12}ClNNaO_4^+$ ([M+Na]$^+$): 280.0347, found: 280.0347.

Synthesis Example B-1

Compound b1: 3-(2-nitro-5-methoxyphenyl)-3-methoxymethylpropanol

[Chemical formula 26]

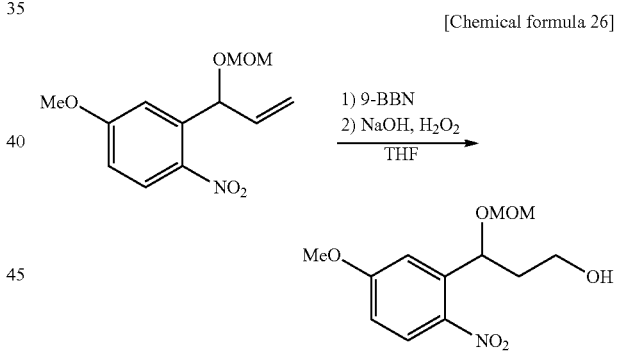

To a solution of MOM ether (Compound a1) (605 mg, 2.39 mmol) in THF (6 mL), a 9-BBN solution (0.5 M in THF, 7.2 mL) was added dropwise at 0° C. The resulting solution was stirred for 2.5 hours. A 3M aqueous NaOH solution (5 mL) and a 30% aqueous $H_2O_2$ solution (5 mL) were added to the reaction mixture at 0° C., and stirred at room temperature for 4 hours. Water was added to the reaction mixture, and the resultant was subjected to extraction with AcOEt. The organic layer was washed with brine and dried with $Na_2SO_4$. After $Na_2SO_4$ was removed, the solvent was removed under reduced pressure. The residue was chromatographed on silica gel (30% to 50% AcOEt/hexane) to give 548 mg (85%) of alcohol (title compound). The product was recrystallized from toluene and hexane.

Pale yellow powder. mp 83.5-84.5° C. $^1$H-NMR (400 MHz, $CDCl_3$, δ) 1.95 (1H, ddt, J=5.4 Hz, 9.2 Hz, 14.6 Hz), 2.17 (1H, ddt, J=3.1 Hz, 6.2 Hz, 14.7 Hz), 3.38 (3H, s), 3.88 (2H, dd, J=5.3 Hz, 6.2 Hz), 3.91 (3H, s), 4.49 (1H, d, J=6.7

Hz), 4.61 (1H, d, J=6.6 Hz), 5.59 (1H, dd, J=3.1 Hz, 9.1 Hz), 6.88 (1H, dd, J=2.9 Hz, 9.1 Hz), 7.25 (1H, d, J=2.8 Hz), 8.1 (1H, d, J=9.1 Hz). $^{13}$C-NMR (125 MHz, CDCl$_3$, δ) 9.9, 55.9, 56.0, 56.2, 60.6, 73.0, 73.0, 95.4, 112.8, 113.2, 127.7, 140.9, 141.7, 163.8. HRMS (ESI) calcd for $C_{12}H_{17}NNaO_6^+$ ([M+Na]$^+$): 294.0948, found: 294.0942.

Synthesis Example B-2

Compound b2:
3-(5-chloro-2-nitrophenyl)-3-methoxymethylpropanol

[Chemical formula 27]

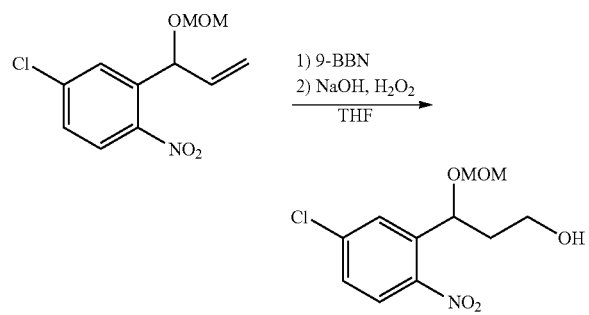

A 9-BBN solution (0.5 M in THF, 7.6 mL), MOM ether (Compound a2) (650 mg, 2.53 mmol) in THF (5 mL), a 3M aqueous NaOH solution (5 mL) and a 30% aqueous H2O2 solution were treated in the same manner as the methoxy compound. The crude product was chromatographed on silica gel (30% to 40% AcOEt/hexane) to give 417 mg (60%) of an alcohol of interest (title compound). The product was recrystallized from toluene and hexane.

Yellow powder. mp 58.5-60.5° C. $^1$H-NMR (400 MHz, CDCl$_3$, δ) 1.96 (1H, tdd, J=5.2 Hz, 9.3 Hz, 14.5 Hz), 2.14 (1H, dddd, J=3.3 Hz, 5.7 Hz, 6.9 Hz, 14.5 Hz), 3.36 (3H, s), 3.85-3.88 (2H, m), 4.49 (1H, d, J=6.8 Hz), 4.62 (1H, d, J=6.8 Hz), 5.45 (1H, dd, J=3.2 Hz, 9.2 Hz), 7.40 (1H, dd, J=2.3 Hz, 8.7 Hz), 7.77 (1H, d, J=2.4 Hz), 7.94 (1H, d, J=8.7 Hz). $^{13}$C-NMR (125 MHz, CDCl$_3$, δ) 39.9, 56.2, 60.2, 72.4, 95.6, 126.2, 128.5, 128.6, 140.3, 140.6, 146.2. HRMS (ESI) calcd for $C_{11}H_{14}ClNNaO_5^+$ ([M+Na]$^+$): 298.0453, found: 298.0445.

Synthesis Example C-1

Compound c1: N-[3-(2-nitro-5-methoxyphenyl)-3-methoxymethylpropyl]phthalimide

[Chemical formula 28]

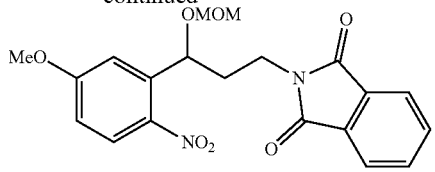

A diethyl azodicarboxylate solution (40%, ca. 2.2 M in toluene, 1.0 mL) was added to a solution of triphenylphosphine (620 mg, 2.37 mmol), phthalimide (341 mg, 2.32 mmol) and Compound b1, i.e., the alcohol, (422 mg, 1.56 mmol) in toluene (6 mL), and stirred at room temperature for 4 hours. Water was added to the reaction mixture, and the resultant was subjected to extraction with AcOEt. The organic layer was washed with water, washed with brine and dried with Na2SO4. After Na$_2$SO4 was removed, the solvent was removed under reduced pressure. The residue was chromatographed on silica gel (30% AcOEt/hexane) to give 321 mg (51%) of a phthalimide derivative (title compound). This product was recrystallized from EtOH.

Pale yellow needles. mp 138.0-139.0° C. $^1$H-NMR (400 MHz, CDCl$_3$, δ) 2.03 (1H, dddd, J=5.5 Hz, 5.7 Hz, 8.7 Hz, 14.4 Hz), 2.26 (1H, dddd, J=2.2 Hz, 6.3 Hz, 8.4 Hz, 14.5 Hz), 3.37 (3H, s), 3.87 (1H, ddd, J=5.4 Hz, 6.1 Hz, 13.4 Hz), 3.9 (3H, s), 4.1 (1H, ddd, J=5.9 Hz, 8.2 Hz, 14.0 Hz), 4.58 (1H, d, J=6.6 Hz), 4.70 (1H, d, J=6.6 Hz), 5.33 (1H, dd, J=2.3 Hz, 9.0 Hz), 6.83 (1H, dd, J=2.9 Hz, 9.1 Hz), 7.28 (1H, d, J=2.8 Hz), 7.71 (2H, dd, J=3.0 Hz, 5.4 Hz), 7.85 (2H, dd, J=3.0, 5.5 Hz), 8.04 (1H, d, J=9.1 Hz). $^{13}$C-NMR (125 MHz, CDCl$_3$, δ) 35.0, 36.5, 55.9, 56.5, 72.8, 96.5, 112.5, 113.3, 123.2, 127.7, 132.2, 133.9, 140.4, 142.1, 163.7, 168.5. HRMS (ESI) calcd for $C_{20}H_{20}N_2NaO_7^+$ ([M+Na]$^+$): 423.1163, found: 423.1158.

Synthesis Example C-2

Compound c2: N-[3-(5-chloro-2-nitrophenyl)-3-methoxymethylpropyl]phthalimide

[Chemical formula 29]

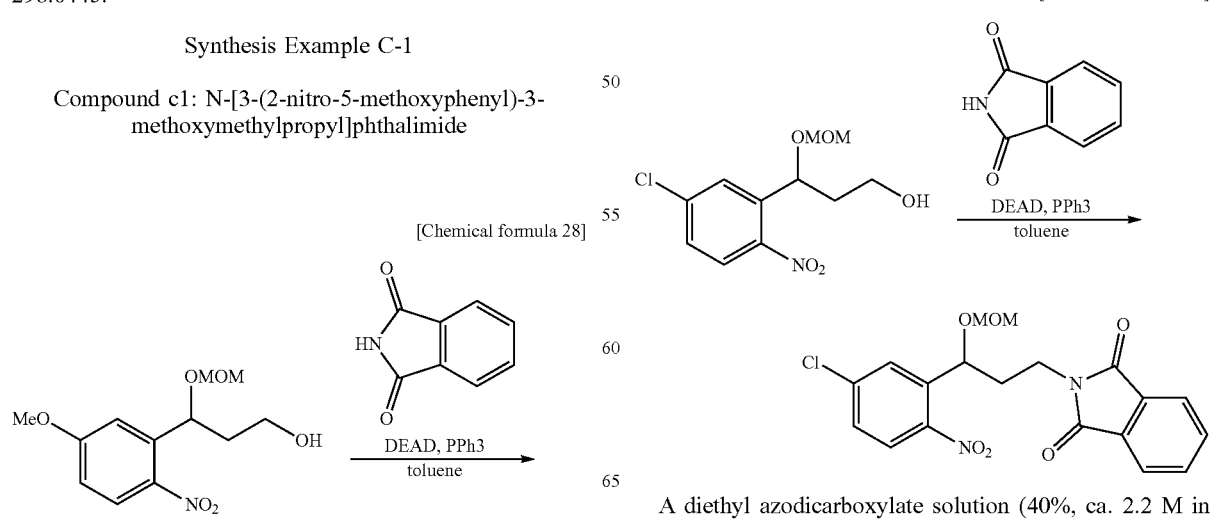

A diethyl azodicarboxylate solution (40%, ca. 2.2 M in toluene, 390 μL), triphenylphosphine (235 mg, 0.90 mmol), phthalimide (132 mg, 0.50 mmol) and Compound b2, i.e., alcohol, (121 mg, 0.44 mmol) in toluene (4 mL) were treated in the same manner as the methoxy compound. The crude product was chromatographed on silica gel (20% AcOEt/hexane) to give 178 mg (quant.) of a phthalimide derivative (title compound). This product was recrystallized from EtOH.

Pale yellow powder. mp 108.0-110.0° C. $^1$H-NMR (400 MHz, CDCl$_3$, δ) 2.04 (1H, dddd, J=5.2 Hz, 5.8 Hz, 9.2 Hz, 14.4 Hz), 2.24 (1H, dddd, J=2.3 Hz, 6.2 Hz, 8.4 Hz, 14.5 Hz), 3.32 (3H, s), 3.87 (1H, ddd, J=5.1 Hz, 6.4 Hz, 13.8 Hz), 4.04 (1H, ddd, J=5.8 Hz, 8.3 Hz, 14.0 Hz), 4.58 (1H, d, J=6.8 Hz), 4.72 (1H, d, J=6.8 Hz), 5.19 (1H, dd, J=2.2 Hz, 9.3 Hz), 7.35 (1H, dd, J=2.3 Hz, 8.8 Hz), 7.72 (2H, dd, J=3.0 Hz, 5.4 Hz), 7.80 (1H, d, J=2.4 Hz), 7.86 (2H, dd, J=3.0, 5.4 Hz), 7.92 (1H, d, J=8.8 Hz). $^{13}$C-NMR (125 MHz, CDCl$_3$, δ) 34.9, 36.5, 56.5, 72.7, 96.8, 123.3, 123.6, 126.3, 128.3, 128.5, 132.1, 134.0, 134.3, 140.3, 141.2, 145.5, 168.5, HRMS (ESI) calcd for $C_{19}H_{17}ClN_2NaO_6^+$ ([M+Na]$^+$): 427.0667. found: 427.0655.

Synthesis Example D-1

Compound d1: N-[3-(2-nitro-5-methoxyphenyl)-3-methoxymethylpropyl]acetamide

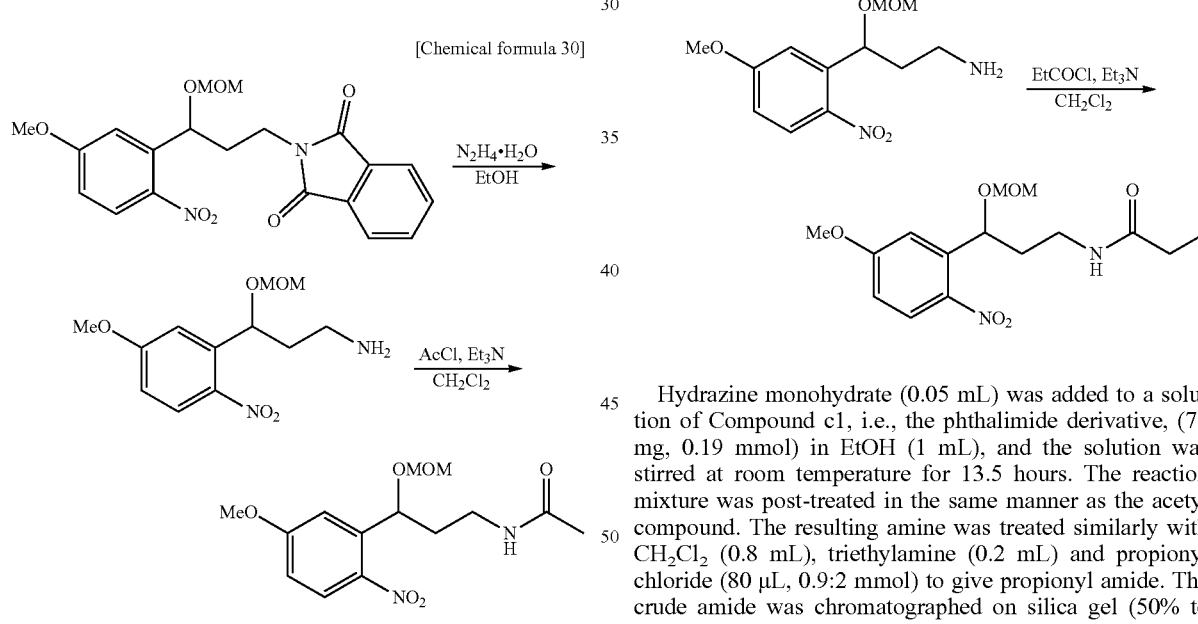

[Chemical formula 30]

Hydrazine monohydrate (0.1 mL) was added to a solution of Compound c1, i.e., the phthalimide derivative, (236 mg, 0.59 mmol) in EtOH (2.5 mL). The solution was stirred at room temperature for 20.5 hours, then heated at reflux for 30 minutes. The solution was cooled and acidified with a 2N aqueous HCl solution. This solution was filtrated through a celite pad. The filtrate was washed with hexane, then the aqueous layer was made into alkaline with solid KOH. The aqueous layer was subjected to extraction with AcOEt. The organic layer was washed with Na$_2$SO$_4$. After Na$_2$SO$_4$ was removed, the solvent was removed under reduced pressure. The resulting crude amine was dissolved in CH$_2$Cl$_2$ (1.2 mL) and triethylamine (0.3 mL). Acetyl chloride (210 µL) was added to a solution of the crude amine at 0° C., and then stirred at room temperature for 2.5 hours. A saturated aqueous sodium bicarbonate solution was added to the reaction mixture, and the resultant was subjected to extraction with CH$_2$Cl$_2$. The organic layer was washed with water, dried with Na$_2$SO$_4$, filtrated, and the solvent was removed under reduced pressure. The residue was chromatographed on silica gel (1% to EtOH/CH$_2$Cl$_2$) to give 75 mg (39%) of N-acetylated product (title compound).

Synthesis Example D-2

Compound d2: N-[3-(2-nitro-5-methoxyphenyl)-3-methoxymethylpropyl]propionamide

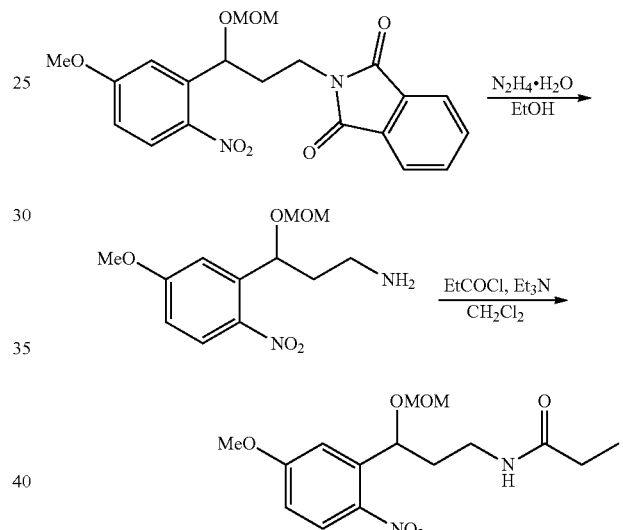

[Chemical formula 31]

Hydrazine monohydrate (0.05 mL) was added to a solution of Compound c1, i.e., the phthalimide derivative, (75 mg, 0.19 mmol) in EtOH (1 mL), and the solution was stirred at room temperature for 13.5 hours. The reaction mixture was post-treated in the same manner as the acetyl compound. The resulting amine was treated similarly with CH$_2$Cl$_2$ (0.8 mL), triethylamine (0.2 mL) and propionyl chloride (80 µL, 0.9:2 mmol) to give propionyl amide. The crude amide was chromatographed on silica gel (50% to 70% AcOEt/hexane) to give 38 mg (62%) of propionamide (title compound).

Yellowish brown oil. $^1$H-NMR (400 MHz, CDCl$_3$, δ) 1.19 (3H, t, J=7.6 Hz), 1.88 (1H, tdd, J=5.0 Hz, 9.5 Hz, 14.2 Hz), 2.04 (1H, dddd, J=2.7 Hz, 5.3 Hz, 9.2 Hz, 14.5 Hz), 2.26 (2H, q, J=7.6 Hz), 3.36 (3H, s), 3.45 (1H, dq, J=5.2 Hz, 13.6 Hz), 3.59 (1H, dddd, J=4.9 Hz, 5.7 Hz, 9.0 Hz, 13.9 Hz), 3.91 (3H, s), 4.49 (1H, d, J=6.7 Hz), 4.59 (1H, d, J=6.7 Hz), 5.43 (1H, dd, J=2.6 Hz, 9.2 Hz), 5.92 (1H, bs), 6.88 (1H, dd, J=2.8 Hz, 9.1 Hz), 7.24 (1H, d, J=2.8 Hz), 8.1 (1H, d, J=9.1 Hz). $^{13}$C-NMR (125 MHz, CDCl$_3$, δ) 9.9, 29.8, 36.5, 37.0, 55.9, 56.3, 72.2, 95.6, 112.7, 113.3, 127.9, 140.6, 142.1, 164.0, 173.9. HRMS (ESI) calcd for $C_{15}H_{22}N_2NaO_6^+$ ([M+Na]$^+$): 349.1370, found: 349.1368.

Synthesis Example D-3

Compound d3: N-[3-(2-nitro-5-methoxyphenyl)-3-methoxymethylpropyl]benzamide

[Chemical formula 32]

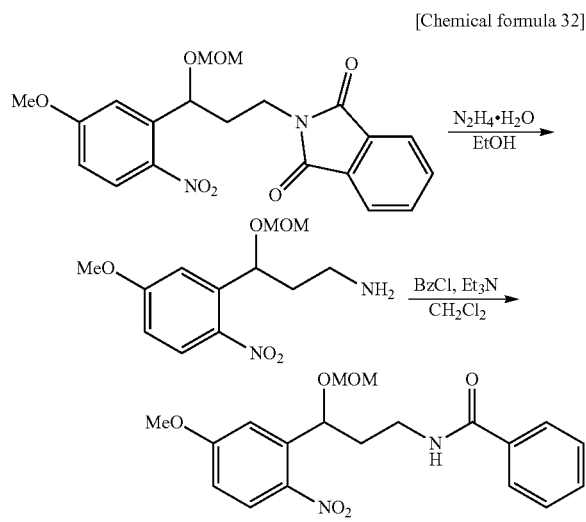

Hydrazine monohydrate (0.05 mL) was added to a solution of Compound c1, i.e., the phthalimide derivative, (73 mg, 0.18 mmol) in EtOH (1 mL), and the solution was stirred at room temperature for 4 hours. The reaction mixture was post-treated in the same manner as the acetyl compound. The resulting amine was treated similarly with $CH_2Cl_2$ (0.8 mL), triethylamine (0.2 mL) and benzoyl chloride (0.1 mL). The crude amide was chromatographed on silica gel (30% to 40% AcOEt/hexane) to give 48 mg (71%) of benzamide (title compound).

Yellowish brown oil. $^1$H-NMR (400 MHz, $CDCl_3$, δ) 2.01 (1H, ddt, J=4.8 Hz, 9.7 Hz, 14.4 Hz), 2.19 (1H, dddd, J=2.7 Hz, 5.1 Hz, 9.4 Hz, 14.5 Hz), 3.36 (3H, s), 3.64 (1H, ddd, J=5.1 Hz, 10.1 Hz, 13.7 Hz), 3.83 (1H, dddd, J=4.6 Hz, 5.9 Hz, 9.3 Hz, 13.8 Hz), 3.91 (3H, s), 4.51 (1H, d, J=6.6 Hz), 4.62 (1H, d, J=6.6 Hz), 5.55 (1H, dd, J=2.6 Hz, 9.1 Hz), 6.74 (1H, bs), 6.89 (1H, dd, J=2.8 Hz, 9.1 Hz), 7.27 (1H, d, J=2.8 Hz), 7.45-7.51 (3H, m), 7.84-7.85 (1H, m) 8.12 (1H, d, J=9.1 Hz). $^{13}$C-NMR (125 MHz, $CDCl_3$, δ) 36.8, 37.1, 56.0, 56.3, 72.4, 95.6, 100.0, 112.7, 113.4, 126.8, 126.9, 128.0, 128.6, 131.4, 134.6, 140.7, 141.9, 164.0, 167.5. HRMS (ESI) calcd for $C_{19}H_{22}N_2NaO_6^+$ ($[M+Na]^+$): 397.1370, found: 397.1359.

Synthesis Example D-4

Compound d4: N-[3-(2-nitro-5-methoxyphenyl)-3-methoxymethylpropyl]4-methoxybenzamide

[Chemical formula 33]

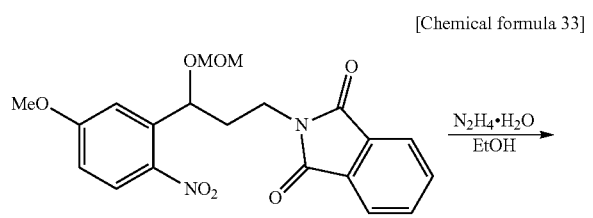

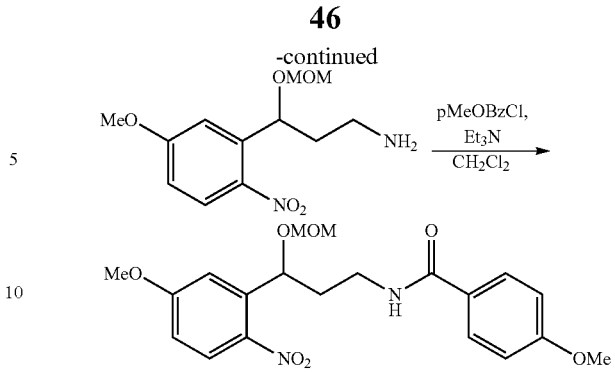

Hydrazine monohydrate (0.05 mL) was added to a solution of Compound c1, i.e., the phthalimide derivative, (84 mg, 0.21 mmol) in EtOH (1 mL), and the solution was heated at reflux for 30 minutes. The reaction mixture was post-treated in the same manner as the acetyl compound. The resulting crude amine was treated similarly with $CH_2Cl_2$ (0.8 mL), triethylamine (0.2 mL) and 4-methoxybenzoyl chloride (110 mg, 0.64 mmol) to give 4-methoxybenzamide. The crude amide was chromatographed on silica gel (50% to 60% AcOEt/hexane) to give 64 mg (75%) of 4-methoxybenzamide (title compound).

Brown solid. $^1$H-NMR (500 MHz, $CDCl_3$, δ) 2.01 (1H, dddd, J=14.5 Hz, 4.7 Hz, 9.6 Hz, 14.5 Hz), 2.17 (1H, dddd, J=2.6 Hz, 5.1 Hz, 9.5 Hz, 14.5 Hz), 3.35 (3H, s), 3.61 (1H, ddd, J=5.1 Hz, 10.0 Hz, 13.8 Hz), 3.78-3.84 (1H, m), 3.86 (3H, s), 3.91 (3H, s), 4.51 (1H, d, J=6.7 Hz), 4.61 (1H, d, J=6.7 Hz), 5.54 (1H, dd, J=2.5 Hz, 9.2 Hz), 6.65 (1H, br s), 6.88 (1H, dd, J=2.9 Hz, 9.1 Hz), 6.95 (2H, d, J=8.9 Hz), 7.27 (1H, d, J=2.8 Hz), 7.81 (2H, d, J=8.8 Hz), 8.12 (1H, d, J=9.10 Hz). $^{13}$C-NMR (125 MHz, $CDCl_3$, δ) 36.9, 36.9, 37.0, 55.4, 56.0, 56.2, 72.4, 95.6, 112.7, 113.4, 113.8, 126.9, 128.0, 128.7, 140.7, 142.0, 162.1, 164.0, 167.0. HRMS (ESI) calcd for $C_{20}H_{24}N_2NaO_7^+$ ($[M+Na]^+$): 427.1476, found: 427.1473.

Synthesis Example D-5

Compound d5: N-[3-(2-nitro-5-methoxyphenyl)-3-methoxymethylpropyl]2-methoxybenzamide

[Chemical formula 34]

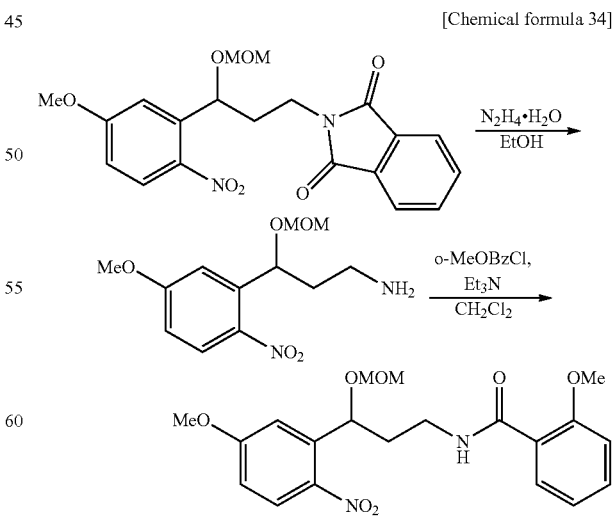

Hydrazine monohydrate (0.05 mL) was added to a solution of Compound c1, i.e., the phthalimide derivative, (90 mg, 0.23 mmol) in EtOH (1.5 mL), and the solution was heated at reflux for 30 minutes. The reaction mixture was post-treated in the same manner as the acetyl compound. The resulting crude amine was treated similarly with CH$_2$Cl$_2$ (0.8 mL), triethylamine (0.2 mL) and 2-methoxybenzoyl chloride (117 mg, 0.69 mmol) to give 2-methoxybenzamide. The crude amide was chromatographed on silica gel (40% to 60% AcOEt/hexane) to give 91 mg (99%) of 2-methoxybenzamide (title compound).

Colorless oil. $^1$H-NMR (500 MHz, CDCl$_3$, δ) 2.00 (1H, dd, J=5.0 Hz, 14.5 Hz), 2.21 (1H, dddd, J=3.0 Hz, 5.8 Hz, 9.0 Hz, 14.6 Hz), 3.34 (3H, s), 3.67-3.71 (1H, m), 3.75-3.79 (1H, m) 3.90 (3H, s), 4.02 (3H, s), 4.51 (1H, d, J=6.9 Hz), 4.60 (1H, d, J=6.9 Hz), 5.53 (1H, dd, J=2.8 Hz, 9.4 Hz), 6.86 (1H, dd, J=2.9 Hz, 9.1 Hz), 6.99 (1H, d, J=8.3 Hz), 7.1 (1H, ddd, J=0.7 Hz, 7.2 Hz, 7.9 Hz), 7.28 (1H, d, J=2.8 Hz), 7.44 (1H, ddd, J=1.7 Hz, 7.3 Hz, 8.3 Hz), 8.08 (1H, d, J=9.1 Hz), 8.21 (1H, s), 8.22 (1H, dd, Hz=1.8 Hz, 7.8 Hz). $^{13}$C-NMR (125 MHz, CDCl$_3$, δ) 36.7, 36.8, 55.8, 55.9, 56.1, 71.8, 95.4, 110.9, 112.7, 113.3, 121.5, 127.7, 132.2, 132.6, 140.8, 142.2, 157.7, 163.9, 165.4. HRMS (ESI) calcd for C$_{20}$H$_{24}$N$_2$NaO$_7^+$ ([M+Na]$^+$): 427.1476, found: 427.1466.

Synthesis Example D-6

Compound d6: N-[3-(2-nitro-5-methoxyphenyl)-3-methoxymethylpropyl]2-naphthamide

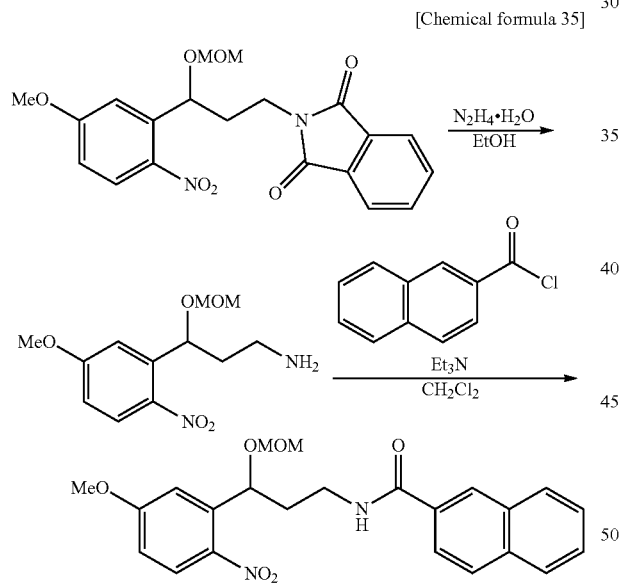

[Chemical formula 35]

Hydrazine monohydrate (0.05 mL) was added to a solution of Compound c1, i.e., the phthalimide derivative, (85 mg, 0.21 mmol) in EtOH (1 mL), and the solution was heated at reflux for 30 minutes. The reaction mixture was post-treated in the same manner as the acetyl compound. The resulting crude amine was treated similarly with CH$_2$Cl$_2$ (0.8 mL), triethylamine (0.2 mL) and 2-naphthoyl chloride (137 mg, 0.72 mmol) to give 2-naphthamide. The crude amide was chromatographed on silica gel (40% to 60% AcOEt/hexane) to give 81 mg (89%) of 2-naphthamide (title compound).

Light brown oil. $^1$H-NMR (500 MHz, CDCl$_3$, δ) 2.06 (1H, ddd, J=14.5 Hz, 5.1 Hz, 9.3 Hz), 2.23 (1H, dddd, J=2.7 Hz, 5.2 Hz, 9.3 Hz, 14.5 Hz), 3.38 (3H, d, J=0.7 Hz), 3.70 (1H, ddd, J=5.1 Hz, 10.1 Hz, 13.6 Hz), 3.85-3.89 (1H, m), 3.91 (3H, s), 4.53 (1H, d, J=6.7 Hz), 4.64 (1.0H, d, J=6.7 Hz), 5.60 (1H, dd, J=2.5 Hz, 9.1 Hz), 6.89 (1H, dd, J=2.9 Hz, 9.2 Hz), 6.92 (1H, br s), 7.29 (1H, d, J=2.9 Hz), 8.12 (1H, d, J=9.2 Hz), 7.52-7.58 (2H, m), 7.87-7.94 (4H, m), 8.38 (1H, s). $^{13}$C-NMR (125 MHz, CDCl$_3$, δ) 36.8, 37.3, 56.0, 56.3, 72.5, 95.6, 112.7, 113.4, 123.5, 126.6, 127.4, 127.5, 127.7, 128.0, 128.4, 129.0, 131.8, 132.7, 134.7, 140.7, 141.9, 164.0, 167.5. HRMS (ESI) calcd for C$_{23}$H$_{24}$N$_2$NaO$_6^+$ ([M+Na]$^+$): 447.1527, found: 447.1526.

Synthesis Example D-7

Compound d7: N-[3-(2-nitro-5-methoxyphenyl)-3-methoxymethylpropyl]2-picolinamide

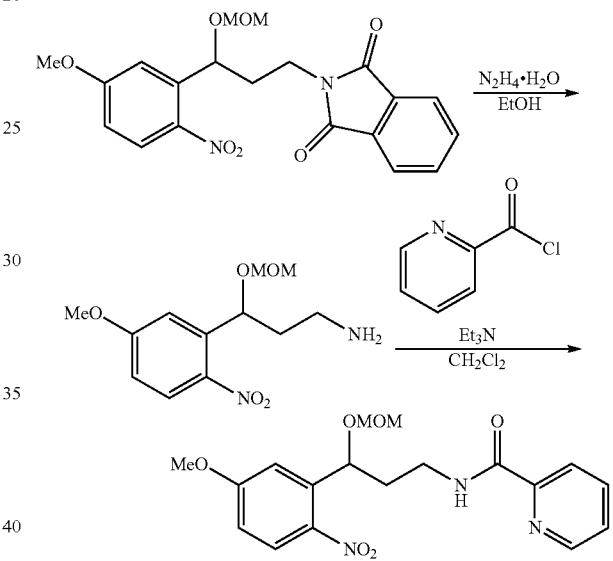

[Chemical formula 36]

Hydrazine monohydrate (0.05 mL) was added to a solution of Compound c1, i.e., the phthalimide derivative, (86 mg, 0.21 mmol) in EtOH (1.5 mL), and the solution was heated at reflux for 30 minutes. The reaction mixture was post-treated in the same manner as the acetyl compound. The resulting crude amine was treated similarly with CH$_2$Cl$_2$ (0.8 mL), triethylamine (0.2 mL) and picolinoyl chloride (111 mg, 0.63 mmol) to give picolinamide. The crude amide was chromatographed on silica gel (30% to 50% AcOEt/hexane) to give 69 mg (86%) of picolinamide (title compound).

Light brown solid. $^1$H-NMR (500 MHz, CDCl$_3$, δ) 2.02 (1H, ddt, J=6.0 Hz, 8.6 Hz, 14.5 Hz), 2.25 (1H, ddt, J=2.9 Hz, 7.2 Hz, 14.3 Hz), 3.38 (3H, s), 3.72-3.78 (2H, m), 3.89 (3H, s), 4.53 (1H, d, J=6.8 Hz), 4.64 (1H, d, J=6.8 Hz), 5.52 (1H, dd, J=2.8, 8.9 Hz), 6.86 (1H, dd, J=2.9 Hz, 9.2 Hz), 7.28 (1H, d, J=2.9 Hz), 7.41 (1H, ddd, J=1.1 Hz, 4.8 Hz, 7.6 Hz), 7.84 (1H, dt, J=1.7, 7.7 Hz), 8.08 (1H, d, J=9.1 Hz), 8.19 (1H, d, J=7.8 Hz), 8.42 (1H, br s), 8.56 (1H, ddd, J=0.8, 1.5, 4.9 Hz). $^{13}$C-NMR (125 MHz, CDCl$_3$, δ) 36.7, 37.0, 55.9, 56.3, 72.7, 95.5, 112.7, 113.3, 122.1, 126.0, 127.8, 137.3, 140.8, 141.9, 148.1, 150.0, 163.8, 164.4. HRMS (ESI) calcd for C$_{18}$H$_{21}$N$_3$NaO$_6^+$ ([M+Na]$^+$): 398.1323, found: 398.1320.

Synthesis Example D-8

Compound d8: N-[3-(5-chloro-2-nitrophenyl)-3-methoxymethylpropyl]acetamide

[Chemical formula 37]

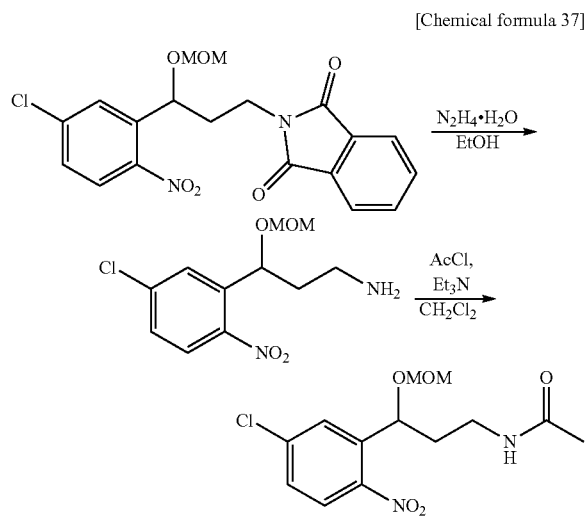

Hydrazine monohydrate (0.1 mL) was added to a solution of Compound c2, i.e., the phthalimide derivative, (66 mg, 0.16 mmol) in EtOH (1 mL), and the solution was heated at reflux for 30 minutes. The reaction mixture was post-treated in the same manner as the methoxy compound. The resulting crude amine, $CH_2Cl_2$ (0.8 mL), triethylamine (0.2 mL) and acetyl chloride (70 μL) were treated in the same manner as the methoxy product. The crude amide was chromatographed on silica gel (1% to 2% $EtOH/CH_2Cl_2$) to give 50 mg (quant.) of a N-acetylated product (title compound).

Colorless oil. $^1$H-NMR (400 MHz, $CDCl_3$, δ) 1.89 (1H, ddt, J=5.2 Hz, 9.3 Hz, 14.5 Hz), 2.01-2.08 (1H, m), 2.03 (3H, s), 3.34 (3H, s), 3.44 (1H, ddt, J=5.4 Hz, 10.7 Hz, 13.7 Hz), 3.57 (1H, dddd, J=5.1 Hz, 6.2 Hz, 8.8 Hz, 13.7 Hz), 4.48 (1H, d, J=6.8 Hz), 4.61 (1H, d, J=6.8 Hz), 5.28 (1H, dd, J=2.7 Hz, 9.3 Hz), 5.86 (1H, s), 7.40 (1H, dd, J=2.4 Hz, 8.8 Hz), 7.76 (1H, d, J=2.3 Hz), 7.96 (1H, d, J=8.8 Hz). $^{13}$C-NMR (125 MHz, $CDCl_3$, δ) 23.3, 36.5, 37.1, 56.2, 72.1, 95.9, 126.3, 128.5, 128.5, 140.5, 140.8, 145.8, 170.2. HRMS (ESI) calcd for $C_{13}H_{17}ClN_2NaO_5^+$ ([M+Na]$^+$): 339.0718. found: 339.0711.

Synthesis Example E-1

Compound e1: N-[3-(2-nitro-5-methoxyphenyl)-3-oxopropyl]acetamide

[Chemical formula 38]

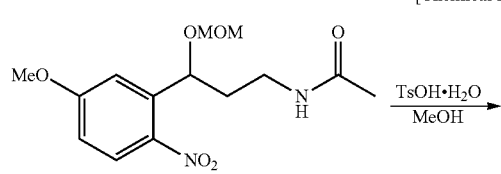

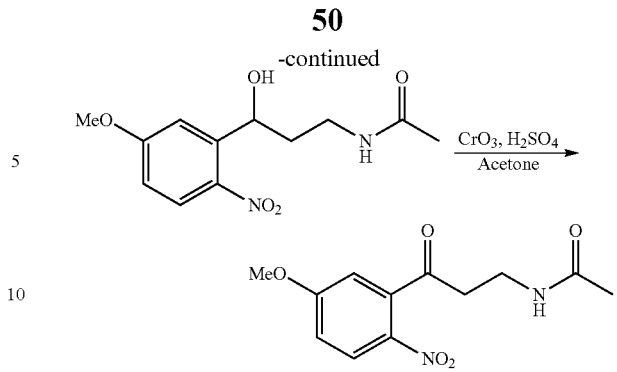

p-Toluenesulfonic acid monohydrate (19 mg) was added to a solution of Compound d1, i.e., methoxymethyl ether, (67.5 mg, 0.22 mmol) in methanol (1 mL), and the solution was heated at reflux for 4.5 hours. The reaction mixture was cooled at 0° C., neutralized with an aqueous sodium bicarbonate solution, and subjected to extraction with AcOEt. The organic layer was washed with brine, dried with $Na_2SO_4$ and evaporated. The residue was dissolved in acetone (2 mL) and added with Jones reagent (0.15 mL). This solution was stirred at room temperature for an hour. The reaction mixture was poured into ice, added with an aqueous $Na_2SO_3$ solution, and subjected to extraction with AcOEt. The organic layer was washed with brine, dried with $Na_2SO4$ and evaporated. The residue was chromatographed on silica gel (1% to 2% $EtOH/CH_2Cl_2$) to give 37 mg (54%) of ketone (title compound). The product was recrystallized from toluene-hexane.

White powder. mp 102.5-104.0° C. $^1$H-NMR (500 MHz, $CDCl_3$, δ) 2.02 (3H, s), 2.97 (2H, t, J=5.6 Hz), 3.69 (2H, q, J=5.8 Hz), 3.92 (3H, s), 6.18 (1H, bs), 6.73 (1H, d, J=2.7 Hz), 7.01 (1H, dd, J=2.7 Hz, 9.2 Hz), 8.16 (1H, d, J=9.2 Hz). $^{13}$C-NMR (125 MHz, $CDCl_3$, δ) 23.3, 34.1, 42.6, 56.3, 111.8, 115.0, 127.3, 137.9, 140.3, 164.4, 170.4, 202.0. HRMS (ESI) rated for $C_{12}H_{14}N_2NaO_5^+$ ([M+Na]$^+$): 289.0795, found: 289.0788.

Synthesis Example E-2

Compound e2: N-[3-(2-nitro-5-methoxyphenyl)-3-oxopropyl]propionamide

[Chemical formula 39]

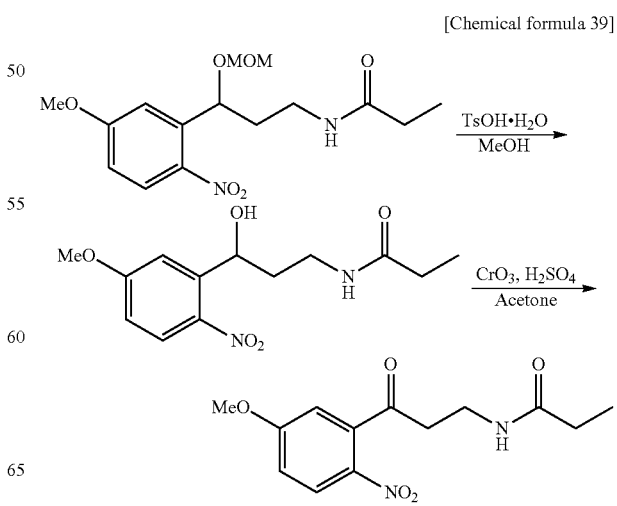

According to the procedure described above for acetamide, Compound d2, i.e., methoxymethyl ether, (38 mg, 0.12 mmol) was treated with p-toluenesulfonic acid monohydrate (16.1 mg) in methanol (1 mL) and then treated with Jones reagent (100 μL) in acetone (1 mL) to give 24 mg (75%) of ketone (title compound). The product was recrystallized from chloroform-hexane.

White powder. mp 92.0-93.5° C. $^1$H-NMR (500 MHz, CDCl$_3$, δ) 1.17 (3H, t, J=7.6 Hz), 2.25 (2H, q, J=7.6 Hz), 2.98 (2H, t, J=5.5 Hz), 3.71 (2H, q, J=5.8 Hz), 3.92 (3H, s), 6.14 (1H, bs), 6.73 (1H, d, J=2.8 Hz), 7.01 (1H, dd, J=2.8, 9.2 Hz), 8.16 (1H, d, J=9.2 Hz). $^{13}$C-NMR (125 MHz, CDCl$_3$, δ) 9.7, 29.7, 34.0, 42.6, 56.3, 111.8, 115.0, 127.3, 138.0, 140.4, 164.4, 174.1, 202.0. HRMS (ESI) calcd for C$_{13}$H$_{16}$N$_2$NaO$_5$$^+$ ([M+Na]$^+$): 303.0951, found: 303.0944.

Synthesis Example E-3

Compound e3: N-[3-(2-nitro-5-methoxyphenyl)-3-oxopropyl]benzamide

[Chemical formula 40]

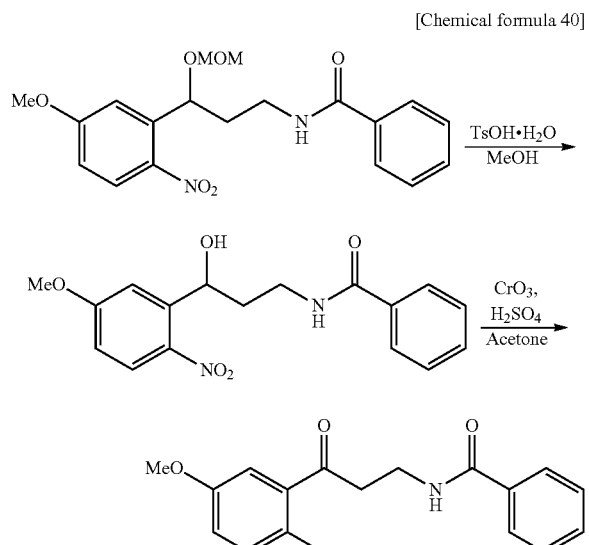

According to the procedure described above for acetamide, Compound d3, i.e., methoxymethyl ether, (43 mg, 0.12 mmol) was treated with p-toluenesulfonic acid monohydrate (13 mg) and Jones reagent (100 μL) to give 30 mg (80%) of ketone (title compound). The product was recrystallized from chloroform-hexane.

White powder. mp 130.5-132.0° C. $^1$H-NMR. (500 MHz, CDCl$_3$, δ) 3.10 (2H, t, J=5.6 Hz), 3.90 (3H, s), 3.93 (2H, q, J=5.8 Hz), 6.74 (1H, d, J=2.7 Hz), 6.90 (1H, bs), 7.01 (1H, dd, J=2.8 Hz, 9.2 Hz), 7.43-7.46 (2H, m), 7.49-7.52 (1H, m), 7.81-7.83 (2H, m), 8.17 (1H, d, J=9.2 Hz), $^{13}$C-NMR (125 MHz, CDCl$_3$, δ) 34.7, 42.6, 56.3, 111.8, 115.2, 127.0, 127.3, 128.6, 131.5, 134.4, 138.0, 140.3, 164.5, 167.6, 202.1. HRMS (ESI) calcd for C$_{17}$H$_{16}$N$_2$NaO$_5$$^+$ ([M+Na]$^+$): 351.0951, found: 351.0942.

Synthesis Example E-4

Compound e4: N-[3-(2-nitro-5-methoxyphenyl)-3-oxopropyl]-4-methoxybenzamide

[Chemical formula 41]

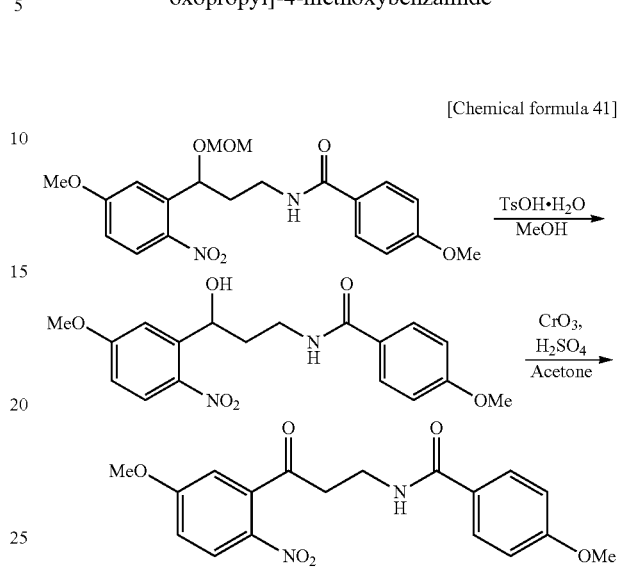

According to procedure described above for acetamide, Compound d4, i.e., methoxymethyl ether, (55 mg, 0.14 mmol) was treated with p-toluenesulfonic acid monohydrate (17 mg) and Jones reagent (100 μL) to give 34 mg (70%) of ketone (title compound). The product was recrystallized from ethyl acetate-hexane.

White powder. mp 131.5-132.5° C. $^1$H-NMR (500 MHz, CDCl$_3$, δ) 3.09 (2H, t, J=5.6 Hz), 3.85 (3H, s), 3.91 (3H, s), 3.91 (2H, q, J=5.7 Hz), 6.74 (1H, d, 1=2.7 Hz), 6.78 (1H, br s), 6.94 (2H, d, J=8.9 Hz), 7.01 (1H, dd, J=2.7 Hz, 9.2 Hz), 7.79 (2H, d, J=8.9 Hz), 8.17 (1H, d, J=9.20 Hz). $^{13}$C-NMR (125 MHz, CDCl$_3$, δ) 34.6, 42.7, 55.4, 56.3, 111.8, 113.8, 115.2, 126.7, 127.3, 128.8, 138.0, 140.4, 162.2, 164.5, 167.1, 202.2. HRMS (ESI) calcd for C$_{18}$H$_{18}$N$_2$NaO$_6$$^+$ ([M+Na]$^+$): 381.1057, found: 381.1056.

Synthesis Example E-5

Compound e5: N-[3-(2-nitro-5-methoxyphenyl)-3-oxopropyl]-2-methoxybenzamide

[Chemical formula 42]

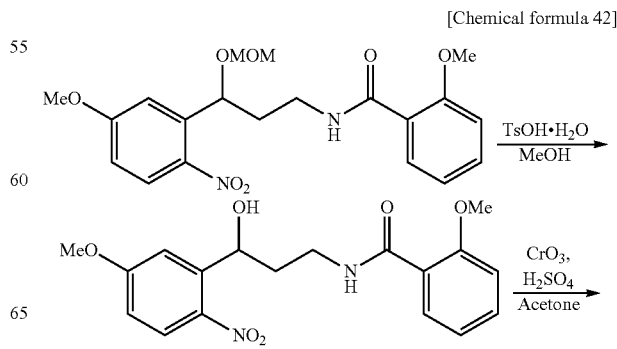

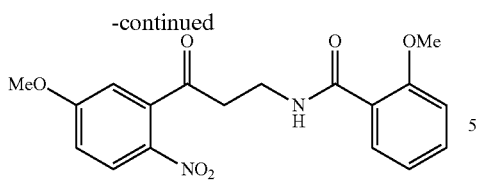

According to the procedure described above for acetamide, Compound d5, i.e., methoxymethyl ether, (94 mg, 0.22 mmol) was treated with p-toluenesulfonic acid monohydrate (22 mg) and Jones reagent (100 μL) to give 48 mg (60%) of ketone (title compound). The product was recrystallized from toluene-cyclohexane.

White powder. mp 117.0-118.0° C. $^1$H-NMR (500 MHz, CDCl$_3$, δ) 3.12 (2H, t, J=5.8 Hz), 3.88 (3H, s), 3.91 (2H, q, J=5.9 Hz), 3.99 (3H, s), 6.75 (1H, d, J=2.7 Hz), 7.07 (1H, dt, J=1.0 Hz, 7.7 Hz), 7.45 (1H, ddd, J=1.8 Hz, 7.3 Hz, 8.3 Hz), 8.15 (1H, d, J=9.2 Hz), 8.20 (1H, dd, J=1.9, 7.8 Hz), 8.5 (1H, s). $^{13}$C-NMR (125 MHz, CDCl$_3$, δ) 34.5, 42.7, 55.9, 56.3, 111.3, 111.8, 115.1, 121.1, 121.3, 127.1, 132.1, 132.8, 138.0, 140.6, 157.7, 164.4, 165.4, 202.0. HRMS (ESI) calcd for $C_{18}H_{18}N_2NaO_6^+$ ([M+Na]$^+$): 381.1057, found: 381.1056.

Synthesis Example E-6

Compound e6: N-[3-(2-nitro-5-methoxyphenyl)-3-oxopropyl]-2-naphthamide

[Chemical formula 43]

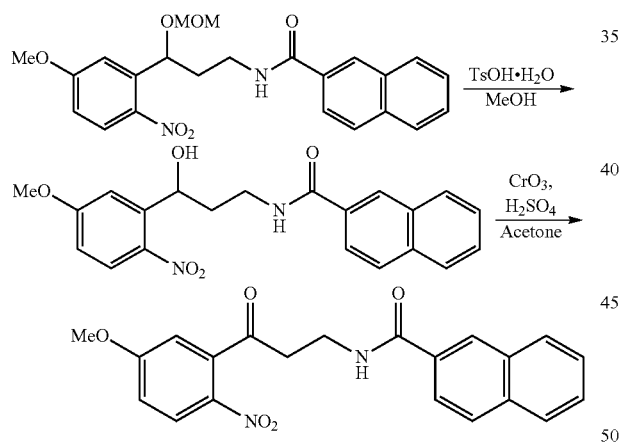

According to the procedure described above for acetamide, Compound d6, i.e., methoxymethyl ether, (72 mg, 0.17 mmol) was treated with p-toluenesulfonic acid monohydrate (30 mg) and Jones reagent (75 μL) to give 43 mg (67%) of ketone (title compound). The product was recrystallized from ethyl acetate-hexane.

Pale yellow powder. mp 164.0-165.0° C. $^1$H-NMR (500 MHz, CDCl$_3$, δ) 3.14 (2H, t, J=5.6 Hz), 3.90 (3H, s), 3.99 (2H, q, J=5.7 Hz), 6.8 (1H, d, J=2.8 Hz), 7.01 (1H, dd, J=2.7 Hz, 9.2 Hz), 7.04 (1H, br s), 7.52-7.58 (2H, m), 7.87-7.96 (4H, m), 8.17 (1H, d, J=9.2 Hz), 8.35 (1H, s). $^{13}$C-NMR (125 MHz, CDCl$_3$, δ) 34.8, 42.7, 56.3, 111.8, 115.2, 123.6, 126.7, 127.3, 127.5, 127.6, 127.7, 128.5, 129.0, 131.6, 132.6, 134.8, 138.0, 140.3, 164.5, 167.6, 202.2. HRMS (ESI) calcd for $C_{21}H_{18}N_2NaO_5^+$ ([M+Na]$^+$): 401.1108 found: 401.1100.

Synthesis Example E-7

Compound e7: N-[3-(2-nitro-5-methoxyphenyl)-3-oxopropyl]2-picolinebenzamide

[Chemical formula 44]

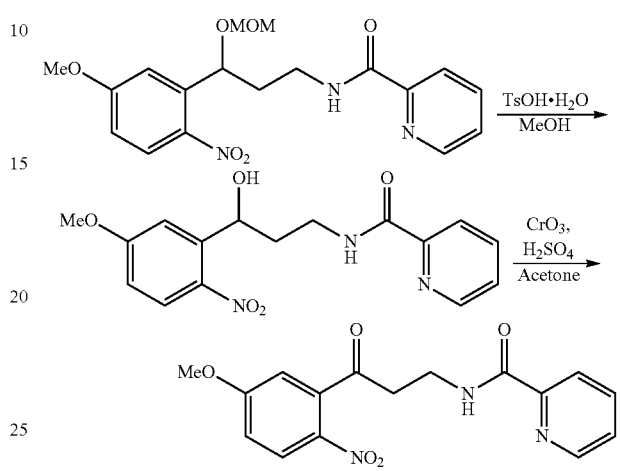

According to the procedure described above for acetamide, Compound d7, i.e., methoxymethyl ether, (57 mg, 0.15 mmol) was treated with p-toluenesulfonic acid monohydrate (43 mg, 0.25 mmol) and Jones reagent (75 μL) to give 26 mg (53%) of ketone (title compound). The product was recrystallized from toluene-cyclohexane.

White powder. mp 117.0-117.5° C. $^1$H-NMR (500 MHz, CDCl$_3$, δ) 3.12 (2H, t, J=6.0 Hz), 3.88 (3H, s), 3.93 (2H, q, J=6.2 Hz), 6.76 (1H, d, J=2.8 Hz), 6.99 (1H, dd, J=2.7 Hz, 9.2 Hz), 7.43 (1H, ddd, J=1.2 Hz, 4.8 Hz, 7.6 Hz), 7.84 (1H, dt, J=1.7 Hz, 7.7 Hz), 8.15 (1H, d, J=9.2 Hz), 8.18 (1H, td, J=1.0 Hz, 7.7 Hz), 8.55 (1H, br s), 8.6 (1.2H, ddd, J=0.9 Hz, 1.7 Hz, 4.7 Hz). $^{13}$C-NMR (125 MHz, CDCl$_3$, δ) 34.5, 42.7, 56.3, 111.8, 115.3, 122.1, 126.2, 127.1, 137.3, 138.0, 140.5, 148.2, 149.7, 164.4, 164.6, 201.4. HRMS (ESI) calcd for $C_{16}H_{15}N_3NaO_5^+$ ([M+Na]$^+$): 352.0904, found: 352.0903.

Synthesis Example E-8

Compound e8: N-[3-(5-chloro-2-nitrophenyl)-3-oxopropyl]-acetamide

[Chemical formula 45]

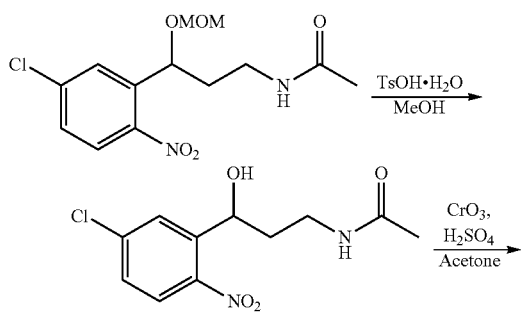

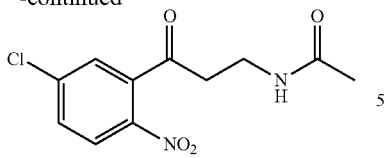

According to the procedure described above for acetamide, Compound d8, i.e., methoxymethyl ether, (67 mg, 0.22 mmol) was treated with p-toluenesulfonic acid monohydrate (17 mg) and Jones reagent (100 μL) to give 48 mg (60%) of ketone (title compound). The product was recrystallized from toluene-cyclohexane.

White powder. mp 122.5-124.5° C. $^1$H-NMR (400 MHz, CDCl$_3$, δ) 2.02 (3H, s), 3.02 (2H, t, J=5.5 Hz), 3.69 (2H, q, J=5.8 Hz), 6.12 (1H, bs), 7.34 (1H, d, J=2.2 Hz), 7.58 (1H, dd, J=2.2 Hz, 8.8 Hz), 8.11 (1H, d, J=8.8 Hz). $^{13}$C-NMR (125 MHz, CDCl$_3$, δ) 23.3, 29.7, 34.0, 42.5, 126.1, 127.2, 130.7, 138.8, 141.5, 143.6, 170.5, 200.4. HRMS (ESI) calcd for $C_{11}H_{11}ClN_2NaO_4^+$ ([M+Na]$^+$): 293.0300, found: 293.0293.

Synthesis Example F-1

Compound 1: N-[3-(2-amino-5-methoxyphenyl)-3-oxopropyl]-acetamide

[Chemical formula 46]

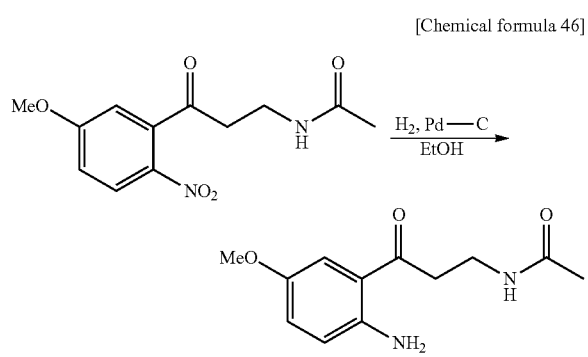

A suspension of Compound e1, i.e., the nitrobenzene derivative, (33 mg, 0.13 mmol) and 10% palladium on carbon (12 mg) in ethanol was stirred in a hydrogen atmosphere for 30 minutes at room temperature. The mixture was filtrated through a celite pad. The filtrate was concentrated under reduced pressure. The residue was recrystallized from toluene to give 17 mg (58%) of an aniline derivative (title compound).

Yellowish brown solid. $^1$H-NMR (500 MHz, CDCl$_3$, δ) 1.95 (3H, s), 3.17 (2H, t, J=5.5 Hz), 3.65 (2H, q, J=5.8 Hz), 3.77 (3H, s), 5.99 (2H, bs), 6.17 (1H, bs), 6.64 (1H, d, J=9.0 Hz), 6.98 (1H, dd, J=8.9 Hz, 2.9 Hz), 7.14 (1H, d, J=2.9 Hz). $^{13}$C-NMR (125 MHz, CDCl$_3$, δ) 23.4, 34.5, 38.8, 56.0, 112.9, 117.3, 118.8, 124.0, 145.1, 150.2, 170.1, 200.9. HRMS (ESI) calcd for $C_{12}H_{16}N_2NaO_3^+$ ([M+Na]$^+$): 259.1053, found: 259.1052.

Synthesis Examples F-2 and G-2

Compound 2: N-[3-(2-amino-5-methoxyphenyl)-3-oxopropyl]-propionamide; and Compound 11: N-[3-(2-formylamino-5-methoxyphenyl)-3-oxopropyl]-propionamide

[Chemical formula 47]

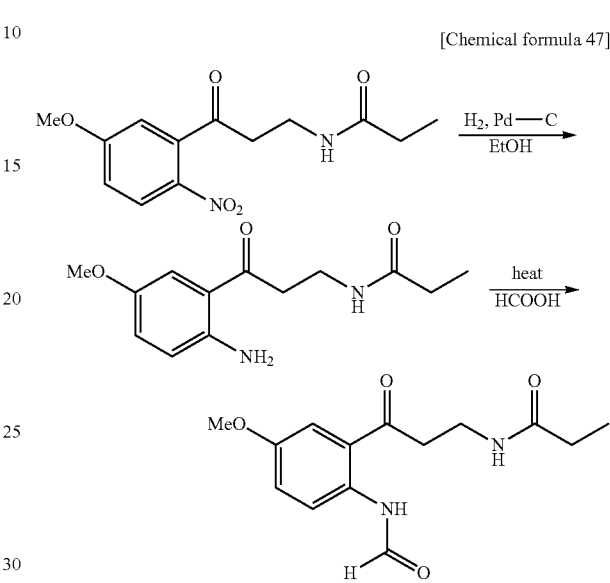

According to the procedure described above for acetamide, Compound e2, i.e., the nitrobenzene derivative, (22 mg, 0.079 mmol) was treated with 10% palladium on carbon (4 mg) in EtOH (1 mL) to give a crude amine. The residue was recrystallized from ethyl acetate and hexane to give 9 mg (14%) of an aniline derivative (title Compound 2). The residual crude amine was dissolved in formic acid and heated at reflux for 5 hours. The reaction mixture was poured into ice, and subjected to extraction with chloroform. The organic layer was washed with water and an aqueous sodium bicarbonate solution, and dried and evaporated with Na$_2$SO$_4$. The residue was chromatographed on silica gel (1% to 3% EtOH/CH$_2$Cl$_2$) to give 6 mg (53%) of formamide (title Compound 11). The formamide was recrystallized from ethyl acetate.

(Aniline derivative) Yellow powder. mp 79-81° C. $^1$H-NMR (500 MHz, CDCl$_3$, δ) 1.13 (3H, t, J=7.60 Hz), 2.18 (2H, q, J=7.6 Hz) 3.17 (2H, t, J=5.6 Hz), 3.66 (2H, q, J=5.8 Hz), 3.77 (3H, bs), 6.65 (1H, d, J=8.95 Hz), 6.98 (1H, dd, J=9.0 Hz, 2.9 Hz), 7.15 (1H, d, J=2.9 Hz). $^{13}$C-NMR (125 MHz, CDCl$_3$, δ) 9.8, 29.8, 34.4, 38.8, 56.0, 113.0, 117.5, 118.9, 124.0, 144.9, 150.3, 173.8, 201.1. HRMS (EST) calcd for $C_{13}H_{18}N_2NaO_3^+$ ([M+Na]$^+$): 273.1210, found: 273.1205.

(Formamide) Pale yellow powder. mp 131-134° C., $^1$H-NMR (500 MHz, CDCl$_3$, δ) 1.14 (3H, t, J=7.6 Hz), 2.19 (2H, q, J=7.6 Hz), 3.28 (2H, t, J=5.7 Hz), 3.66 (2H, q, J=5.8 Hz), 3.84 (3H, s), 6.02 (1H, bs, J=6.8 Hz), 7.14 (1H, dd, J=9.2 Hz, 2.9 Hz), 7.38 (1H, d, J=3.0 Hz), 8.45 (1H, d, J=1.9 Hz), 8.68 (1H, d, J=9.2 Hz), 11.22 (1H, bs). $^{13}$C-NMR (125 MHz, CDCl$_3$, δ): 9.7, 29.7, 34.3, 39.7, 55.7, 115.6, 120.8, 122.6, 123.2, 133.3, 154.9, 159.4, 173.9, 203.5. HRMS (ESI) calcd for $C_{14}H_{18}N_2NaO_4^+$ ([M+Na]$^+$): 301.1159, found: 301.1158.

Synthesis Example F-3

Compound 3: N-[3-(2-amino-5-methoxyphenyl)-3-oxopropyl]-benzamide

[Chemical formula 48]

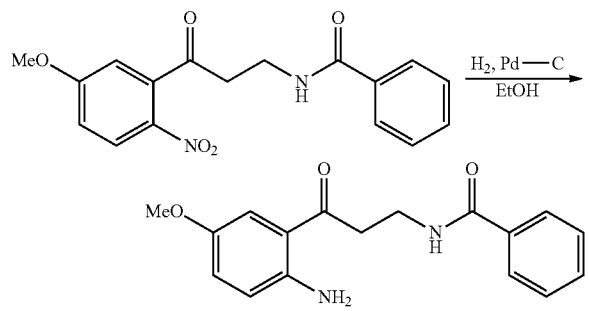

According to the procedure described above for acetamide, Compound e3, i.e., the nitrobenzene derivative, (23 mg, 0.071 mmol) was treated with 10% palladium on carbon (3 mg) in EtOH (1 mL) to give a crude amine. The residue was chromatographed on silica gel (40% to 70% AcOEt/hexane) to give 21 mg (86%) of an aniline derivative (title compound).

Yellowish brown solid. $^1$H-NMR (500 MHz, CDCl$_3$, δ) 3.29 (2H, t, J=5.5 Hz), 3.77 (3H, s), 3.87 (2H, q, J=5.8 Hz), 6.67 (1H, d, J=9.0 Hz), 6.98 (1H, dd, J=9.0 Hz, 2.9 Hz), 7.17 (1H, d, J=2.8 Hz), 7.43-7.41 (1H, m), 7.47-7.46 (2H, m), 7.77-7.75 (2H, m). $^{13}$C-NMR (125 MHz, CDCl$_3$, δ) 35.0, 38.8, 56.0, 113.0, 117.6, 119.1, 124.0, 126.9, 128.5, 131.4, 134.5, 144.6, 150.4, 167.4, 201.2. HRMS (ESI) calcd for C$_{17}$H$_{18}$N$_2$NaO$_3^+$ ([M+Na]$^+$): 321.1210, found: 321.1202.

Synthesis Example F-4

Compound 4: N-[3-(2-amino-5-methoxyphenyl)-3-oxopropyl]-4-methoxybenzamide

[Chemical formula 49]

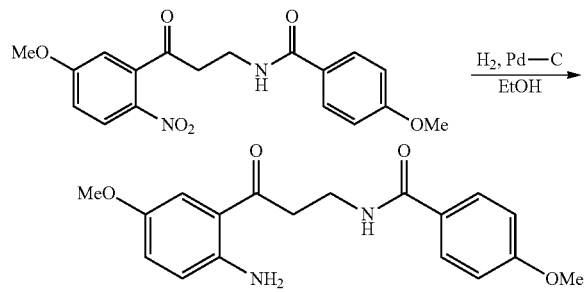

According to the procedure described above for acetamide, Compound e4, i.e., the nitrobenzene derivative, (23 mg, 0.064 mmol) was treated with 10% palladium on carbon (22 mg) in EtOH (1 mL) to give a crude amine. The residue was chromatographed on silica gel (40% to 50% AcOEt/hexane) to give 14 mg (65%) of an aniline derivative (title compound). The product was recrystallized from ethyl acetate and hexane.

Yellow powder. 150-151° C. $^1$H-NMR (500 MHz, CDCl$_3$, δ) 3.28 (2H, t, J=5.5 Hz), 3.86 (2H, q, J=5.7 Hz), 3.76 (3H, s), 3.84 (s, 3H), 6.65 (1H, d, J=9.0 Hz), 6.90 (2H, d, J=8.9 Hz), 6.84 (1H, br s), 6.98 (1H, dd J=2.9 Hz, 9.0 Hz), 7.17 (1H, d, J=2.9), 7.72 (2H, d, J=8.9 Hz). $^{13}$C-NMR (125 MHz, CDCl$_3$, δ) 35.0, 38.9, 55.4, 56.0, 113.0, 113.7, 117.6, 119.0, 124.0, 126.8, 128.7, 144.7, 150.4, 162.1, 166.9, 201.3. HRMS (ESI) calcd for C$_{18}$H$_{20}$N$_2$NaO$_4^+$ ([M+Na]$^+$): 351.1315, found: 351.1311.

Synthesis Example F-5

Compound 5: N-[3-(2-amino-5-methoxyphenyl)-3-oxopropyl]-2-methoxybenzamide

[Chemical formula 50]

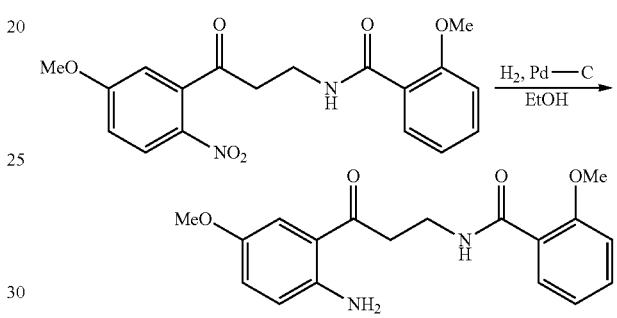

According to the procedure described above for acetamide, Compound e5, i.e., the nitrobenzene derivative, (21 mg, 0.060 mmol) was treated with 10% palladium on carbon (8 mg) in EtOH (1 mL) to give a crude amine. The residue was chromatographed on silica gel (40% to 50% AcOEt/hexane) to give 13 mg (65%) of an aniline derivative (title compound). The product was recrystallized from toluene and hexane.

Yellow powder. mp. 134.5-136.0° C. $^1$H-NMR (500 MHz, CDCl$_3$, δ) 3.29 (2H, t, J=5.8 Hz), 3.8 (3H, s), 3.87 (2H, q, J=5.9 Hz), 3.94 (3H, s), 6.6 (1H, d, J=8.9 Hz), 6.94 (1H, d, J=8.3 Hz), 6.97 (1H, dd, J=2.9 Hz, 8.9 Hz), 7.06 (1H, ddd, J=0.9 Hz, 7.5 Hz, 7.7 Hz), 7.20 (1H, d, J=2.9 Hz), 7.42 (1H, ddd, J=1.8 Hz, 8.3 Hz, 7.3 Hz), 8.18 (1H, dd, J=1.9, 7.8 Hz), 8.47 (1H, br s). $^{13}$C-NMR (125 MHz, CDCl$_3$, δ) 34.7, 39.1, 55.8, 56.0, 111.3, 113.1, 117.7, 118.8, 121.1, 121.6, 123.8, 132.1, 132.6, 144.8, 150.3, 157.5, 165.3, 201.0. HRMS (ESI) calcd for C$_{18}$H$_{20}$N$_2$NaO$_4^+$ ([M+Na]$^+$): 351.1315, found: 351.1312.

Synthesis Example F-6

Compound 6: N-[3-(2-amino-5-methoxyphenyl)-3-oxopropyl]-2-naphthamide

[Chemical formula 51]

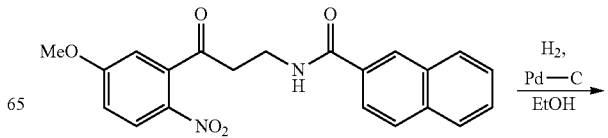

[Chemical formula: MeO-substituted 2-aminophenyl ketone with propyl-NH-C(O)-naphthyl group]

According to the procedure described above for acetamide, Compound e6, i.e., the nitrobenzene derivative, (22 mg, 0.058 mmol) was treated with 10% palladium on carbon (3 mg) in EtOH (1 mL) to give a crude amine. The residue was chromatographed on silica gel (40% to 60% AcOEt/hexane) to give 18 mg (89%) of an aniline derivative (title compound). The product was recrystallized from toluene.

Yellow powder. mp 113.5-114.5° C. $^1$H-NMR (500 MHz, CDCl$_3$, δ) 3.34 (2H, t, J=5.5 Hz), 3.77 (3H, s), 3.93 (2H, q, J=5.8 Hz), 6.66 (1H, d, J=9.0 Hz), 6.98 (1H, dd, J=2.9 Hz, 9.0 Hz), 7.09 (1H, br s), 7.19 (1H, d, J=2.9 Hz), 7.51-7.57 (2H, m), 7.81-7.93 (4H, m), 8.28 (1H, s). $^{13}$C-NMR (125 MHz, CDCl$_3$, δ) 35.1, 38.8, 56.0, 113.0, 117.6, 119.0, 123.6, 124.0, 126.7, 127.4, 127.6, 127.7, 128.4, 128.9, 131.7, 132.6, 134.7, 144.8, 150.4, 167.4, 201.2. HRMS (ESI) calcd for C$_{21}$H$_{20}$N$_2$NaO$_3^+$ ([M+Na]$^+$): 371.1366, found: 371.1365.

Synthesis Example F-7

Compound 7: N-[3-(2-amino-5-methoxyphenyl)-3-oxopropyl]-2-picolinamide

[Chemical formula 52]

According to the procedure described above for acetamide, Compound e7, i.e., the nitrobenzene derivative, (22 mg, 0.067 mmol) was treated with 10% palladium on carbon (8 mg) in EtOH (1 mL) to give a crude amine. The residue was chromatographed on silica gel (40% to 50% AcOEt/hexane) to give 11 mg (53%) of an aniline derivative (title compound).

Yellow powder. mp 114.0-115.5° C. $^1$H-NMR. (500 MHz, CDCl$_3$, δ) 3.30 (2H, t, J=5.9 Hz), 3.76 (3H, s), 3.90 (2H, q, J=6.1 Hz), 6.64 (1H, d, J=9.0 Hz), 6.97 (1H, dd, J=2.9 Hz, 9.0 Hz), 7.18 (1H, d, J=2.8 Hz), 7.40 (1H, ddd, J=1.2 Hz, 4.7 Hz, 7.6 Hz), 7.83 (1H, dt, J=1.7 Hz, 7.7 Hz), 8.18 (1H, td, J=1.0, 7.8 Hz), 8.52 (1H, br s), 8.55 (1H, ddd, J=0.8 Hz, 1.7 Hz, 4.8 Hz). $^{13}$C-NMR (125 MHz, CDCl$_3$, δ) 34.5, 38.9, 56.0, 113.1, 117.6, 118.9, 122.1, 123.8, 126.1, 137.2, 144.9, 148.1, 149.9, 150.2, 164.4, 200.3. HRMS (ESI) calcd for C$_{16}$H$_{17}$N$_3$NaO$_3^+$ ([M+Na]$^+$): 322.1162, found: 322.1157.

Synthesis Example F-8

Compound 8: N-[3-(2-amino-5-chlorophenyl)-3-oxopropyl]-acetamide

[Chemical formula 53]

Tin (II) chloride dihydrate (72 mg, 0.32 mmol) was added to THF (0.5 mL) and a solution of Compound e8, i.e., the nitrobenzene derivative, (17 mg) in ethanol (0.5 mL), and the solution was stirred at room temperature for 25 hours. A 2 M aqueous NaOH solution was added to the reaction mixture and stirred for an hour. The resulting solution was extracted with AcOEt. The organic layer was washed with brine, and dried and evaporated with Na$_2$SO$_4$. The residue was applied to PLC (20% iPrOH, hexane) to give 3 mg (23%) of an aniline derivative of interest (title compound). The product was recrystallized from toluene and hexane.

Yellow powder. mp 121-122° C. $^1$H-NMR (500 MHz, CDCl$_3$, δ) 1.96 (3H, s), 3.16 (2H, t, J=5.6 Hz), 3.64 (2H, q, J=5.8 Hz), 6.12 (1H, bs), 6.62 (1H, d, J=8.80 Hz), 7.22 (1H, dd, J=8.8 Hz, 2.4 Hz), 7.65 (1H, d, J=2.4 Hz). $^{13}$C-NMR (125 MHz, CDCl$_3$, δ) 23.4, 34.4, 38.7, 76.7, 77.0, 77.3, 118.1, 118.8, 120.4, 130.2, 134.7, 148.7, 170.1, 200.5. HRMS (ESI) calcd for C$_{11}$H$_{13}$ClN$_2$NaO$_2^+$ ([M+Na]$^+$): 263.0558. found: 263.0551.

Synthesis Example E-9

Compound e9: N-[3-(2-nitrophenyl)-3-oxopropyl]-acetamide

Step 1

[Chemical formula 54]

-continued

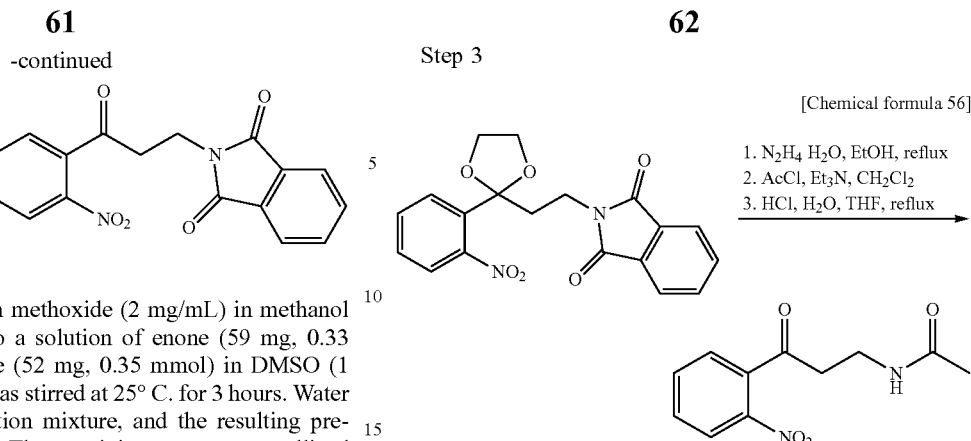

A solution of sodium methoxide (2 mg/mL) in methanol (0.8 mL) was added to a solution of enone (59 mg, 0.33 mmol) and phthalimide (52 mg, 0.35 mmol) in DMSO (1 mL), and the solution was stirred at 25° C. for 3 hours. Water was added to the reaction mixture, and the resulting precipitate was collected. The precipitate was recrystallized from methanol to give 73 mg (68%) of a phthalimide derivative.

White powder. $^1$H-NMR (400 MHz, CDCl$_3$, δ) 3.24 (2H, t, J=7.0 Hz), 4.2 (2H, t, J=7.0 Hz), 7.46 (1H, dd, J=1.3 Hz, 7.5 Hz), 7.61 (1H, ddd, J=1.5 Hz, 7.5 Hz, 8.3 Hz), 7.71-7.73 (3H, m), 7.86 (2H, dd, J=3.1 Hz, 5.5 Hz), 8.1 (1H, dd, J=1.0 Hz, 8.2 Hz). $^{13}$C-NMR (125 MHz, CDCl$_3$, δ) 33.1, 40.8, 123.3, 124.5, 127.5, 130.7, 132.0, 134.0, 134.4, 137.3, 145.6, 168.1, 199.5. HRMS (ESI) calcd for C$_{17}$H$_{12}$N$_2$NaO$_5{}^+$ ([M+Na]$^+$): 347.0638. found: 347.0635.

Step 2

[Chemical formula 55]

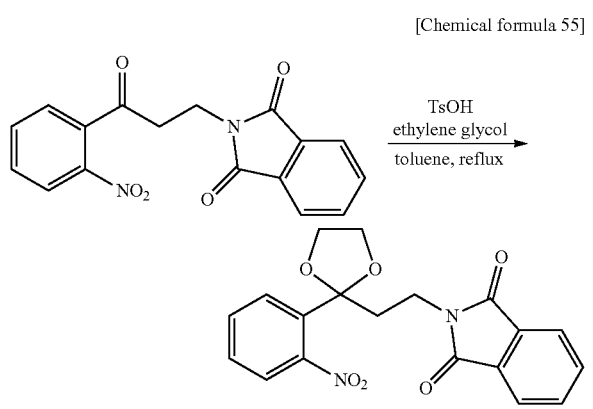

To a solution of the phthalimide derivative (72 mg, 0.22 mmol) obtained in Step 1 described above in toluene (1.8 mL) and ethylene glycol (0.4 mL), p-toluenesulfonic acid monohydrate (18 mg) was added, and the solution was heated at reflux for 21 hours. The mixture was poured into ice, and subjected to extraction with ethyl acetate. The organic layer was washed with brine, and dried and evaporated with Na$_2$SO$_4$. The residue was chromatographed on silica gel (20% to 30% AcOEt/hexane) to give 73 mg (89%) of cyclic acetal.

Colorless solid. $^1$H-NMR (500 MHz, CDCl$_3$, δ) 2.61 (2H, t, J=6.5 Hz), 3.61-3.64 (2H, m), 3.93 (2H, t, J=6.6 Hz), 4.02-4.04 (2H, m), 7.39-7.40 (2H, m), 7.48 (1H, ddd, J=3.6 Hz 5.2 Hz, 7.9 Hz), 7.61 (1H, d, J=7.7 Hz), 7.70 (2H, dd, J=3.0 Hz, 5.5 Hz), 7.84 (2H, dd, J=3.1 Hz, 5.4 Hz). $^{13}$C-NMR (125 MHz, CDCl$_3$, δ) 32.7, 36.8, 64.9, 108.3, 123.1, 123.1, 128.4, 129.4, 131.1, 132.3, 133.8, 135.1, 149.5, 168.3. HRMS (ESI) calcd for C$_{19}$H$_{16}$N$_2$NaO$_6{}^+$ ([M+Na]$^+$): 391.0901. found: 391.0900.

Step 3

[Chemical formula 56]

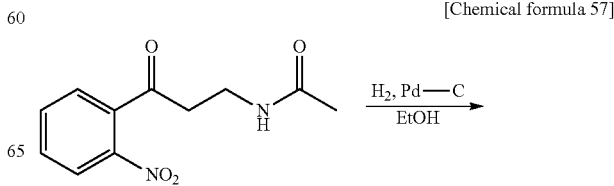

To a solution of cyclic acetal (phthalimide derivative) (67 mg, 0.18 mmol) obtained in Step 2 described above in EtOH (2 mL), hydrazine monohydrate (0.1 mL) was added, and the solution was heated at reflux for 30 minutes. The solution was cooled and acidified with a 2N aqueous HCl solution. This solution was filtrated through a celite pad. The filtrate was washed with hexane, and the aqueous layer was made alkaline with solid KOH. The aqueous layer was subjected to extraction with AcOEt. The organic layer was washed with brine, and dried and evaporated with Na$_2$SO$_4$. The residue was chromatographed on Al$_2$O$_3$ (1% to 5% MEOH/CH$_2$Cl$_2$) to give an amine-containing mixture. The mixture was dissolved in CH$_2$Cl$_2$ (0.8 mL) and Et$_3$N (0.2 mL). Acetyl chloride (0.1 mL) was added to the solution of the mixture at 0° C., which was then stirred at room temperature for 12 hours. An aqueous sodium bicarbonate solution was added to the reaction mixture, and the resultant was subjected to extraction with CH$_2$Cl$_2$. The organic layer was washed with water, and dried and evaporated with Na$_2$SO$_4$. The residue was chromatographed on Al$_2$O$_3$ (1% to 2% EtOH/CH$_2$Cl$_2$) to give 11 mg (39%) of a crude amide. The crude amide was dissolved in THF (1 mL) and a 1% aqueous HCl solution (0.3 mL), and the solution was heated at reflux for 26 hours. The reaction mixture was neutralized with an aqueous sodium bicarbonate solution, and subjected to extraction with AcOEt. The organic layer was washed with brine, and dried and evaporated with Na$_2$SO$_4$. PLC (2% MEOH/hexane) was applied to the residue to give 3.8 mg (9%) of a product (title compound).

$^1$H-NMR (400 MHz, CDCl$_3$, δ) 2.02 (3H, s), 3.04 (2H, t, J=5.5 Hz), 3.70 (2H, q, J=5.8 Hz), 6.13 (1H, bs), 7.39 (1H, dd, J=1.3 Hz, 7.6 Hz), 7.63 (1H, ddd, J=1.5 Hz, 8.3 Hz, 7.5 Hz), 7.74 (1H, dt, J=1.2 Hz, 7.5 Hz), 8.13 (1H, dd, J=1.0 Hz, 8.2 Hz). $^{13}$C-NMR (125 MHz, CDCl$_3$, δ) 23.3, 34.1, 42.4, 124.6, 127.0, 130.8, 134.4, 137.3, 145.5, 145.5, 170.4, 202.0. HRMS (ESI) calcd for C$_{11}$H$_{12}$N$_2$NaO$_4{}^+$ ([M+Na]$^+$): 259.0689, found: 259.0683.

Synthesis Example F-9

Compound 9: N-[3-(2-aminophenyl)-3-oxopropyl]acetamide

[Chemical formula 57]

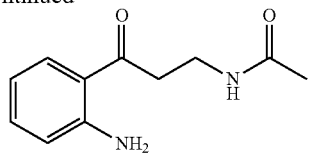

According to the procedure described above for the methoxyphenyl derivative, Compound e9, i.e., the nitrobenzene derivative, (5 mg, 0.022 mmol) was treated with 10% palladium on carbon (4 mg) in EtOH (1 mL) to give a crude amine. The residue was recrystallized from toluene and hexane to give 4 mg (80%) of an aniline derivative (title compound).

Colorless oil. $^1$H-NMR (500 MHz, CDCl$_3$, δ) 1.95 (3H, s), 3.19 (2H, t, J=5.6 Hz), 3.65 (2H, q, J=5.8 Hz), 6.16 (1H, bs), 6.27 (2H, bs), 6.64-6.67 (2H, m), 7.28 (2H, dt, J=7.8 Hz, 1.6 Hz), 7.69 (1H, dd, J=8.5 Hz, 1.3 Hz). $^{13}$C-NMR (125 MHz, CDCl$_3$, δ) 23.4, 34.5, 38.6, 116.1, 117.4, 117.6, 131.1, 134.7, 150.3, 170.0, 201.5. HRMS (ESI) calcd for $C_{11}H_{14}N_2NaO_2^+$ ([M+Na]$^+$): 229.0947. found: 229.0941.

Synthesis Example G-1

Compound 10: N-[3-(2-formylamino-5-methoxyphenyl)-3-oxopropyl]acetamide

[Chemical formula 58]

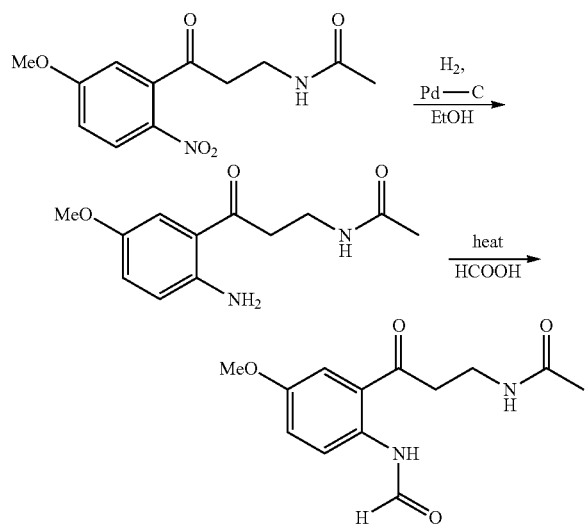

A suspension of Compound e1, i.e., the nitrobenzene derivative, (17 mg, 0.64 mmol) and 10% palladium on carbon (13 mg) in ethanol was stirred in a hydrogen atmosphere at room temperature for 2 hours. The mixture was filtrated through a celite pad. The filtrate was concentrated under reduced pressure. The resulting crude amine was dissolved in formic acid, and the solution was heated at reflux for 3 hours. The reaction mixture was extracted with CHCl$_3$-methanol. The organic layer was washed with an aqueous sodium bicarbonate solution and brine, and dried and evaporated with Na$_2$SO$_4$. The residue was chromatographed on silica gel (1% to 5% EtOH/CH$_2$Cl$_2$) to give 8 mg (48%) of formamide (title compound). The product was recrystallized from toluene and hexane.

Pale yellow powder. mp 85-87° C. $^1$H-NMR (500 MHz, CDCl$_3$, δ) 3.40 (2H, t, J=5.67 Hz), 3.84 (3H, s), 3.87 (3H, q, J=5.8 Hz), 6.77 (1H, bs), 7.14 (1H, dd, J=9.2 Hz, 2.9 Hz), 7.52-7.40 (5H, m), 7.76-7.75 (1H, m), 8.45 (1H, d, J=1.8 Hz), 8.68 (1H, d, J=9.2 Hz), 11.23 (1H, s). $^{13}$C-NMR (125 MHz, CDCl$_3$, δ) 34.9, 39.6, 55.7, 115.5, 121.0, 122.6, 123.2, 126.9, 128.6, 131.6, 133.3, 134.2, 154.9, 159.4, 167.5, 203.6. HRMS (ESI) calcd for $C_{18}H_{18}N_2NaO_4^+$ ([M+Na]$^+$): 349.1159. found: 349.1149.

Synthesis Example G-3

Compound 12: N-[3-(2-formylamino-5-methoxyphenyl)-3-oxopropyl]benzamide

[Chemical formula 59]

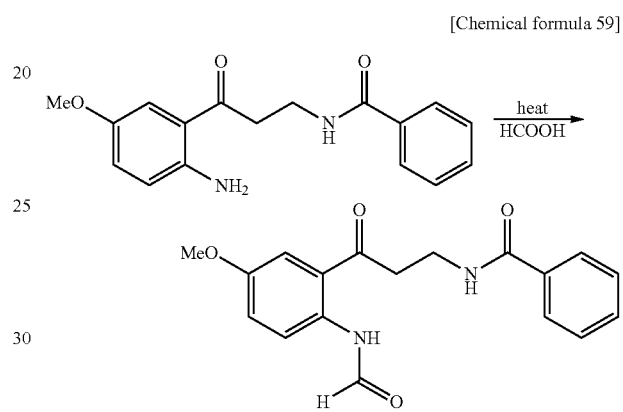

A solution of Compound 3, i.e., the aniline derivative, (18 mg, 0.059 mmol) in formic acid (1 mL) was heated at reflux for 12 hours. The reaction mixture was extracted with CHCl$_3$. The organic layer was washed with brine, and dried and evaporated with Na$_2$SO$_4$. The residue was chromatographed on silica gel (40% to 80% AcOEt/hexane) to give 4 mg (18%) of formamide (title compound). The product was recrystallized from AcOEt and hexane.

Pale yellow powder. mp 131-134° C. $^1$H-NMR (500 MHz, CDCl$_3$, δ) 1.14 (3H, t, J=7.6 Hz), 2.19 (2H, q, J=7.6 Hz), 3.28 (2H, t, J=5.7 Hz), 3.66 (2H, q, J=5.8 Hz), 3.84 (3H, s), 6.02 (1H, bs, J=6.8 Hz), 7.14 (1H, dd, J=9.2 Hz, 2.9 Hz), 7.38 (1H, d, J=3.0 Hz), 8.45 (1H, d, J=1.9 Hz), 8.68 (1H, d, J=9.2 Hz), 11.22 (1H, bs). $^{13}$C-NMR (125 MHz, CDCl$_3$, δ): 9.7, 29.7, 34.3, 39.7, 55.7, 115.6, 120.8, 122.6, 123.2, 133.3, 154.9, 159.4, 173.9, 203.5, HRMS (ESI) calcd for $C_{14}H_{18}N_2NaO_4^+$ ([M+Na]$^+$): 301.1159, found: 301.1158.

Synthesis Example G-4

Compound 13: N-[3-(2-acetylamino-5-methoxyphenyl)-3-oxopropyl]acetamide

[Chemical formula 60]

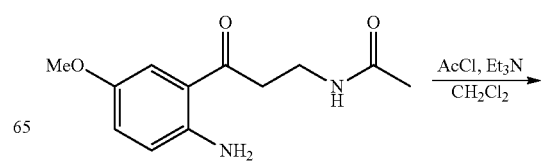

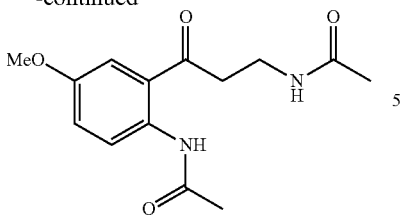

Acetyl chloride (0.01 mL) was added to a solution of Compound 1, i.e., the aniline derivative, (3 mg, 0.12 mmol) in $CR_2Cl_2$ (0.5 mL) and triethylamine (0.05 mL), and stirred at room temperature for 2 hours. The reaction mixture was extracted with $CH_2Cl_2$. The organic layer was washed with water, and dried and evaporated with $Na_2SO_4$. The residue was chromatographed on silica gel (1% to 5% EtOH/$CH_2Cl_2$) to give 1.4 mg (43%) of an acetanilide derivative (title compound). The product was recrystallized from $CH_2Cl_2$-hexane.

Yellowish brown powder. mp 143-145° C. $^1$H-NMR (500 MHz, CDCl$_3$, δ) 1.98 (3H, s), 2.23 (3H, s), 3.27 (2H, t, J=5.5 Hz), 3.65 (2H, q, J=5.8 Hz), 6.05 (1H, bs), 7.14 (1H, dd, J=9.2 Hz, 3.0 Hz), 7.35 (1H, d, J=3.0 Hz), 8.66 (1H, d, J=9.2 Hz), 11.29 (1H, bs). $^{13}$C-NMR (125 MHz, CDCl$_3$, δ) 23.4, 25.4, 29.7, 34.4, 39.6, 55.7, 115.2, 121.1, 122.2, 122.5, 134.6, 154.4, 169.0, 170.2, 203.4. HRMS (ESI) calcd for $C_{14}H_{18}N_2NaO_4^+$ ([M+Na]$^+$): 301.1159. found: 301.1158.

Synthesis Example G-5

Compound 14: N-[3-(5-chloro-2-formylaminophenyl]acetamide

[Chemical formula 61]

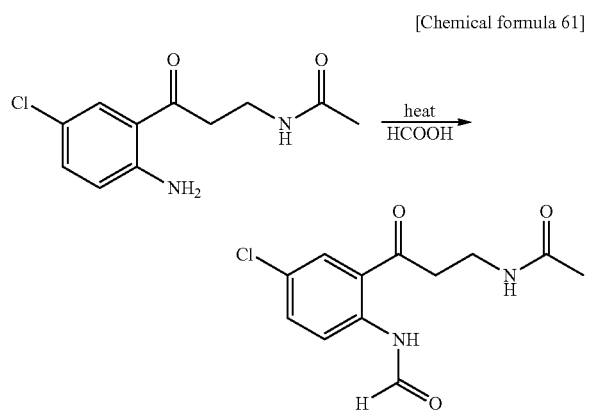

A solution of Compound 8, i.e., the aniline derivative, (3 mg, 0.012 mmol) in formic acid (1 mL) was heated at reflux for 3 hours. The reaction mixture was extracted with CHCl$_3$. The organic layer was washed with brine, and dried and evaporated with $Na_2SO_4$. The residue was chromatographed on silica gel (1% to 4% EtOH/$CH_2Cl_2$) to give 2 mg (64%) of formamide (title compound). The product was recrystallized from toluene.

White powder. mp 169-171° C. $^1$H-NMR (500 MHz, CDCl$_3$, δ) 1.97 (3H, s), 3.29 (2H, t, J=5.7 Hz), 3.65 (2H, q, J=5.9 Hz), 5.99 (1H, bs), 7.53 (1H, dd, J=9.0 Hz, 2.3 Hz), 7.87 (1H, d, J=2.5 Hz), 8.50 (1H, s), 8.75 (1H, d, J=9.0 Hz), 11.43 (1H, bs). $^{13}$C-NMR (125 MHz, CDCl$_3$, δ) 14.1, 22.7, 23.3, 29.7, 34.3, 39.6, 122.5, 123.1, 128.4, 130.5, 135.2, 138.4, 159.6, 170.2, 202.7. HRMS (ESI) calcd for $C_{12}H_{13}ClN_2NaO_3^+$ ([M+Na]$^+$): 291.0507, found: 291.0502.

Example 3

Effects of AMK-Related Synthetic Compounds in Inducing Long-Term Memories in Crickets <Materials and Methods>

3.1. Experimental Animals

Male (young) crickets about one week old following molting into their adult stage were used. Each of the crickets was placed in a 100 ml beaker three days before the experiment, and deprived of water for 2-3 days to enhance the desire of taking water. As the feed, about 10 pieces of insect feed were placed into the beaker.

3.2. Olfactory Associative Conditioning

In the same manner as "1.2, Olfactory associative conditioning" in Example 1, learning/training for smell and reward associative conditioning was conducted.

3.3. Smell Preference Test

In the same manner as "1.3. Smell preference test" in Example 1, a test of smell preference was carried out.

3.4. Drugs

As drugs, the AMK-related synthetic compounds (Compounds 1-10) synthesized in Example 2 above were used. For all of the drugs, 1 mg of the drug was initially dissolved in 100 μl of DMSO, and then diluted with physiological saline for crickets that was 10000 times the amount of the drug solution (final concentration: 1 μg/ml). In the administration experiments, 3 μl was administered to the brain via an aperture opened through a simple eye of the head using a 10-μl syringe.

3.5 Statistical Processing

Processing was conducted in the same manner as "1.5. Statistical processing" in Example 1.

<Results>

Effects of AMK-related synthetic compounds inducing long-term memories

Figure 9:
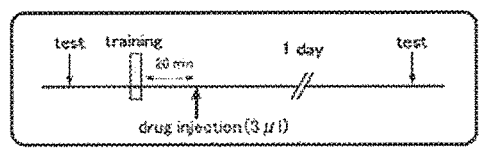
FIG. 9 A diagram showing effects of administration of AMK-related synthetic compounds in inducing a long-term memory. Young crickets one week old following molting into their adult stage were trained once. 20 minutes later, 3 μl each of the AMK-related synthetic compounds (1 μg/ml) were administered to examine the memory a day after the training.
Figure 9:
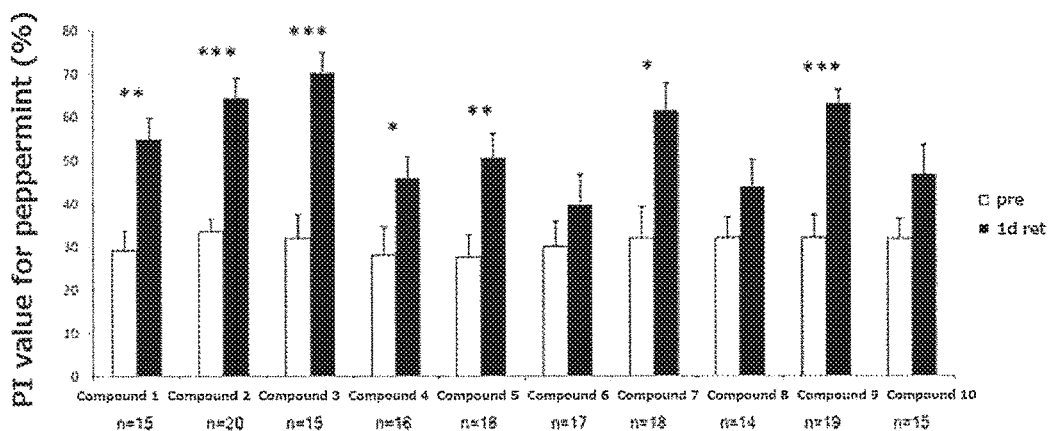

In order to examine the effects of the AMK-related compounds in long-term memory formation, crickets received single-time training and they were administered with any one of Compounds 1-10 (administering 3 μl of 1 μg/ml) 20 minutes later to examine the long-term memory after one day. Significant effects in inducing long-term memories were observed for Compounds 1-5, 7 and 9 (FIG. 9). Compounds that had superior effects over AMK were Compounds 2, 3, 7 and 9. On the other hand, Compounds 6, 8 and 10 did not show significant difference with the number of individuals used this time but they showed a tendency to induce long-term memories.

<Discussion>

While melatonin metabolites (mainly AMK) in the body were found to have an effect in inducing long-term memories in Example 1, the same effect was also observed for various AMK-related synthetic compounds as well in Example 3.

Verifications of AMK-related synthetic compounds for the effect similar to AMK that is expected to enhance a long-term memory is very worthwhile in view of clinical applications.

In this example, Compounds 2, 3, 7 and 9 were found to have stronger effects in forming long-term memories than AMK. These derivatives and further developed related compounds can be expected as long-term memory inducing agents to improve a "learning/memory disorder" involved in various diseases including chronic fatigue syndrome and a "learning/memory disorder (memory/consolidation disorder)" due to dementia represented by Alzheimer's disease. Meanwhile, these drugs are also expected to be effective substances for learning when training police dogs/guide dogs and animals (dolphin, pets, etc.).

Example 4

Object Recognition Test (ORT) with Young Mice
<Materials and Methods>
4.1. Experimental Animals
8-week-old male ICR mice were purchased. Each of the experiment individuals was raised in an individual cage, and adapted to the raising environment for at least a week before use. The rearing room was kept at 22° C. at cycles of 12 hours of light period/12 hours of dark period, and feed and drinking water were given freely. All of the experiments were conducted during the latter 6 hours of the light period.
4.2. Drug
N(1)-acetyl-5-methoxykynuramine (AMK) was used as a drug. AMK was diluted with physiological saline. In the administration experiment, a dosage of 0.001 mg-1 mg/3.65 ml/kg bw was intraperitoneally administered.
4.3. Measurement of Brain AMK Level
1 mg/kg bw of AMK was intraperitoneally administered, and 5, 15, 30, 60, 120 and 240 minutes later, the hippocampus and a region including the perirhinal cortex of the temporal lobe that was assumed to be involved in object recognition memory were collected to measure the AMK levels with a high-performance liquid chromatograph mass spectrometer. As a control group, AMK levels in untreated individuals were also measured
4.4. Object Recognition Test
For an object recognition test, two each of two types of objects (height 6 cm×diameter 4 cm, height 7 cm×diameter 7 cm) and an observation box (height 30 cm×width 40 cm×depth 30 cm) were used. This test consisted of an acquisition trial and a test trial, and the experimental individuals were allowed to explore in the observation box 5 minutes a day for 3 days immediately before the experiment in order to adapt the experimental individuals to the observation box. In the acquisition trial, two identical objects were presented to the observation box and the experimental individuals were allowed to search for a minute. When the acquisition trials were conducted for more than one time, the acquisition trials were conducted at one-hour intervals. The test trial was conducted 24 hours, or 4 or 7 days after the last acquisition trial. In the test trials, one of the two identical objects presented in the acquisition trials was exchanged with a different object (new object), and the experimental individuals were allowed to search for 5 minutes. During the test trials, the time that took each of the mice to search for the object was measured, and the ratio of the searching time of the two objects (DI value:discrimination index) was calculated according to the following formula to examine the relative cognitive levels to the new object.

$$DI \text{ value } (\%) = T_n \times 100/(T_f + T_n)$$

Figure 10:
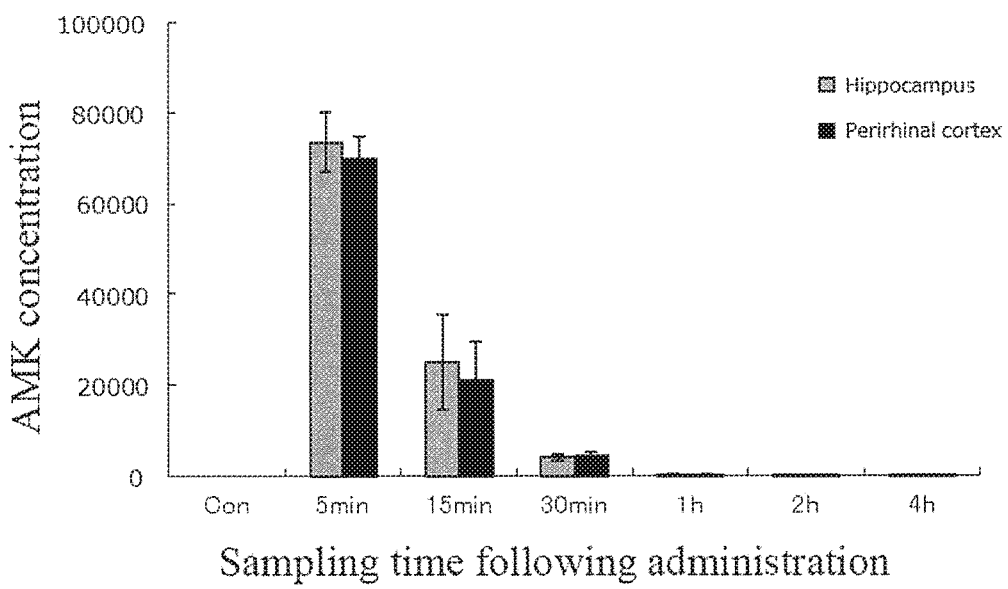
FIG. 10 A diagram showing change in the concentration of intraperitoneally administered AMK in the brain. 1 mg/kg bw of AMK was intraperitoneally administered to young mice, and 5, 15, 30, 60, 120 and 240 minutes later, the hippocampus and a region including the perirhinal cortex of the temporal lobe that was assumed to be involved in object recognition memory were collected to measure the AMK levels with a high-performance liquid chromatograph mass spectrometer. As a control group, AMK levels in untreated individuals were also measured.
Figure 11:
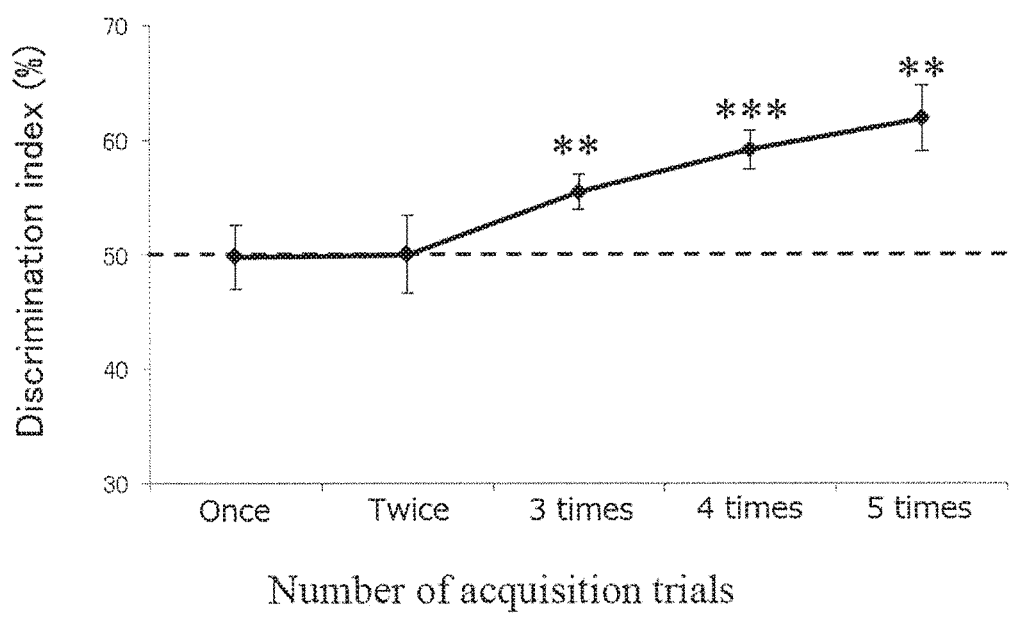
FIG. 11 A diagram showing the relationship between the number of acquisition trials and formation of a long-term memory. Untreated young mice received acquisition trials for 1-5 times and a test trial 24 hours later.
Figure 12:
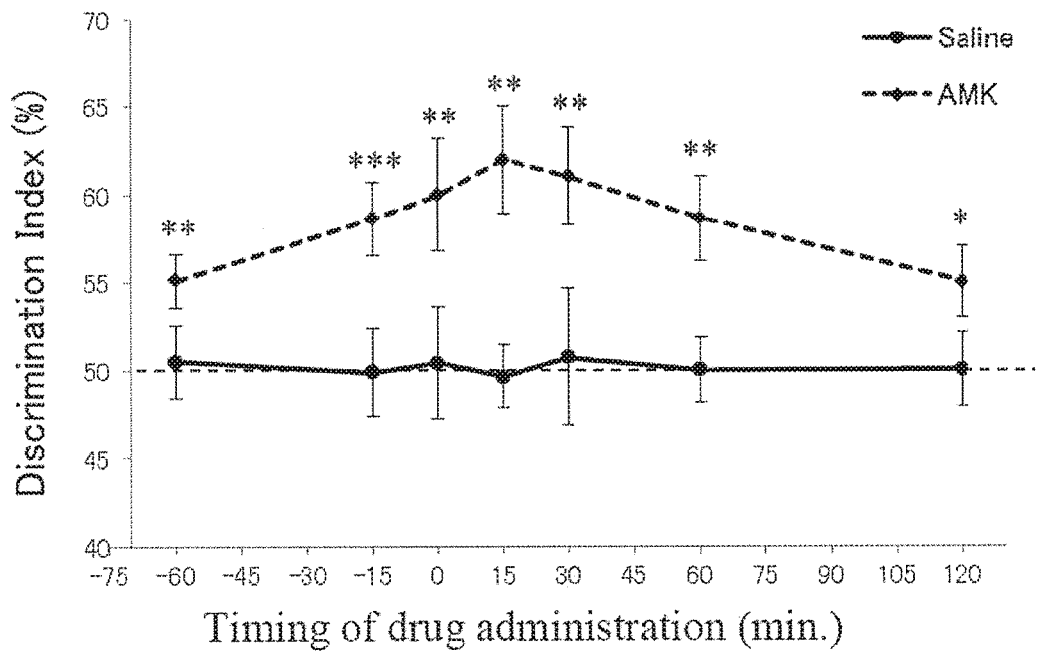
FIG. 12 A diagram showing influence of timing of AMK administration on the induction of a long-term memory. 1 mg/kg bw of AMK was administered at various time points before and after a single-time acquisition trial, and a test trial was conducted 24 hours later.
Figure 13:
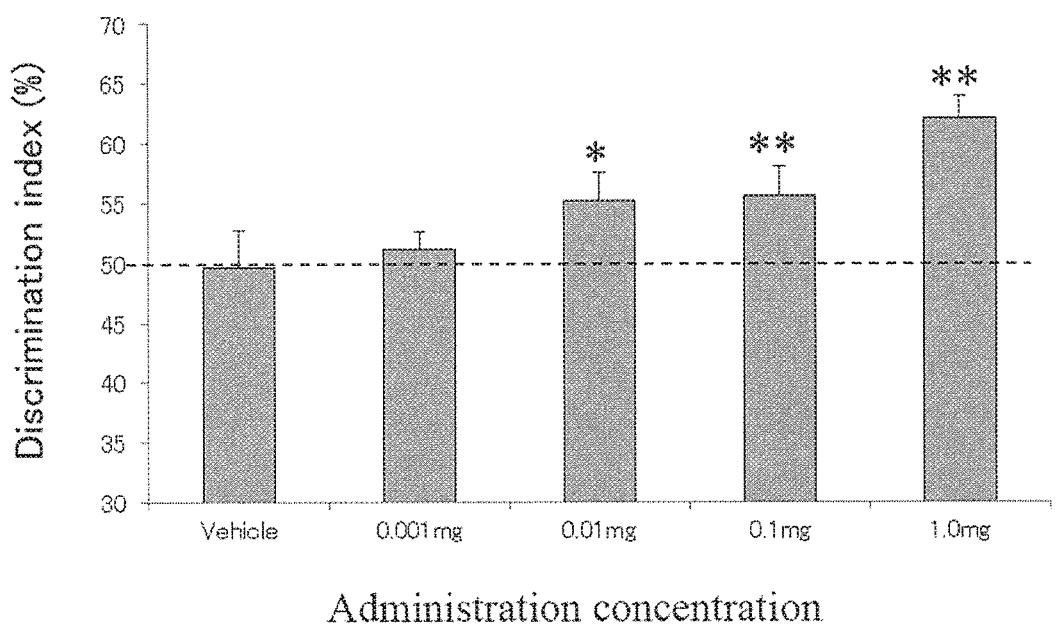
FIG. 13 A diagram showing effects of AMK according to administration concentrations. The concentration-dependent effects of AMK were examined, 15 minutes after the single-time acquisition trial, AMK at concentrations of 0.001 mg/kg bw, 0.01 mg/kg bw, 0.1 mg/kg bw and 1 mg/kg bw were administered, and a test trial was conducted 24 hours later.
Figure 14:
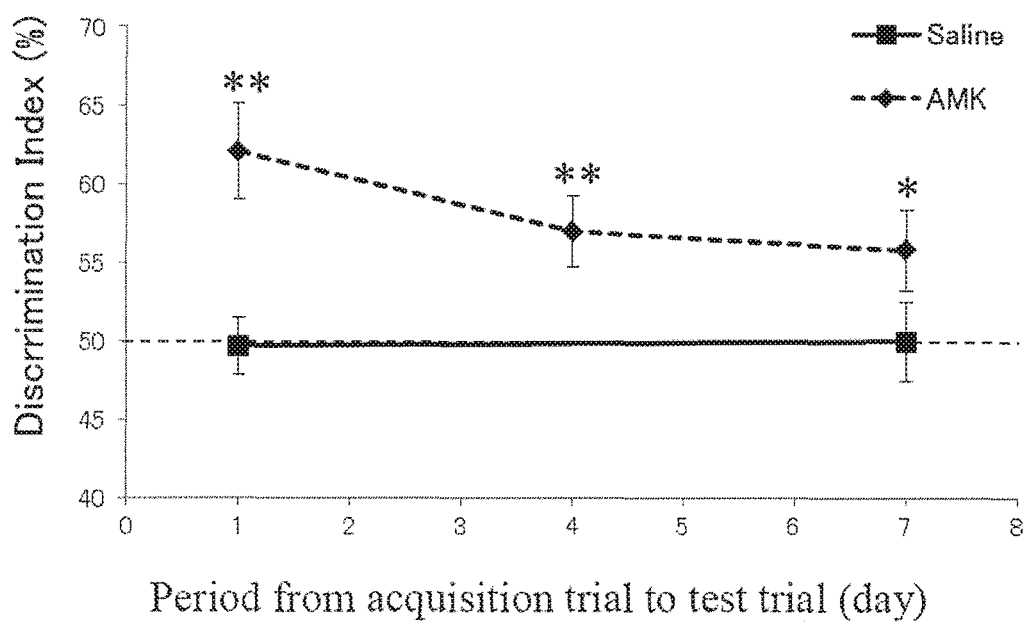
FIG. 14 A diagram showing duration of long-term memory induced by AMK administration. 1 mg/kg bw of AMK or physiological saline was administered to young mice 15 minutes after the single-time acquisition trial, which was followed by test trials 1, 4 and 7 days later to examine whether the long-term memory induced by the drug administration continued for more than 24 hours.

$T_f$: Searching time for object presented in acquisition trial
$T_n$: Searching time for object presented as new object in test trial
The object recognition test was a method of evaluating the learning/memory function that utilizes mice's novelty-seeking behavior. If the mice memorize the object presented upon the acquisition trial and retain that memory upon the test trial, they will search for the new object presented upon the test trial for a longer period of time, and the value will significantly be higher than 50%. On the other hand, if the mice do not retain the memory of the object presented upon the acquisition trial, they will search for both of the two objects presented upon the test trial as newly presented objects, and thus the DI value will be a value near 50%.
4.5. Statistical Processing
One-sample t-test was employed to compare the DI value with the expected value (50%). In each experiment, when comparison among individual groups was required, an unpaired t-test was employed for comparing two groups while multiple comparisons including one-way analysis of variance followed by Bonferroni test was conducted for comparing three or more groups.
<Results>
4.1. Change in Brain AMK Concentration by Intraperitoneal Administration
Whether AMK crosses the blood-brain barrier and the time that takes AMK to reach the brain after intraperitoneal administration were examined. When AMK was intraperitoneally administrated, the AMK concentration significantly increased within 5 minutes in both hippocampus and the perirhinal cortex as compared to the control group, which thereafter significantly decreased with time (FIG. 10). Accordingly, AMK was shown to cross the blood-brain barrier and was found to reach and act in the brain within relatively short time (about 5 minutes) following the intraperitoneal administration.
4.2. Effect of AMK in Inducing Long-Term Memory
In this example, when the untreated individuals received acquisition trials for three or more times in the object recognition test, the DI value significantly increased above 50% in the test trial conducted 24 hours later, whereby formation of long-term memory was confirmed (FIG. 11). In order to examine the effect of AMK in inducing a long-term memory, 1 mg/kg bw of AMK was administered at various time points before and after the acquisition trial under the conditions of a single-time acquisition trial that do not usually form a long-term memory, which was followed by a test trial 24 hours later (FIG. 12). In the AMK-administered group, a long-term memory was formed by administration at least 60 minutes prior to the acquisition trial to 120 minutes following the acquisition trial. Accordingly, AMK was found to induce a long-term memory even by single-dose administration, and was found to be effective when the timing of administration was either before or after the memory acquisition.
4.3. Effects According to Administration Concentrations
In order to observe the concentration-dependent effects of AMK in forming long-term memories, various concentrations of AMK were administered 15 minutes after a single-time acquisition trial, which was followed by a test trial 24 hours later (FIG. 13). While long-term memories were formed at concentrations of 0.01 mg, 0.1 mg and 1 mg/kg bw, a long-term memory was not formed at a concentration of 0.001 mg/kg bw. From this, AMK was found to induce a long-term memory at a concentration as low as at least 0.01 mg/kg.
4.4. Duration of Induced Long-Term Memory
In order to confirm whether the long-term memory induced by administration of AMK can persist for 24 hours or more, 1 mg/kg bw of AMK was administered 15 minutes after the single-time acquisition trial, which was followed by test trials 1, 4 and 7 days later (FIG. 14). As a result, a long-term memory persisted even 4 and 7 days after the acquisition trial. Thus, the memory induced by AMK administration was confirmed to be a long-term memory and this long-term memory was found to persist for at least 7 days.

Example 5

Object Recognition Test (ORT) with Young and Aged Mice

<Materials and Methods>

5.1. Experimental Animals 2-month-old male ICR mice (young mice) and 14-month-old male ICR mice (aged mice) were used. The rearing room was kept at 22° C. at cycles of 12 hours of light period/12 hours of dark period, and feed and drinking water were given freely. All of the experiments were conducted during the latter 6 hours of the light period.

5.2. Drag

N(1)-acetyl-5-methoxykynuramine (AMK) was used as a drug. AMK was diluted with physiological saline for the administration experiment with the aged mouse, and a dosage of 0.1 mg/kg bw or 1 mg/kg bw was intraperitoneally administered.

5.3. Object Recognition Test

For an object recognition test, two each of two types of objects (height 6 cm×diameter 4 cm, height 7 cm×diameter 7 cm) and an observation box (height 30 cm×width 40 cm×depth 30 cm) were used. This test consisted of an acquisition trial and a test trial, and the experimental individuals were allowed to explore in the observation box 5 minutes a day for 3 days immediately before the experiment in order to adapt the experimental individuals to the observation box. In the acquisition trial, two identical objects were presented to the observation box and the experimental individuals were allowed to search for a minute. When the acquisition trials were conducted for more than one time, the acquisition trials were conducted at one-hour intervals. The test trial was conducted 24 hours or 4 days after the last acquisition trial. In the test trials, one of the two identical objects presented in the acquisition trials was exchanged with a different object (new object), and the experimental individuals were allowed to search for 5 minutes. During the test trials, the time that took each of the mice to search for the object was measured, and the ratio of the searching time of the two objects (DI value: discrimination index) was calculated according to the following formula to examine the relative cognitive levels to the new object.

$$DI \text{ value } (\%) = T n \times 100 / (T_f + T_n)$$

$T_f$: Searching time for object presented in acquisition trial $T_n$: Searching time for object presented as new object in test trial 5.4. Statistical Processing One-sample t-test was employed to compare the DI value with the expected value (50%).

<Results>

5.1. Deterioration of Long-Term Memory with Age

Figure 15:
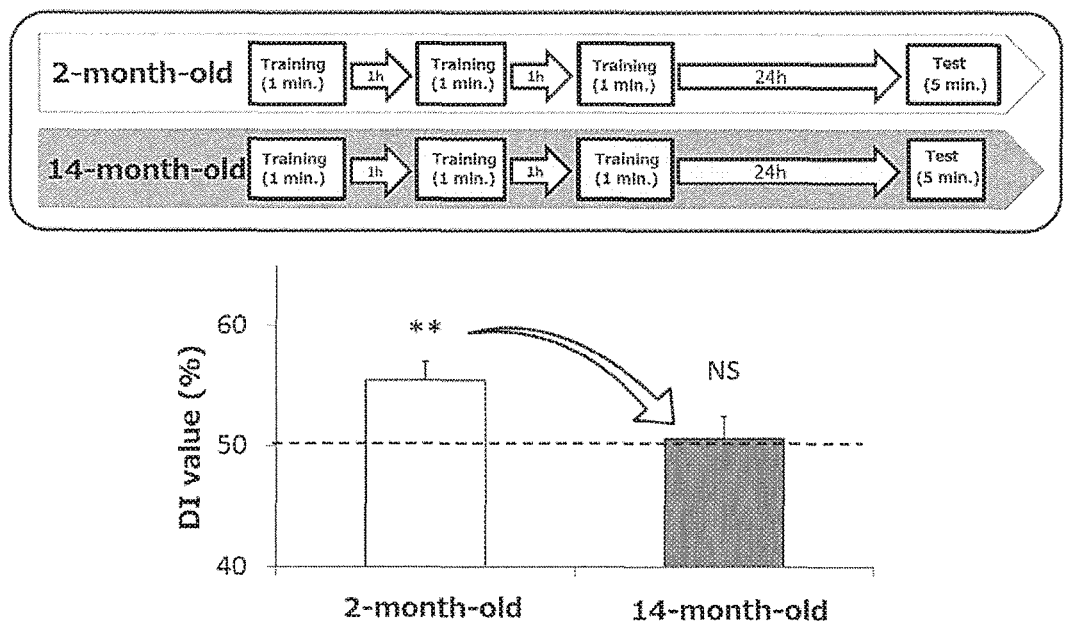
FIG. 15 A diagram showing deterioration of the ability to form long-term memory with age. A young mouse and an aged mouse received acquisition trials for 3 times followed by a test trial 24 hours later to compare their long-term memory formation.

In this example, when young (2-month-old) individuals received one-minute acquisition trials for three times in the object recognition test, the DI values in the test trial 24 hours later was significantly high above 50%, whereby formation of long-term memory was confirmed. On the other hand, a long-term memory was not formed under the same conditions in aged (14-month-old) individuals (FIG. 15).

5.2. Effect of AMK in Inducing Long-Term Memory in Aged Mice

Figure 16:
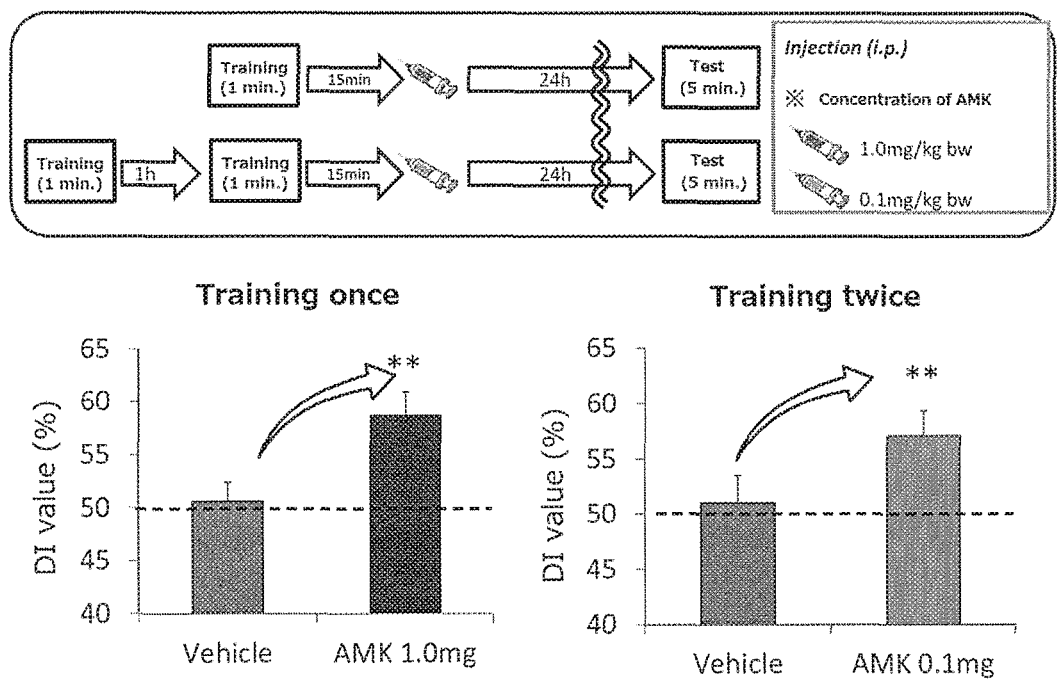
FIG. 16 A diagram showing effects of AMK administration in inducing a long-term memory in aged mice. AMK at a concentration of 1 mg/kg bw or 0.1 mg/kg bw was administered to an aged mouse 15 minutes after 1- or 2-time acquisition trials, which was followed by a test trial 24 hours later.

In order to examine the effect of AMK in inducing a long-term memory, AMK was administered to aged (14-month-old) mice under two conditions that usually do not allow formation of a long-term memory, and a test trial was conducted 24 hours later (FIG. 16). In one condition, 1 mg/kg bw of AMK was administered 15 minutes after conducting a one-minute acquisition trial once. In the other condition, 0.1 mg/kg bw of AMK was administered 15 minutes after conducting one-minute acquisition trials twice. In either experiments, a long-term memory was formed in the AMK-administered group. Accordingly, AMK was found to induce a long-term memory by single-dose administration even in aged mice with low ability in forming long-term memories.

5.3. Duration of Long-Term Memory Induced in Aged Mice

Figure 17:
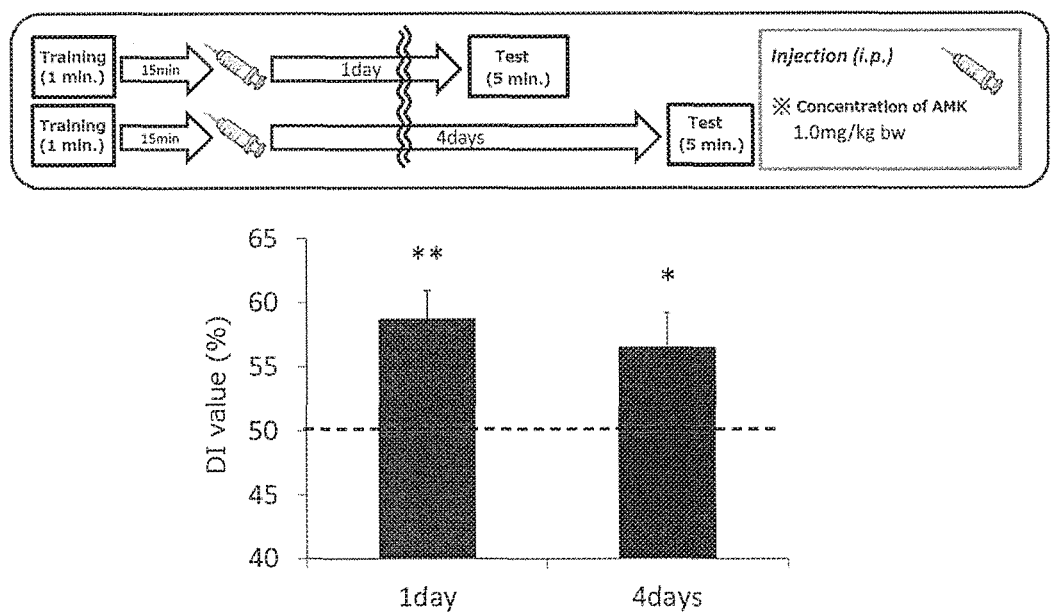
FIG. 17 A diagram showing duration of a long-term memory induced by AMK administration in aged mice. AMK at a concentration of 1 mg/kg bw was administered to the aged mice 15 minutes after a single-time acquisition trial, which was followed by test trials 1 and 4 days later.

In order to confirm that a long-term memory induced by AMK administration persists for 24 hours or more, 1 mg/kg bw of AMK was administered to aged (14-month-old) mice 15 minutes after conducting a one-minute acquisition trial once, and then test trials were conducted 1 and 4 days later (FIG. 17). As a result, a long-term memory persisted even after 4 days following the AMK administration. From this, the memory induced by AMK administration was a long-term memory even in aged mice, and this long-term memory was found to persist for at least 4 days.

<Discussion>

While the effect of AMK in inducing a long-term memory was observed in Example 1 in which crickets were used, the same effect was also confirmed with mice in Examples 4 and 5.

In view of application to human, verification of the effect of AMK that is expected to enhance a memory in mice representing mammals is very significant for clinical application, In this example, an administration concentration that is sufficient to form a long-term memory is 0.01 mg/kg bw, which is about 0.6 mg in terms of human (60 kg), which is a pharmaceutically applicable amount.

In this example, a long-term memory was induced even by administration at least 120 minutes after the acquisition trial. Since 120 minutes to the mice corresponds to about 3 days in terms of human, AMK seems to be highly beneficial in clinical application.

In this example, the single-dose administration of AMK was effective in inducing a long-term memory either before or after the acquisition of memory. There is no other drug that can induce a long-term memory by being administered after the acquisition of memory, and thus it is expected as a prospective drug for treating learning/memory disorders involved in various diseases and dementia.

In this example, since the single-dose administration of AMK was found to be effective in inducing a long-term memory even in aged mice with low ability in forming a long-term memory, AMK is expected as a prospective drug for memory that deteriorates with aging and a patient with mild dementia.

Example 6

Object Recognition Test (ORT) for Young Mice (Application)

<Materials and Methods>

6.1. Experimental Animals

Two-month-old male ICR mice (young mice) were used. The rearing room was kept at 22° C. at cycles of 12 hours of light period/12 hours of dark period, and feed and drinking water were given freely. All of the experiments were conducted during the latter 6 hours of the light period.

6.2. Drug (Application Experiment)

N(1)-acetyl-5-methoxykynuramine (AMK) was used as a drug. AMK was diluted with dimethyl sulfoxide to result a concentration of 0.4 mg/μl. One μl of the diluent was applied to each individual.

6.3. Method of AMK Application

In order to examine the effect of AMK application to the skin, the scalps of the mice were depilated the day before the acquisition trial, AMK or dimethyl sulfoxide as a solvent was applied to 1 cm² of the scalp under inhalation anesthesia with isoflurane (Pfizer) 30 minutes before the acquisition trial, left for 5 minute to dry, and then the applied surface was protected with patchProtect (SmartPractice).

6.4. Object Recognition Test

Test was conducted in the same manner as "5.3 Object recognition test" in Example 5 except that searching time was 3 minutes in the acquisition trial.

6.5. Statistical Processing

Processing was conducted in the same manner as "5.4 Statistical processing" in Example 5.

<Results>

6.1. Effect of AMK Application in Inducing Long-Term Memory

Figure 18:
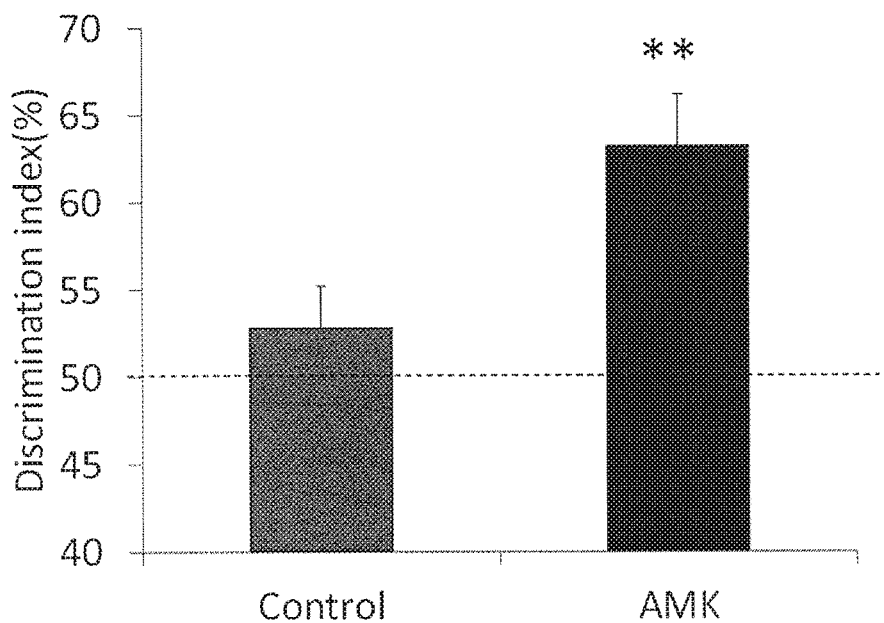
FIG. 18 A diagram showing effects of AMK application in inducing a long-term memory by in young mice. AMK or dimethyl sulfoxide was applied onto the scalps of the young mice, and the mice received a single-time acquisition trial (3 minutes) followed by a test trial 24 hours later.

In order to examine the effect of AMK application to the skin in inducing a long-term memory, young (2-month-old) mice received a 3-minute acquisition trial once and then a test trial was conducted 24 hours later. While a long-term memory was not formed in a control group which received application of only dimethyl sulfoxide, a long-term memory was formed in the group which received AMK application (FIG. 18). From this, AMK application was found to form the long-term memory at the point of 24 hours later, showing that AMK can induce a long-term memory by application to the skin.

<Discussion>

According to this example, since AMK was effective even when applied to the skin, AMK seems to be highly beneficial in clinical application.

Example 7

Object Recognition Test for Young Mice (Melatonin and Melatonin Metabolites)

<Materials and Methods>

7.1, Experimental Animals

Two-month-old male ICR mice (young mice) were used. The rearing room was kept at 22° C. at cycles of 12 hours of light period/12 hours of dark period, and feed and drinking water were given freely. All of the experiments were conducted during the latter 6 hours of the light period.

7.2. Drugs

Melatonin (MEL), N(1)-acetyl-N(2)-formyl-5-methoxykynuramine (AFMK), and N(1)-acetyl-5-methoxykynuramine (AMK) were used as drugs. Melatonin was purchased from SIGMA Aldrich, AFMK was purchased from Cayman Chemical, and AMK was purchased from Toronto Research Chemicals. AFMK and AMK were diluted with physiological saline and intraperitoneally administered at a dosage of 0.01 mg/kg bw, 0.1 mg/kg bw or 1.0 mg/kg bw. MEL was diluted with physiological saline containing 1 vol % ethanol, and intraperitoneally administered at a dosage of 1.0 mg/kg bw or 5.0 mg/kg bw. As controls, physiological saline or physiological saline containing 1 vol % ethanol was intraperitoneally administered.

7.3. Object Recognition Test

Test was conducted in the same manner as "5.3 Object recognition test" in Example 5.

7.4. Statistical Processing

Processing was conducted in the same manner as "5.4 Statistical processing" in Example 5.

<Results>

Figure 19:
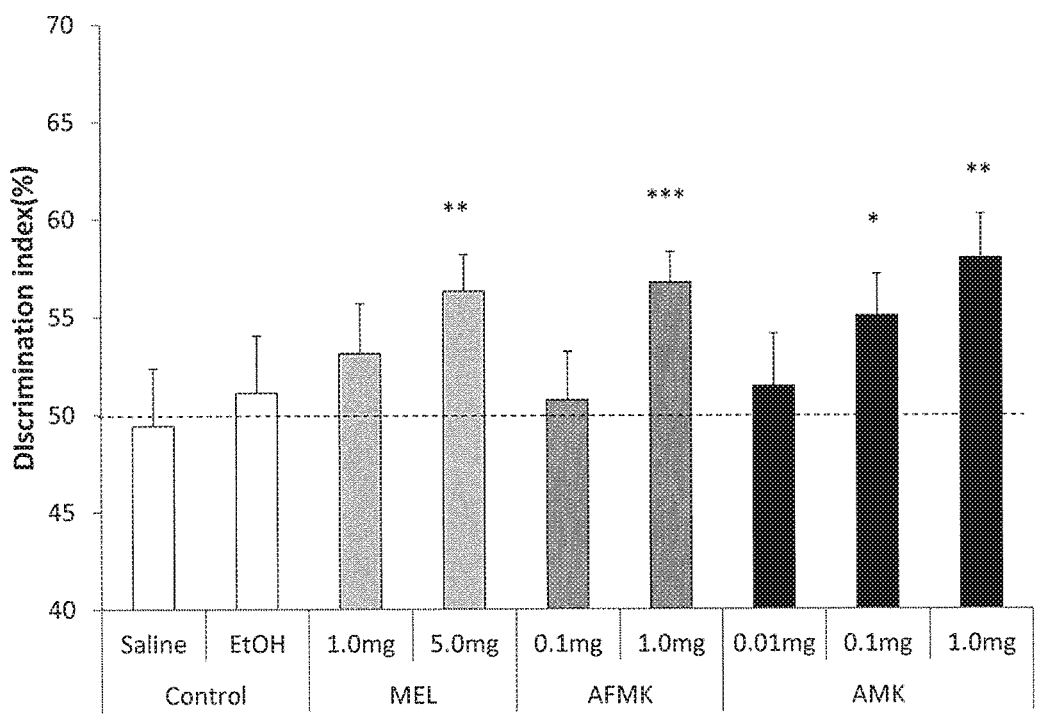
FIG. 19 A diagram comparing effects of administration of melatonin (MEL) and melatonin metabolites (AFMK, AMK) in inducing a long-term memory in young mice. Drugs at concentrations of 0.1 mg/kg bw, 1.0 mg/kg bw or 5.0 mg/kg bw were administered to young mice 60 minutes after a single-time acquisition trial, which was followed by a test trial 24 hours later.

7.1 Effects of Melatonin and Melatonin Metabolites in Inducing Long-Term Memories In order to examine the effects of melatonin (MEL) and melatonin metabolites (AFMK, AMK) in memory formation, the drugs at a concentration of 0.01 mg/kg bw, 0.1 mg/kg bw, 1.0 mg/kg bw or 5.0 mg/kg bw was administered to young mice (2-month-old) 60 minutes after conducting a one-minute acquisition trial once, and then a test trial was conducted 24 hours later (FIG. 19). As a result, MEL, AFMK and AMK were found to have the effects of inducing long-term memories when administered at concentrations of 5.0 mg/kg bw, 1.0 mg/kg bw and 0.1 mg/kg bw, respectively. Among them, AMK was found to have the effect of inducing a long-term memory at the lowest concentration (0.1 mg/kg bw).

<Discussion>

While the effect of AMK in inducing a long-term memory was observed in Example 1 in which crickets were used, the effects of melatonin, AFMK and AMK in inducing long-term memories were also confirmed in Example 7 in which mice were used.

The invention claimed is:

1. A method for inducing a long-term memory in a subject in need thereof, comprising a step of administering a compound represented by Formula I below, a pharmaceutically acceptable salt thereof or a solvate thereof to the subject:

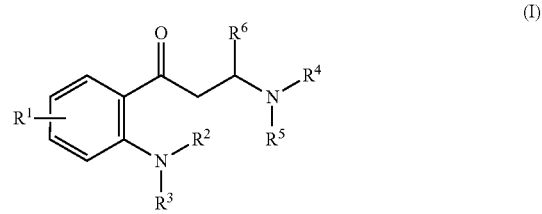

(I)

wherein, $R^1$, $R^2$, $R^3$, $R^4$, $R^5$, and $R^6$ each independently represent a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-21}$ acyl group, an optionally substituted heteroaryl carbonyl group, an optionally substituted $C_{2-7}$ alkoxycarbonyl group, a formyl group, a carboxyl group or a hydroxyl group; and at least one of $R^4$ and $R^5$ is an optionally substituted $C_{2-21}$ acyl group or an optionally substituted heteroaryl carbonyl group.

2. A method for inducing a long-term memory in a subject in need thereof, comprising a step of administering a compound, a pharmaceutically acceptable salt thereof or a solvate thereof to the subject, wherein the compound is any one of Compounds 1-16 below:

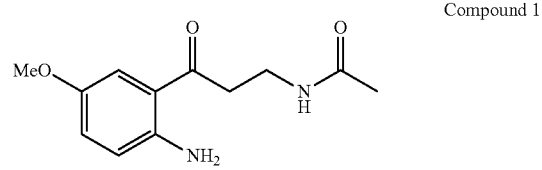

Compound 1

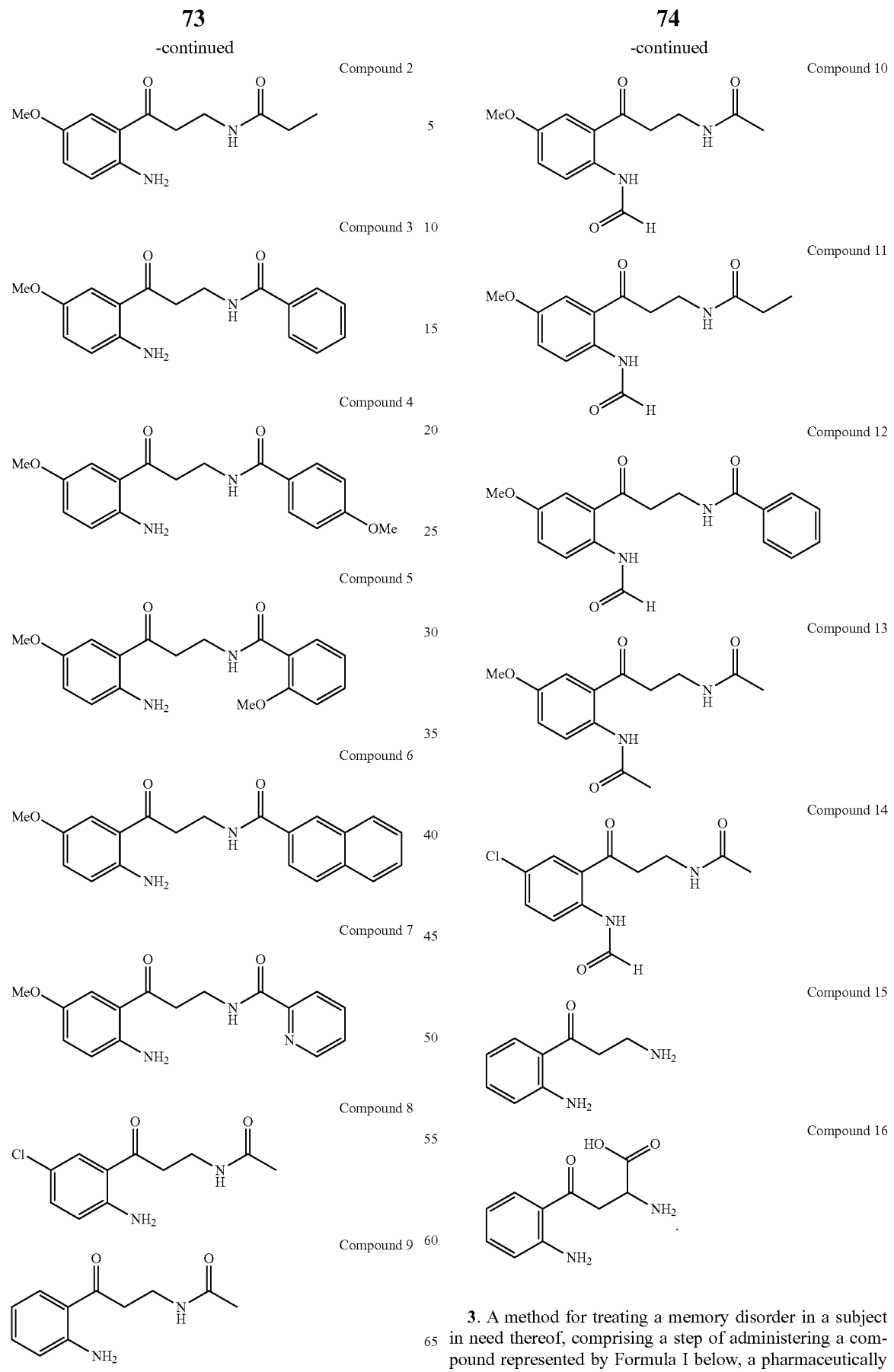
3. A method for treating a memory disorder in a subject in need thereof, comprising a step of administering a compound represented by Formula I below, a pharmaceutically acceptable salt thereof or a solvate thereof to the subject:

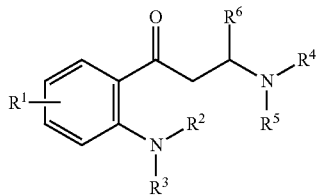

(I)

wherein, $R^1$, $R^2$, $R^3$, $R^4$, $R^5$, and $R^6$ each independently represent a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-21}$ acyl group, an optionally substituted heteroaryl carbonyl group, an optionally substituted $C_{2-7}$ alkoxycarbonyl group, a formyl group, a carboxyl group or a hydroxyl group; and at least one of $R^4$ and $R^5$ is an optionally substituted $C_{2-21}$ acyl group or an optionally substituted heteroaryl carbonyl group.

4. A method for treating a memory disorder in a subject in need thereof, comprising a step of administering a compound, wherein the compound is any one of Compounds 1-16 below:

Compound 1

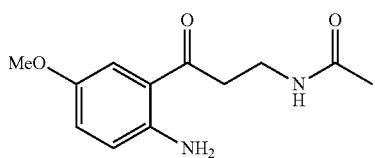

Compound 2

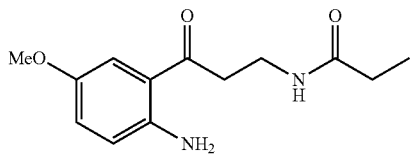

Compound 3

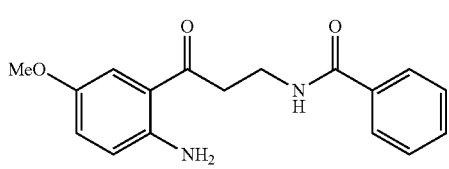

Compound 4

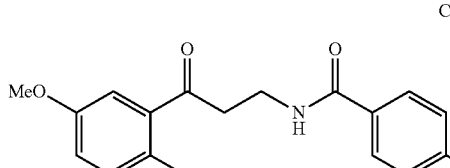

Compound 5

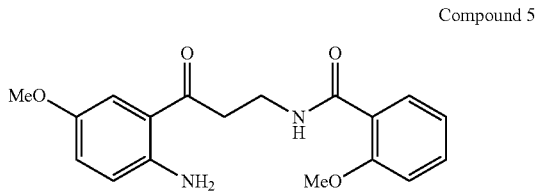

Compound 6

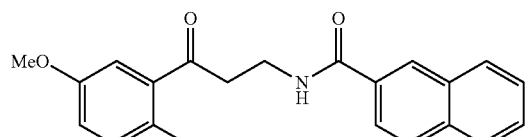

Compound 7

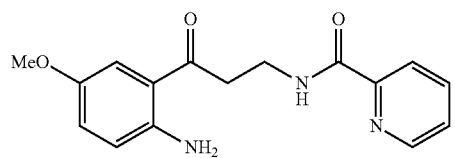

Compound 8

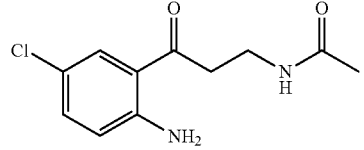

Compound 9

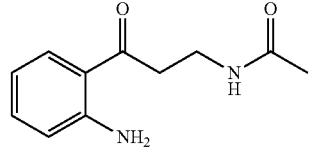

Compound 10

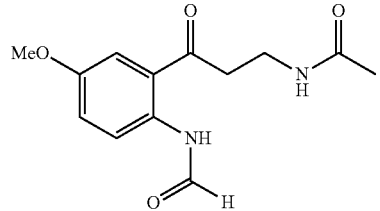

Compound 11

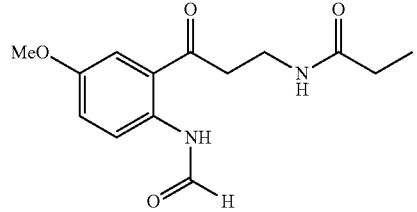

Compound 12

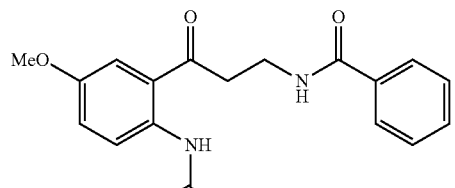

Compound 13

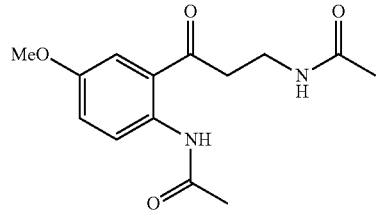

5. A method for inducing a long-term memory in a subject in need thereof, comprising a step of ingesting functional food containing a compound represented by Formula I below, a pharmaceutically acceptable salt thereof or a solvate thereof:

(I)

wherein, $R^1$, $R^2$, $R^3$, $R^4$, $R^5$, and $R^6$ each independently represent a hydrogen atom, a halogen atom, an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{3-8}$ cycloalkyl group, an optionally substituted $C_{6-10}$ aryl group, an optionally substituted $C_{2-21}$ acyl group, an optionally substituted heteroaryl carbonyl group, an optionally substituted $C_{2-7}$ alkoxycarbonyl group, a formyl group, a carboxyl group or a hydroxyl group; and at least one of $R^4$ and $R^5$ is an optionally substituted $C_{2-21}$ acyl group or an optionally substituted heteroaryl carbonyl group.

6. A method for inducing a long-term memory in a subject in need thereof, comprising a step of ingesting functional food containing a compound, wherein the compound is any one of Compounds 1-16 below:

-continued
Compound 9
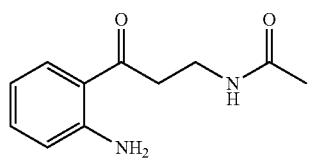
Compound 10
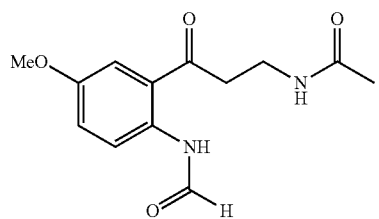
Compound 11
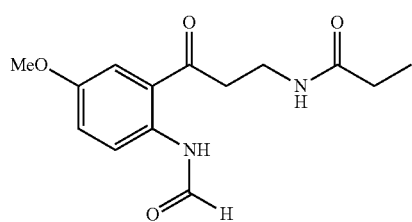
Compound 12
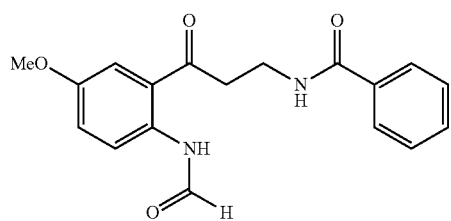
-continued
Compound 13
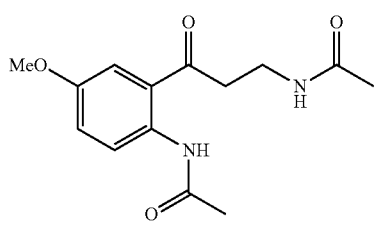
Compound 14
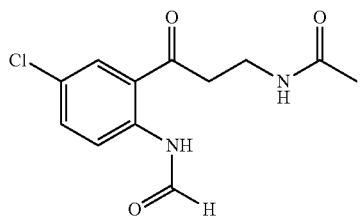
Compound 15
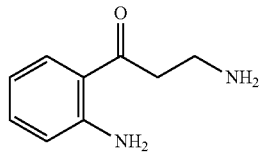
Compound 16
* * * * *